(12) United States Patent
Needham et al.

(10) Patent No.: US 12,145,153 B2
(45) Date of Patent: Nov. 19, 2024

(54) LATERAL FLOW ASSAY CASSETTE

(71) Applicant: InBios International, Inc., Seattle, WA (US)

(72) Inventors: James William Needham, Seattle, WA (US); Gustavo Firnhaber, Seattle, WA (US)

(73) Assignee: InBios International, Inc., Seattle, WA (US)

( * ) Notice: Subject to any disclaimer, the term of this patent is extended or adjusted under 35 U.S.C. 154(b) by 0 days.

(21) Appl. No.: 17/476,329

(22) Filed: Sep. 15, 2021

(65) Prior Publication Data

US 2022/0080408 A1 Mar. 17, 2022

Related U.S. Application Data

(60) Provisional application No. 63/185,316, filed on May 6, 2021, provisional application No. 63/079,355, filed on Sep. 16, 2020.

(51) Int. Cl.
*B01L 3/00* (2006.01)
*G01N 33/569* (2006.01)
*G01N 33/68* (2006.01)

(52) U.S. Cl.
CPC ...... *B01L 3/5029* (2013.01); *G01N 33/56911* (2013.01); *G01N 33/56983* (2013.01); *G01N 33/6803* (2013.01); *B01L 2300/069* (2013.01); *B01L 2300/0816* (2013.01); *B01L 2300/126* (2013.01); *G01N 2800/26* (2013.01)

(58) Field of Classification Search
CPC .......... B01L 3/5029; B01L 2300/069; B01L 2300/0816; B01L 2300/126; B01L 2200/0694; B01L 2300/0609; B01L 2300/0825; B01L 2400/0406; G01N 33/56911; G01N 33/56983; G01N 33/6803; G01N 2800/26; G01N 21/78; G01N 21/8483; G01N 33/54388; A61B 10/0051; A61B 2010/0216; A61B 10/0045

See application file for complete search history.

(56) References Cited

U.S. PATENT DOCUMENTS

| | | | | |
|---|---|---|---|---|
| 4,707,450 A | * | 11/1987 | Nason | B01L 3/5029 604/3 |
| 4,963,325 A | * | 10/1990 | Lennon | B01L 3/508 422/430 |
| 8,399,261 B2 | | 3/2013 | Kabir et al. | |
| 10,996,221 B2 | | 5/2021 | Needham et al. | |
| 2002/0085958 A1 | | 7/2002 | Nemcek et al. | |

(Continued)

FOREIGN PATENT DOCUMENTS

| | | |
|---|---|---|
| EP | 1 870 160 A1 | 12/2007 |
| WO | 95/04280 A1 | 2/1995 |
| WO | 2009/085462 A1 | 7/2009 |

OTHER PUBLICATIONS

BinaxNOWTM COVID-19 Ag CARD, Procedure Card, Aug. 24, 2020, pp. 1-15. (Year: 2020).*

(Continued)

*Primary Examiner* — Dennis White
(74) *Attorney, Agent, or Firm* — Seed IP Law Group LLP

(57) ABSTRACT

A lateral flow assay cassette comprising a swab holder is provided herein. Also provided are kits comprising the lateral flow assay cassette and methods of detecting an analyte.

19 Claims, 10 Drawing Sheets

(56) References Cited

U.S. PATENT DOCUMENTS

2004/0184954 A1    9/2004   Guo et al.
2011/0143365 A1*   6/2011   Buchanan ............. B01L 3/5023
                                                          435/7.1
2015/0323534 A1*  11/2015   Egan ................ G01N 33/56983
                                                            435/5

OTHER PUBLICATIONS

Knappik et al., "Fully Synthetic Human Combinatorial Antibody Libraries (HuCAL) Based on Modular Consensus Frameworks and CDRs Randomized with Trinucleotides," *Journal of Molecular Biology* 296:57-86, 2000.

Shi et al., "De Novo Selection of High-Affinity Antibodies from Synthetic Fab Libraries Displayed on Phage as pIX Fusion Proteins," *Journal of Molecular Biology* 397:385-396, 2010.

Standard Q COVID-19 Ag Home Test, URL=https://www.sdbiosensor.com/product/product_view?product_no=295#, download date Apr. 19, 2022. (5 pages).

* cited by examiner

LATERAL FLOW ASSAY CASSETTE

BACKGROUND

Most assays that require a swab specimen (e.g., nasal, nasopharyngeal, oral) separately process the swab in order to extract the target (RNA, DNA, protein, etc.) prior to running the assay. This may include (but is not limited to) lysis steps, nucleic acid extraction steps and/or enrichment steps. For instance, current PCR testing for SCoV-2 typically requires swab specimens that are first placed in 1 to 3 mL of virus transport media (VTM). After transport to a suitable laboratory, RNA is subsequently extracted from the (now diluted) specimen. Another example of an immunoassay is the CL Detect™ rapid test produced by InBios International, Inc. in which, a 'dental broach' (i.e., a swab with barbs) is used to collect specimen from a lesion in the subject. The broach is incubated with lysis buffer in a separate tube for a period before a volume of the lysis buffer is then transferred onto the rapid test.

BRIEF SUMMARY

Provided herein is a lateral flow assay cassette comprising a swab holder. In some embodiments, the lateral flow assay cassette comprises a sample pad, a conjugate pad, a membrane, an absorbent pad, a sample port, and a swab holder. In a preferred embodiment, the lateral flow assay cassette provides for, or permits, direct contact of a swab with a sample to the surface of the sample pad. In another preferred embodiment, the lateral flow assay cassette provides for, or permits, holding the swab above the sample pad, wherein the swab does not come into direct contact with the sample pad.

The lateral flow assay cassette may also have one or more of the following features, which may be used in combination with one another or other features described in the present disclosure:
the swab holder secures a swab having a stem and a head;
the swab holder comprises protrusions that secure the swab stem;
the swab holder secures the swab head directly above a sample pad;
the swab holder secures the swab head directly in contact with a sample pad;
the protrusions are sized to secure a swab stem of a specific diameter; and/or
the protrusions are flexible and sized to secure swab stems of various diameters.

Further provided herein are methods for detecting an analyte, wherein the method may comprise: (a) providing a lateral flow assay cassette having a swab holder; (b) providing an appropriate swab having a swab head and a swab stem; (c) collecting a sample from a subject using the swab; (d) placing the swab stem into the swab holder; and (e) adding an appropriate amount of lysis buffer to the swab head. In some embodiments, the method further comprises: (f) introducing sample from the swab head to the sample pad; (g) running the assay; and (h) producing an assay result. In certain embodiments, the methods may further comprise the step of adding an appropriate amount of chase buffer after step (e).

The method for detecting an analyte may also have one or more of the following features, which may be used in combination with one another or other features described in the present disclosure:
the swab holder secures the swab head directly above a sample pad;
the swab holder secures the swab head directly in contact with a sample pad;
the sample is a nose, nasopharyngeal cavity, the oropharyngeal cavity, the mid-turbinate region, mouth, tongue, throat, teeth, gums, tonsils, outer ear canal, skin, wounds, lesions, urethra, vagina, cervix, anus, or rectum sample;
the sample is a nasal or ear secretion, sputum, saliva, a vaginal secretion, pus, blood, urine, feces, a bronchoalveolar lavage sample, or a surgical sample;
the detection of the analyte indicates the presence of an infectious agent in the subject, such as Human coronavirus, 229E; Human coronavirus, OC43; Human coronavirus, NL63; MERS-coronavirus; SARS-CoV-2; Adenovirus 21; Human Metapneumovirus (hMPV); Parainfluenza virus 1; Parainfluenza virus 2; Parainfluenza virus 3; Parainfluenza virus 4a; Influenza A; Influenza B; Enterovirus D68; Respiratory syncytial virus; Rhinovirus 40; *Haemophilus* influenza; *Streptococcus pneumonia; Streptococcus pyogenes; Candida albicans; Bordetella pertussis; Mycoplasma* pneumonia; *Chlamydia* pneumonia; *Legionella pneumophila*; or *Staphylococcus aureus;*
the analyte is RNA, DNA, or protein;
the method further comprises detecting the analyte within 30 minutes;
the method further comprises f) introducing sample from the swab head to the sample pad; g) running the assay; and h) producing an assay result; or
the method further comprises adding an appropriate amount of chase buffer to the swab head after step (e).

The present disclosure also provides a kit comprising any lateral flow assay cassette disclosed herein, a swab having a stem with a diameter sized to be secured by the swab holder, and an instruction sheet. The kit may also include lysis buffer and, optionally, chase buffer, or any other components usable with a lateral flow assay cassette or to detect an analyte as disclosed herein.

BRIEF DESCRIPTION OF THE DRAWINGS

FIG. 1A shows an exemplary cassette 1 with a swab holder 3 having "grabber" style protrusions 5. FIG. 1B shows an exemplary cassette 1 with a swab holder 3 having "featherboard" style protrusions 7.

FIG. 4A shows an overhead view of an exemplary cassette 1 with a "featherboard" style swab holder 3, showing placement of a swab in the swab holder with the swab stem 11 secured in the swab holder 3, positioning the swab head 9 over the sample pad. FIG. 4B shows a top and side view of an exemplary cassette 1 with a "featherboard" style swab holder 3, showing placement of a swab in the swab holder with the swab stem 11 secured in the swab holder 3, positioning the swab head 9 over the sample pad.

DETAILED DESCRIPTION

Figure 1A:
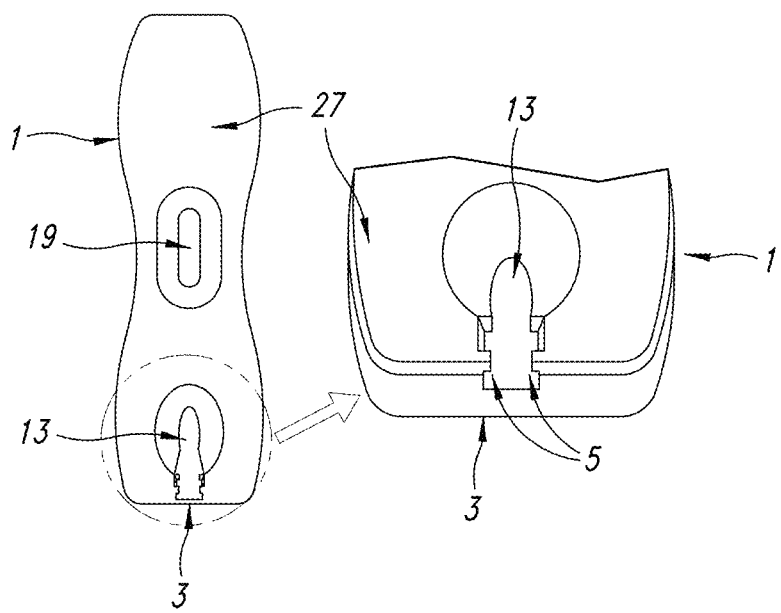
FIGS. 1A and 1B are schematic diagrams of exemplary cassettes 1 comprising swab holders 3.
Figure 1B:
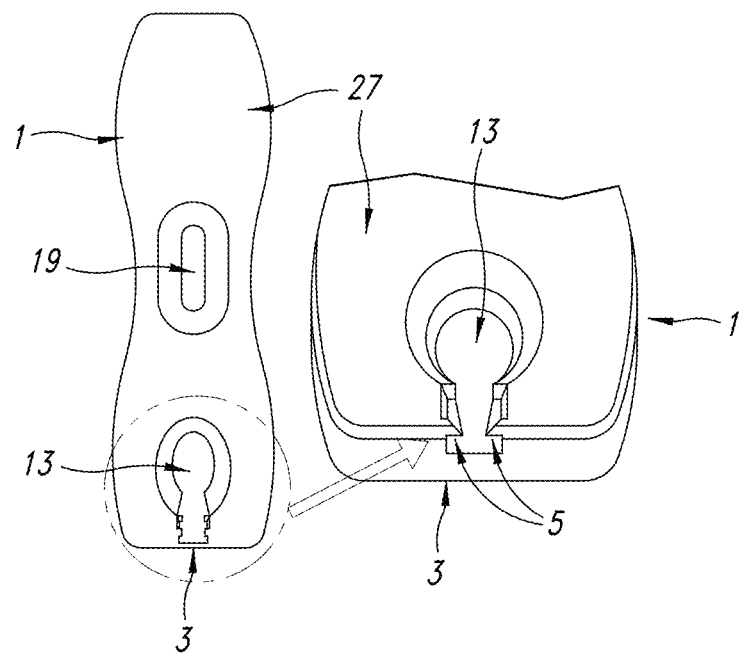

The present disclosure provides for a lateral flow assay cassette comprising a swab holder. As used herein, the term "cassette" refers to the outer housing of a device for a lateral flow assay. Other components of the lateral flow assay may include a sample pad, a conjugate pad, a membrane, an absorbent pad. The cassette includes a sample port, which permits access to the sample pad, and a swab holder, which secures a sample swab. The cassette may include other features, such as one or more viewing ports for viewing a test and/or control line.

The present disclosure also provides an assay for an analyte conducted using the lateral flow assay cassette. The assay may be an immunoassay. The immunoassay may include one or more antibodies that specifically bind the analyte. In some examples. The immunoassay may contain more than one type of antibody that both specifically bind the antigen, or that bind separate antigens. For example, the immunoassay may contain two separate antibodies that both bind different epitopes of one antigen.

In some embodiments, at least one antibody may bind the SARS-CoV-2 Nucleoprotein antigen. The assay may include multiple antibodies that bind different epitopes of the SARS-CoV-2 Nucleoprotein antigen. The assay may also or alternatively include multiple antibodies, one of which binds the SARS-CoV-2 Nucleoprotein antigen, and another of which binds a different SARS-CoV-2 protein antigen, in particular a different SARS-CoV-2 envelope protein.

"Antibodies" is meant in a broad sense and includes immunoglobulin molecules belonging to any class, IgA, IgD, IgE, IgG and IgM, or sub-class IgA1, IgA2, IgG1, IgG2, IgG3 and IgG4 and including either kappa and lambda light chain. Antibodies include monoclonal antibodies, full length antibodies, antigen binding fragments, bispecific multispecific antibodies, dimeric, tetrameric or multimeric antibodies, single chain antibodies, domain antibodies and any other modified configuration of the immunoglobulin molecule that comprises an antigen binding fragment of the required specificity. "Full length antibodies" are comprised of two heavy chains (HC) and two light chains (LC) interconnected by disulfide bonds as well as multimers thereof (e.g. IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL may be further subdivided into regions of hypervariability, termed complementarity determining regions (CDR), interspersed with framework regions (FR). Each VH and VL is composed of three CDRs and four FR segments, arranged from amino-terminus to carboxy-terminus in the following order: FR1, CDR1, FR2, CDR2, FR3, CDR3, and FR4.

"Complementarity determining regions (CDR)" are antibody regions that bind an antigen. There are three CDRs in the VH (HCDR1, HCDR2, HCDR3) and three CDRs in the VL (LCDR1, LCDR2, LCDR3). CDRs may be defined using various delineations such as Kabat. The correspondence between the various delineations and variable region numbering are described. Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification.

"Antigen binding fragment" refers to a portion of an immunoglobulin molecule that binds an antigen. Antigen binding fragments may be synthetic, enzymatically obtainable or genetically engineered polypeptides and include the VH, the VL, the VH and the VL, Fab, F(ab')2, Fd and Fv fragments, domain antibodies (dAb) consisting of one VH domain or one VL domain, shark variable IgNAR domains, camelized VH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3. VH and VL domains may be linked together via a synthetic linker to form various types of single chain antibody designs where the VH/VL domains may pair intramolecularly, or intermolecularly in those cases when the VH and VL domains are expressed by separate single chain antibody constructs, to form a monovalent antigen binding site, such as single chain Fv (scFv) or diabody.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Isolated" refers to a homogenous population of molecules (such as synthetic polynucleotides or a protein such as an antibody) which have been substantially separated and/or purified away from other components of the system the molecules are produced in, such as a recombinant cell, as well as a protein that has been subjected to at least one purification or isolation step. "Isolated antibody" refers to an antibody that is substantially free of other cellular material and/or chemicals and encompasses antibodies that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Antibodies" include antibodies generated using various technologies, including antibodies generated from immunized animals such as mice, rats, alpacas, rabbits or chickens, or identified from phage or mammalian display libraries.

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Human antibody" refers to an antibody that is optimized to have minimal immune response when administered to a human subject. Variable regions of human antibody are derived from human germline immunoglobulin sequences. If the antibody contains a constant region or a portion of the constant region, the constant region is also derived from human germline immunoglobulin sequences.

Human antibody comprises heavy or light chain variable regions that are "derived from" human germline immunoglobulin sequences if the variable regions of the antibody are obtained from a system that uses human germline immunoglobulin genes. Such exemplary systems are human immunoglobulin gene libraries displayed on phage or mammalian cells, and transgenic non-human animals such as mice, rats or chickens carrying human immunoglobulin loci. "Human antibody" typically contains amino acid differences when compared to the immunoglobulins expressed in humans due to differences between the systems used to obtain the antibody and human immunoglobulin loci, introduction of naturally occurring somatic mutations, intentional introduction of substitutions into the framework or CDRs. "Human antibody" is typically 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin sequences. In some cases, "human antibody" may contain consensus framework sequences derived from human framework sequence analyses, for example as described in (Knappik et al. (2000) J Mol Biol 296: 57-86), or synthetic HCDR3 incorporated into human immunoglobulin gene libraries displayed on phage, for example as described in (Shi et al. (2010) J Mol Biol 397: 385-96), and in Int. Patent Publ. No. WO2009/085462. Antibodies in which CDRs are derived from a non-human species are not included in the definition of "human antibody".

"Recombinant" refers to antibodies and other proteins that are prepared, expressed, created or isolated by recombinant means.

"Epitope" refers to a portion of an antigen to which an antibody specifically binds. Epitopes usually consist of chemically active (such as polar, non-polar or hydrophobic) surface groupings of moieties such as amino acids or polysaccharide side chains and may have specific three-dimensional structural characteristics, as well as specific charge characteristics. An epitope may be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Multispecific" refers to a protein, such as an antibody, that specifically binds two or more distinct antigens or two or more distinct epitopes within the same antigen. The multispecific protein may have cross-reactivity to other related antigens, for example to the same antigen from other species (homologs), such as human or monkey, for example *Macaca fascicularis* (cynomolgus, cyno), Pan troglodytes (chimpanzee, chimp) or *Callithrix jacchus* (common marmoset, marmoset), or may bind an epitope that is shared between two or more distinct antigens.

"Bispecific" refers to a protein, such as an antibody, that specifically binds two distinct antigens or two distinct epitopes within the same antigen. The bispecific protein may have cross-reactivity to other related antigens, for example to the same antigen from other species (homologs), such as human or monkey, for example *Macaca fascicularis* (cynomolgus, cyno), Pan troglodytes (chimpanzee, chimp) or *Callithrix jacchus* (common marmoset, marmoset), or may bind an epitope that is shared between two or more distinct antigens.

"Specifically binds," "specific binding" or "binds" refers to antibody binding to an antigen or an epitope within the antigen with greater affinity than for other antigens or epitopes. Typically, the antibody binds to the antigen or the epitope within the antigen with an equilibrium dissociation constant ($K_D$) of $1 \times 10^{-7}$ M or less, for example $1 \times 10^{-8}$ M or less, $1 \times 10^{-9}$ M or less, $1 \times 10^{-10}$ M or less, $1 \times 10^{-11}$ M or less, or $1 \times 10^{-12}$ M or less, typically with a $K_D$ that is at least one hundred-fold less than its $K_D$ for binding to a non-specific antigen (e.g., BSA, casein). The $K_D$ may be measured using standard procedures. Antibodies that specifically bind to the antigen or the epitope within the antigen may, however, have cross-reactivity to other related antigens, for example to the same antigen from other species (homologs), such as human or monkey, for example *Macaca fascicularis* (cynomolgus, cyno), Pan troglodytes (chimpanzee, chimp) or *Callithrix jacchus* (common marmoset, marmoset). While a monospecific antibody specifically binds one antigen or one epitope, a bispecific antibody specifically binds two distinct antigens or two distinct epitopes.

Key advantages for this approach include, but are not limited to: (1) reducing test complexity and the number of steps required by the end user (2) reduced packaging complexity and number of accessories that must be included as part of the assay kit (e.g., no need for a separate tube to perform lysis steps and no need to include a transfer pipet) and (3) preserving more target analyte for the test as such is not unnecessarily diluted by performing lysis steps in a separate tube. That is, the target analyte may be kept more concentrated (and hence, may potentially give a stronger signal) as the swab no longer needs to be placed in excess volume in order have sufficient material to transfer and perform the lateral flow immunoassay.

Referring now to FIGS. 1-6, the lateral flow assay may be of typical construction known in the art, including lateral flow assay cassette 1, which may include an outer housing 27, a sample pad 25, a conjugate pad, membrane and an absorbent (or 'wicking') pad. The membrane may be visible through a result display window 19. The outer housing 27 may be typically made of a plastic suitable for use in lateral flow immunoassays (e.g., HIPS, ABS, etc.). The disclosed designs, in contrast, specifically hold the swab head 9 of the swab either directly in contact with the rapid test sample pad 25 or directly above the sample pad 25. The cassette 1 may further include a sample port 13 located above the sample pad 25 to allow the swab head 9 to be placed directly in contract with sample pad 25 or directly above the sample pad 25.

The cassette 1 may further include a result display window 19, which allows one or more result indicators to be viewed. In some embodiments, the result indicators may be include lines. In the exemplary embodiments of FIG. 5-10, the result display window 19 may display a control line 15, which indicates that the assay is working as expected, as well as a test line 17, which indicates a result, such as a positive or negative result. In some embodiments, the control line 15, may correspond to a portion of the membrane that reacts with a control component of the assay, such as an antibody bound to an antigen, to form a visible indicator.

The cassette 1 may include other features to facilitate its use, such as a unique identifier. The tracking identifier may be a bar code or other computer readable identifier, or a simple location to write a tracking number or paste a label with the tracking number, such as ID line 21.

Figure 2:
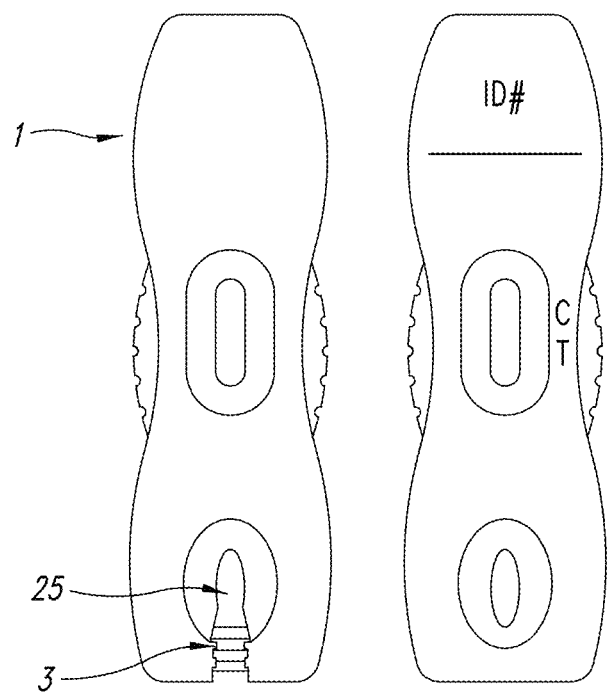
FIG. 2 is a schematic diagram of an overhead views of an exemplary cassette 1 comprising a "grabber" style swab holder 3 (left cassette) and a standard cassette for indirect sample application (right cassette).
Figure 3:
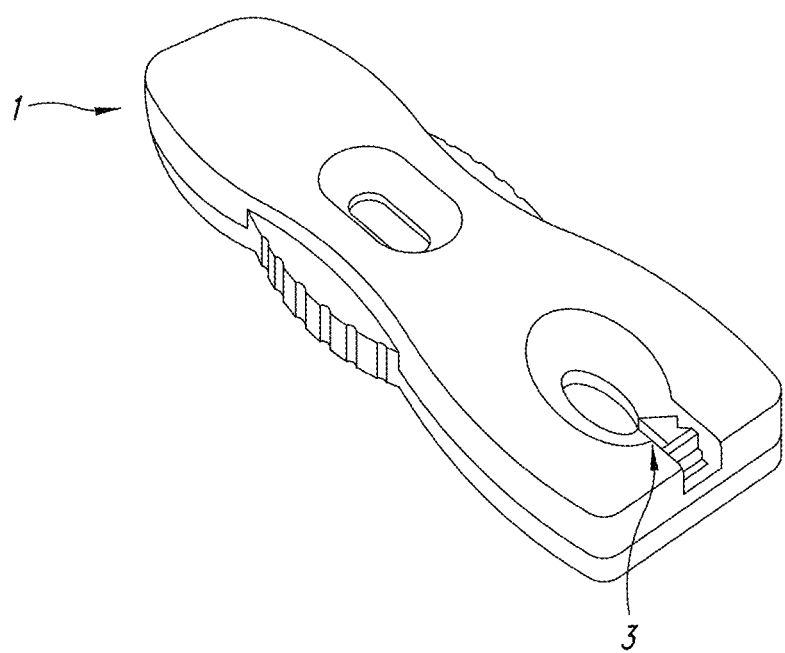
FIG. 3 a schematic diagram of a top and side view of an exemplary cassette 1 comprising a "grabber" style swab holder 3.

An exemplary cassette 1 comprising a swab holder 3 is shown in FIG. 2, along with a standard cassette for conventional indirect sample application. Other views of an exemplary cassette 1 comprising a swab holder 3 are shown in FIGS. 3 and 4. The cassette is designed to include protrusions 5 in the form of small 'pegs' to grab a swab of a specific dimension (FIG. 1A and FIG. 3) or with a 'featherboard' 7 to securely hold swabs of varying dimension (FIG. 1B, FIG. 4, FIG. 5, FIG. 6).

A variety of types of sample collection swabs are known in the art. Any appropriate swab may be used. Swabs that may be suitable for use include, but are not limited to, nasal, nasopharyngeal, mid-turbinate, and saliva/sputum/oropharyngeal swab types. Swabs typically include a swab head 9 attached to a swab stem 11.

Preferably, the swab head 9 is formed of a material to which the desired analyte does not adsorb. In some embodiments, the swab head 9 is formed of polyester, spun polyester, or another suitable material that ensures for the thorough release of the target analyte. In some embodiments, a swab stem 11 has a diameter ranging from 1 mm to 3 mm. The swab holder 3 may be sized to secure a swab having a larger or smaller stem, as desired. The swab holder 3 may take any form that allows for a swab to be securely held in place such that routine handling does not dislodge the swab head.

In certain embodiments, the swab holder 3 is a "grabber", which comprises protrusions 5 that secure swab stems of a specific diameter.

Figure 4A:
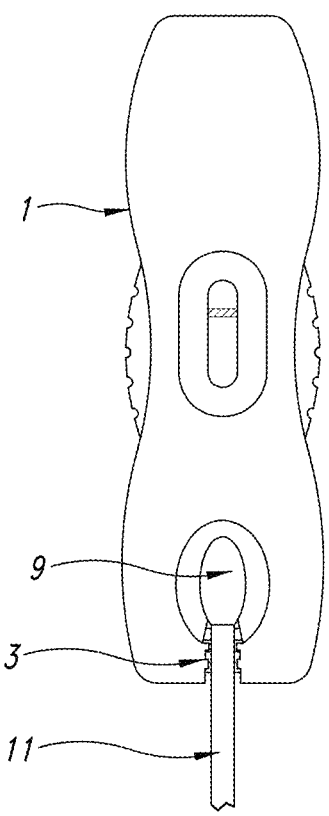
FIGS. 4A and 4B are schematic diagrams of cassettes 1 comprising "featherboard" style swab holders 3.
Figure 4B:
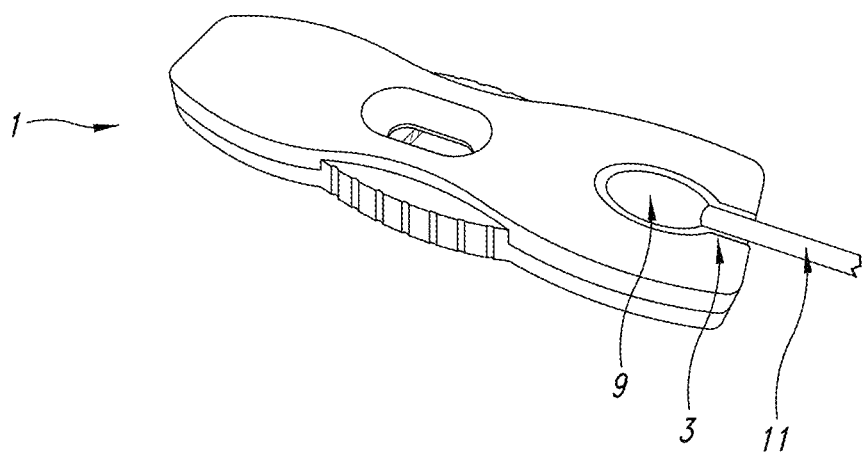
Figure 5:
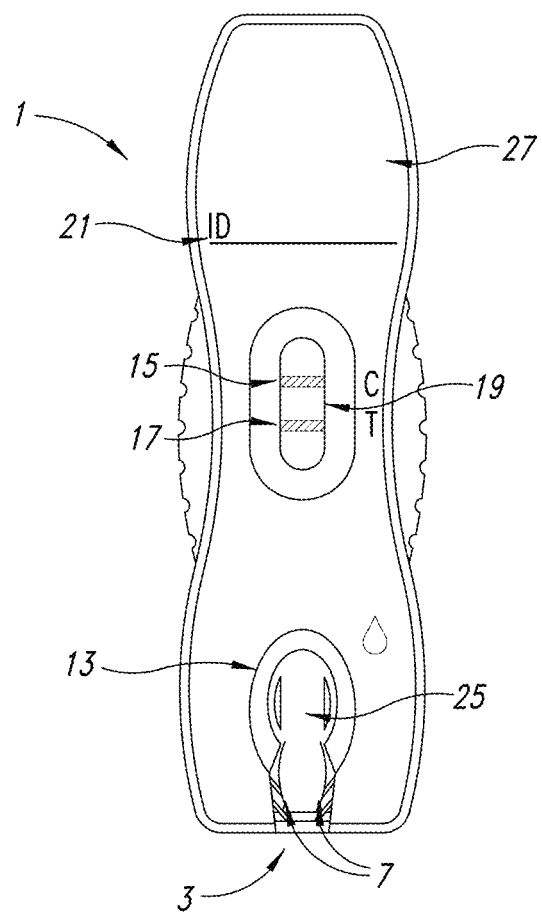
FIG. 5 is a schematic diagram of a top view of an exemplary cassette 1 that may particularly be used to detect SARS-CoV-2.

In certain embodiments, the swab holder 3 is a "featherboard" 7, which comprises a plurality of flexible protrusions that can secure swab stems of a variety of sizes. FIG. 4A shows an overhead view of an exemplary cassette 1 with a "featherboard" 7 swab holder 3, showing placement of a swab in the swab holder 3 with the swab stem 11 secured in the swab holder 3, positioning the swab head 9 over the sample pad (not visible). FIG. 4B shows another view of an exemplary cassette 1 with a "featherboard" 7 swab holder 3, showing placement of a swab in the swab holder 3 with the swab stem 11 secured in the swab holder 3, positioning the swab head 9 over the sample pad (not visible). In the case of the featherboard 7 swab holder 3, the flexible protrusions are capable of being bent upon insertion of a swab stem 11 with ordinary manual force, and the spring-like force from the flexible protrusions provides sufficient friction to hold swab stems of a variety of sizes.

In some embodiments, such as that shown in FIG. 1B, FIG. 4A, FIG. 4B, FIG. 5, and FIG. 6, there may be the same number of flexible protrusions on both sides of the swab holder 3, or, in other embodiments (not shown), they may be different numbers of the flexible protrusions in different sides of the swab holder 3. In some embodiments, such as that shown in FIG. 1B, FIG. 4A, FIG. 4B, FIG. 5, and FIG. 6, the flexible protrusions may be spaced directly opposite one another in swab holder 3, but in other embodiments (not shown), the protrusions may be placed in a staggered pattern. The featherboard 7 may, in some embodiments, contain at least 2 flexible protrusions, at least 4 flexible protrusion, at least 6 flexible protrusions, between 2 and 10 flexible protrusions, between 4 and 10 flexible protrusions, and between 6 and 10 flexible protrusions in total or per side.

In a preferred embodiment, the protrusions comprise the same material as the main body of the cassette, which allows for simpler and more cost-effective manufacture.

The cassette 1 comprises a sample port 13 that allows access to the sample pad 25. The swab holder 3 secures the swab in a position that allows the swab head 9 to rest within the sample port 13, directly over the sample pad. In some embodiments, the swab holder 3 secures the swab in a position that allows the swab head 9 to rest directly over and in contact with the sample pad. The sample port 13 may be sized to accommodate a swab head 9 of any desired size. Similarly, the protrusions 5 or featherboard 7 may be sized to accommodate any size swab stem 11. Both the grabber style and featherboard style swab holders secure the swab stem via friction. Both the protrusions 5 and the featherboard 7 may be sized to secure swab stems of any diameter from 1 to 3 mm.

Working cassettes have been developed with 3D printers—permitting iterations of the design to ensure the plastic housing works as desired. In a preferred embodiment, the cassette is engineered using 3D CAD design, access to 3D printers, and takes into account the principles of lateral flow immunoassay and sample type processing steps.

A lateral flow assay cassette as provided herein may be used for detection of any analyte that may be present in a sample obtained using a swab. In some embodiments, the analyte is RNA, DNA, or protein. In some embodiments, analytes may be indicative of the presence of an infectious agent, including a virus, bacteria, or fungus. Exemplary infectious agents include, but are not limited to respiratory viruses such as coronavirus, including, SARS-CoV-2, influenza, and RSV, as well as gastrointestinal viruses. Other exemplary infectious agents include respiratory, gastrointestinal, and skin bacteria or fungi, such as tuberculosis, *S. aureus*, such as MRSA, and yeast. Specific exemplary infectious agents include, Human coronavirus, 229E; Human coronavirus, OC43; Human coronavirus, NL63; MERS-coronavirus; SARS-CoV-2; Adenovirus 21; Human Metapneumovirus (hMPV); Parainfluenza virus 1; Parainfluenza virus 2; Parainfluenza virus 3; Parainfluenza virus 4a; Influenza A; Influenza B; Enterovirus D68; Respiratory syncytial virus; Rhinovirus 40; *Haemophilus* influenza; *Streptococcus pneumonia; Streptococcus pyogenes; Candida albicans; Bordetella pertussis; Mycoplasma* pneumonia; *Chlamydia* pneumonia; *Legionella pneumophila*; and *Staphylococcus aureus*.

It will be appreciated that the sample type and the location from which the swab sample is obtained will vary depending on the infectious agent to be detected. Although nasal swab specimens are used in many of the exemplary embodiments herein, the specimen may be any biological tissue, a portion of which may be collected on a swab. The biological tissue may be collected directly from its source onto the swab, or it may be removed from its source and prepared or treated in any manner prior to collection on the swab. Biological secretions or emissions, such as nasal or ear secretions, sputum, saliva, vaginal secretions, pus, blood, urine, or feces may be collected on a swab. Example biological locations that may be swabbed directly include the nose, nasopharyngeal cavity, the oropharyngeal cavity, the mid-turbinate region, mouth, tongue, throat, teeth, gums, tonsils, outer ear canal, skin, wounds, lesions, urethra, vagina, cervix, anus, or rectum. For some assays, particularly those looking for environmental contamination, the sample may be taken from an inanimate object, such as an environmental surface, or it may constitute a sample deposited from the air. Specimens, such as secretions or emissions, from all of these locations may also be obtained and then placed on a swab, as may specimens obtained through more invasive procedures, such a bronchoalveolar lavage samples, or surgical procedures.

In example embodiments, the swab may be sterile prior to specimen collection. The swab head may be made of any of a variety of materials, provide that the material is suitable for collecting the specimen and preserving it sufficiently to be used in the intended assay. For example, the swab head may be cotton. Similarly, the swab stem may be made of any durable material, such as paper, cardboard, wood, or plastic.

Collection of the specimen on the swab may be in any setting, including a hospital setting, a clinical setting, a field setting, or an at-home setting. The assay may be conducted within 0 minutes, 1 minute, 2 minutes, 5 minutes, 10 minutes, 30 minutes, 1 hour, 2 hours, 4 hours, 6 hours, 8 hours, 12 hours, 1 day, 3 days, 2 days, 4 days, 5 days, 1 week, or 1 month of collecting the specimen on the swab. The swab may be stored in appropriate conditions to maintain sample integrity. For example, the swab may be placed in a protective container, such as a glass, plastic, paper, or cardboard container or holder. As another example, the swab may be refrigerated. The swab may also be placed in or treated with any of a number of buffers, preservatives, lysis agents, and other agents or materials able to preserve sample integrity until the assay may be conducted.

Referring now to an assay performed as in FIGS. 5-8, the cassette 1 may be labeled with a unique identifier, for example on ID line 21, or it may already be labeled with a unique identifier prior to use. In either case, the unique identifier may be associated with a sample source, such as a subject.

The swab head 9 is contacted with the sample source in a manner sufficient to obtain a sample for the assay.

Figure 7A:
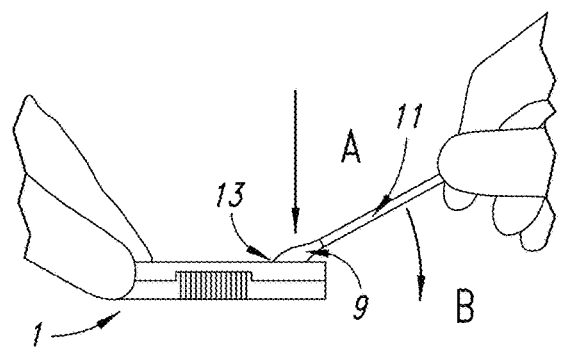
FIG. 7A is a schematic diagram of a lateral view of placing a swab into the exemplary cassette 1 of FIG. 5.

FIG. 7A shows a method of placing a swab in the cassette 1. Specifically, the swab head 9 is place on or above sample port 13 as indicated by arrow A. Then swab stem 11 is maneuvered into swab bolder 3 (not shown) by moving the swab stem 11 in direction B.

Figure 7B:
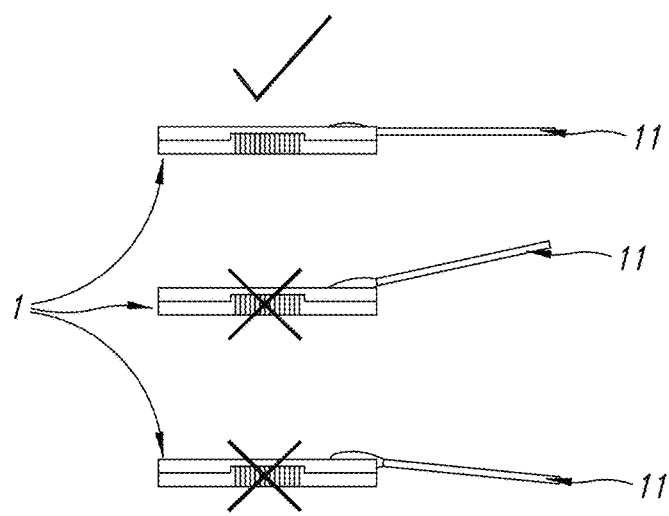
FIG. 7B is a schematic diagram of a lateral view of the correct orientation (upper image) and two incorrect orientations (middle image and lower image) of a swab in the exemplary cassette 1 of FIG. 5.
Figure 7C:
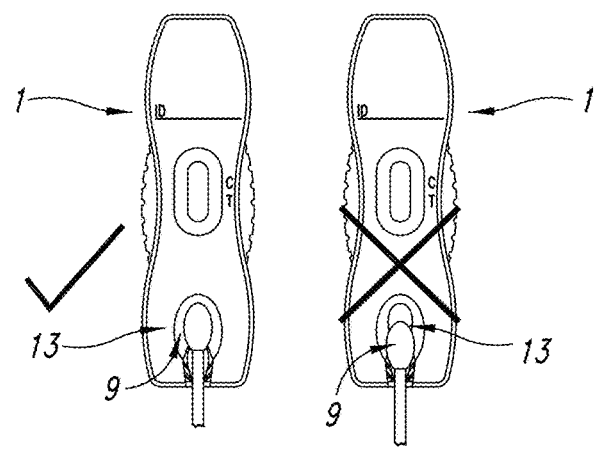
FIG. 7C is a schematic diagram of a top view of the correct orientation (left image) and an incorrect orientation (right image) of a swab in the exemplary cassette 1 of FIG. 5.

FIG. 7B, upper image, shows the correct orientation of swab stem 11 with respect to cassette 1 and FIG. 7C, left image, shows the correct orientation of swab head 9 with respect to sample port 13. FIG. 7B, middle image and lower image, and FIG. 7C, right image, show exemplary incorrect orientations.

Figure 8:
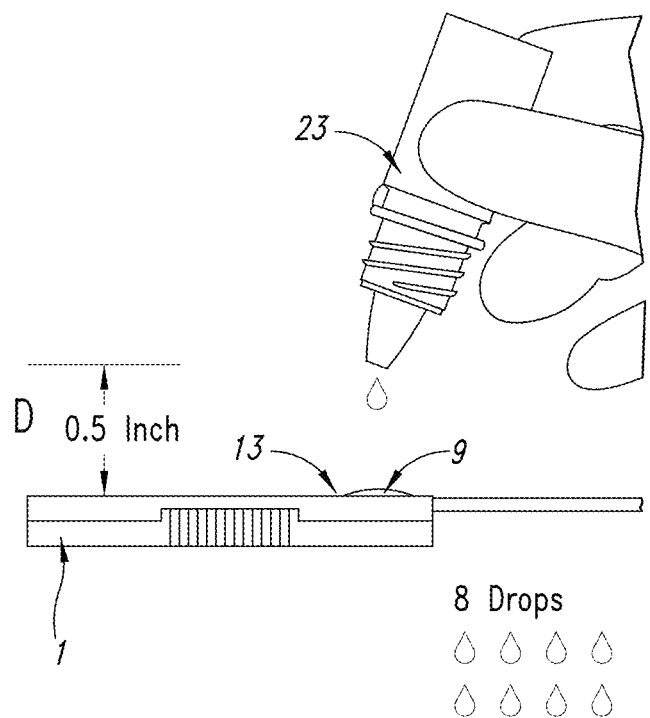
FIG. 8 is a schematic diagram of a lateral view of adding lysis buffer to the exemplary cassette 1 of FIG. 5 after correct placement as shown in FIG. 7B, upper image.

After correct placement of the swab head 9, while the swab is held securely above or directly in contact with the sample port 13, lysis buffer may then be added directly to the swab to release the target analyte onto the sample pad. In an exemplary embodiment, lysis buffer may be dispensed from lysis buffer dropper bottle 23 as shown in FIG. 8 by placing the tip of lysis buffer dropper bottle 23 a distance, D, above the sample port 13 and dropping a set number of drops of the lysis buffer on the swab head 9.

In some embodiments, lysis buffer alone will be sufficient to release and run the entire lateral flow immunoassay. In other embodiments, the lysis buffer may be followed by a chase buffer. A typical lysis buffer may include 1% Triton X-100 or 1-2% Igepal. Chase buffer may include casein or other proteinaceous blocking reagents and/or non-ionic detergents. After the lysis buffer is added directly to the swab head 9, both excess buffer and capillary action will be sufficient to transfer the (now processed) analyte from the swab head 9 onto the sample pad 25 and the rapid test process continues as normal. If chase buffer is desired or required for the assay, the chase buffer may be added to directly to the swab after the lysis buffer, for example in a manner similar to that show in FIG. 8, but with a chase buffer dropper bottle in place of the lysis buffer dropper bottle 23.

Figure 9A:
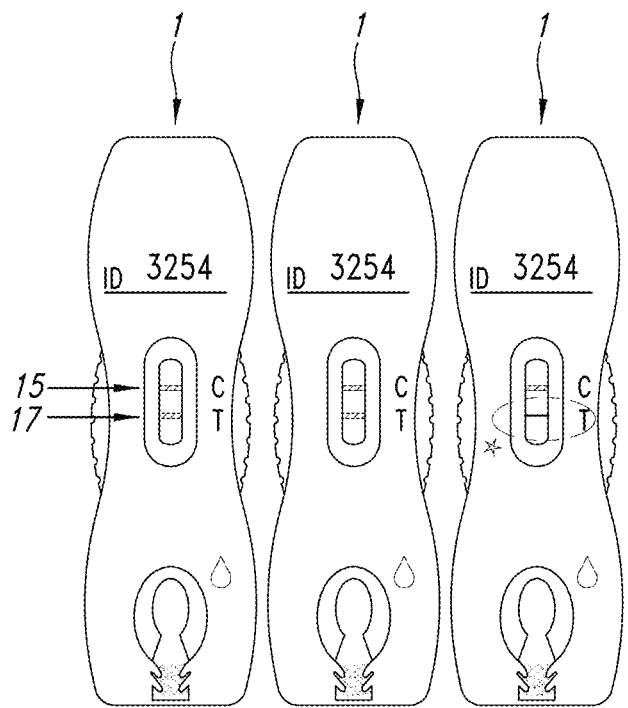
FIG. 9A is a schematic diagram of a top view of three positive test results using the exemplary cassette 1 of FIG. 5.
Figures 9B, 9C:
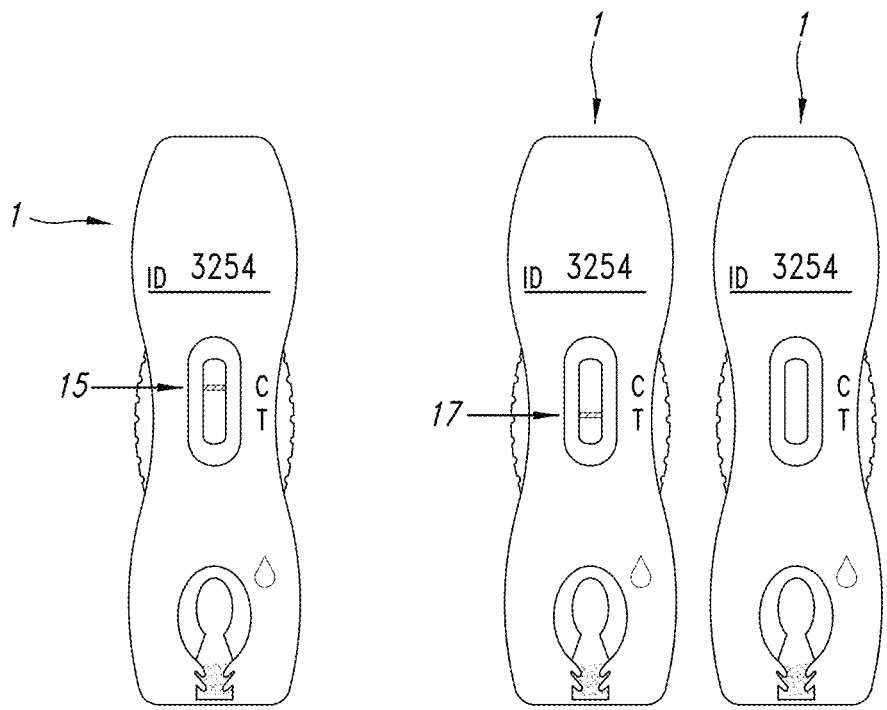
FIG. 9B is a schematic diagram of a top view of a negative test result using the exemplary cassette 1 of FIG. 5.
FIG. 9C is a schematic diagram of a top view of two invalid test results using the exemplary cassette 1 of FIG. 5.

After a period of time sufficient for they assay to be completed, but not so long as to allow results to become inaccurate, results of the assay are viewed in the result display window 19. In the example of FIG. 9A, FIG. 9B, and FIG. 9C, the results include a control line 15, which is visible if the assay functions as expected. As shown in FIG. 9A and FIG. 9B, the control line 15 is visible if the assay functioned as expected. As shown in FIG. 9C, the control line 15 is not visible if the assay did not function as expected, regardless of whether test line 17 is visible. Only assay results in which control line 15 are visible may be considered a positive or negative result. Results in which the control line 15 is not visible are invalid.

As shown in FIG. 9A and FIG. 9B, the result also include a test line 17, which is visible or not visible depending on whether the analyte is present. In the example of FIG. 9A, the test line 17 is visible if the analyte is present. The intensity of the test line may vary depending on the amount of analyte, but any visible test line 17 is indicative of a positive result. In the example of FIG. 9B, the test line 17 is not visible if the analyte is not present, which is indicative of a negative result. Further, in the example of FIG. 9C, the control line 15 is not visible if the assay did not function as expected and regardless of whether test line 17 is visible, such results are invalid.

Results may be read visually by any human with sufficient visual acuity to resolve lines 17 and 15. Results may also be read digitally using a digital camera or other light detector in communication with a processor programmed to recognize and interpret lines 15 and 17 using digital information from the camera. For example, the results may be read digitally using a smartphone, a camera connected to a laboratory computer, or a dedicated reader.

The assays described herein differ from conventional lateral flow assays in several respects. Recently, the Abbot BinaxNOW™ COVID-19 Ag Card (fda.gov/media/141570/download) has been reported to include a specific swab type placed into a heavy weight card stock that has two holes—one for the swab entry and one for adding lysis buffer. In this approach, an extraction buffer is first added to a top hole/well in the card. The user then must insert the swab into the bottom hole and push upwards until the swab is visible in the top hole. The user must rotate the swab and then remove an adhesive layer to close the card upon itself in order to start the assay. Another example of a conventional lateral flow assay is the SD Biosensor Standard Q COVID-19 Ag test (sdbiosensor.com/xe/product/7672), which requires the sample swab to be placed into a tube containing an extraction buffer. After agitating the swab in the extraction buffer, the tube is then squeezed to extract liquid from the swab.

The proposed assay here is distinct relative to conventional lateral flow assays in several ways, including: (1) a swab is placed into the cassette first and then eluted with lysis buffer; (2) a featherboard design or other swab stem holding design may allow for multiple swab sizes to fit into the plastic cartridge; (3) this design may hold the swab with sample directly in contact with or above the sample pad; (4), there is no need for the user to perform the separate or additional steps of lysing a swab sample in a tube or other vessel prior to introducing the sample to the sample pad.

To clarify, in a preferred embodiment the disclosed cassette may be used with the following steps:

1. A swab specimen is collected from the subject.
2. The swab is directly placed onto the lateral flow assay cassette (pressed, secured, and locked in place).
3. Lysis buffer is added directly to the swab head.
4. The assay is then interpreted between 15-25 minutes.

The appropriate amount of lysis buffer may vary depending on the assay to be used and the analyte to be detected. In some embodiments, 160-240 μL of lysis buffer is added. In some embodiments, the assay comprises a further step of adding chase buffer to the swab head.

The appropriate temperature for use of the cassette may vary depending on the assay to be used and the analyte to be detected. In some embodiments, the cassette may be used at room temperature.

In one embodiment, the time to test sample interpretation is similar to the BinaxNOW™ COVID-19 Ag Card, but note that the assay protocol order is different: here the swab is first placed into the cassette and lysis buffer is added directly to the swab head. The present assay does not require additional steps and materials, such as are present in the BinaxNOW™ assay to swirl the swab, remove adhesive and close the test upon itself.

The accuracy of the test depends upon the underlying lateral flow immunoassay performance and the concentration of the analyte that is removed from the swab. In a preferred embodiment, assay results may be understood and processed with a clinician. In another embodiment, assay results may be understood and processed by any person or machine.

In a specific embodiment according to FIGS. 5-9, a SCoV-2 Ag Detect™ Rapid Test is provided. The layout for the SCoV-2 Ag Detect™ Rapid Test is provided in FIG. 5. The entire procedure takes approximately 25 minutes.

The SCoV-2 Ag Detect™ Rapid Test does not differentiate between SARS-CoV and SARS CoV-2. The assay is a single-use lateral flow immunoassay for the qualitative detection of SARS-CoV-2 Nucleoprotein antigen in direct anterior nasal swab specimens. This assay may be used with direct nasal swabs respiratory samples collected without transport media.

The rapid test membrane is pre-coated with anti-Nucleoprotein antibodies on the test line 17 and utilizes a separate control line 15 to assure assay flow and performance. A direct nasal swab specimen is eluted with a lysis buffer solution directly in the cassette sample port 13. Then the eluted sample migrates upward on the membrane to react with the test line 17 and control line 15.

The viral antigens, if present, bind to antibody-labeled gold conjugates as the specimen flows upward. Gold conjugates bound to a viral antigen continue to travel upwards and are captured by the test line 15.

If SARS-CoV-2 Nucleoprotein antigen is present in a subject sample, a red line will appear in the test line 17. A red line at the control line 15 should always appear if the assay is performed correctly. The presence of this red control line 15 verifies that proper flow has occurred, and no failure of the gold conjugate has occurred.

Specimens may be from individuals who are suspected of COVID-19 by their healthcare provider within 5 days of symptom onset or from individuals without symptoms or other epidemiological reasons to suspect COVID-19 when tested twice over two or three days with at least 24 hours and no more than 48 hours between tests. Testing may be performed at laboratories certified under the Clinical Laboratory Improvement Amendments of 1988 (CLIA), 42 U.S.C. § 263a, that meet the requirements to perform moderate, high or waived complexity tests. Testing may also be performed at the Point of Care (POC), i.e., in subject care settings operating under a CLIA Certificate of Waiver, Certificate of Compliance, or Certificate of Accreditation.

The assay detects the SARS-CoV-2 nucleocapsid protein antigen. The antigen is generally detectable in anterior nasal swab specimens during the acute phase of infection. Positive results indicate the presence of the viral antigens.

The sample for this assay may be a nasal swab. The nasal swab may be obtained by washing hands before sample collection. The swab may be removed from packaging, being careful not to touch the swab tip (soft end) with the hand. The swab is then carefully inserted at least 1 cm (0.5 inch) inside the nostril of the subject. The swab is slowly rotated using medium pressure at least four times, rubbing it along the insides of nostril for 15 seconds. The swab tip should be touching the inside wall of the nostril through each rotation. Using the same swab, sample collection may be repeated in the other nostril.

Specimens may be tested immediately after collection for optimal test performance. Swab should not be placed into transport media. If storage is needed for transportation, a sterile plastic tube with cap and without any transport media may be used. Samples are stable for up to 4 hours at room temperature and up to 4 days at 2-8° C.

A cassette 1 is placed horizontally on a flat surface. A unique identifier is added to ID line 21 and associated in records with the subject.

Figure 6:
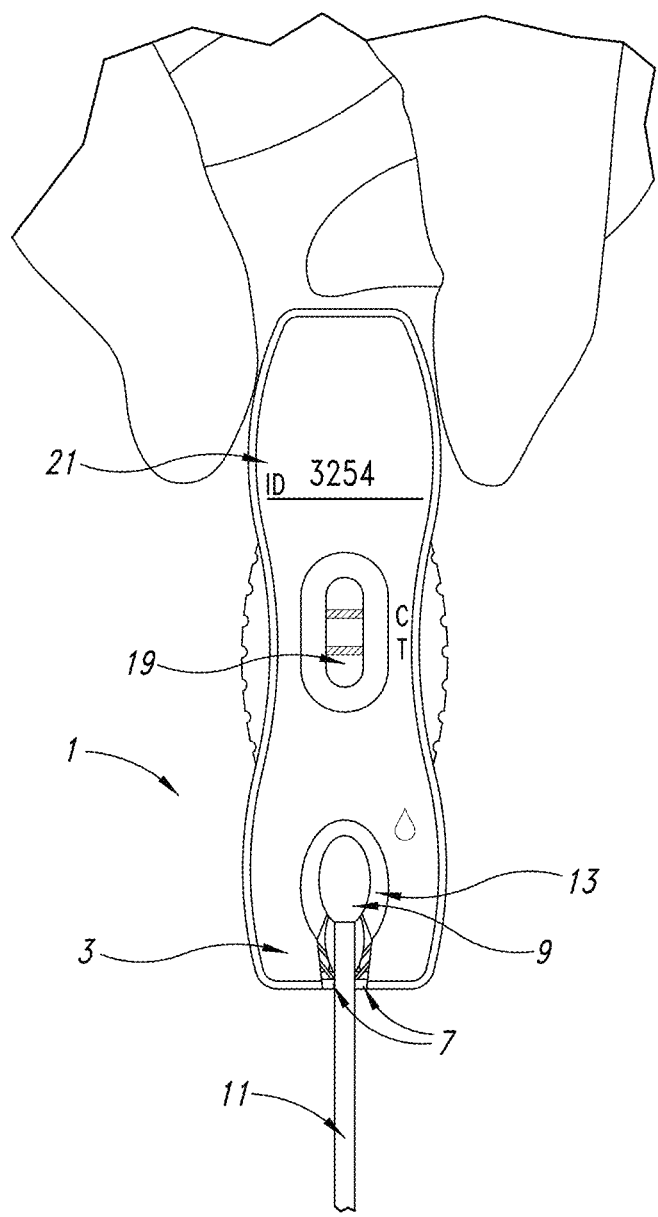
FIG. 6 is a schematic diagram of a top view of an exemplary cassette 1 of FIG. 5 with a swab inserted.

The cassette top end is held firmly with one hand, as shown in FIG. 6. The swab head 9 of the nasal swab specimen is placed directly into the sample port 13 as shown in FIG. 6 and FIG. 7A, arrow A. The swab head 9 of the nasal swab should touch the sample pad 25 at the bottom of the sample port 13. While still holding the cassette 1, the swab head 9 is firmly pushed into the sample port 13 while pressing the swab shaft 11 downwards as shown in FIG. 7A, arrow B. The swab shaft 11 is pressed until it is secured in the swab holder 3. The nasal swab head 9 should be touching the sample pad 25, as shown in FIG. 7B, upper image and FIG. 7C, left image. Incorrect orientations, such as shown in FIG. 7B, middle image and lower image, and FIG. 7C, right image, should be corrected. Incomplete coverage of the sample pad 25 may produce a false negative result.

As shown in FIG. 8, lysis buffer in lysis buffer dropper bottle 23 may be applied by holding the lysis buffer dropper bottle vertically a distance D, of 0.5 inches above the sample port 13.

A set amount of lysis buffer may be slowly added in top of the swab head 9 one drop at a time. Adding less than the set amount of lysis buffer may produce inaccurate results. In one embodiment, 8 drops of lysis buffer may be added. The tip of the lysis buffer dropper bottle 23 may not be touched to the swab head 9 while the lysis buffer is being dispensed.

The cassette 1 may be left undisturbed for a period of time between twenty and 25 minutes after beginning application of the lysis buffer. Test results interpreted after 25 minutes may be inaccurate.

Test results may be interpreted by visual inspection, preferably in a well-lit area. Example positive results are shown in FIG. 9A. Specifically, the test has detected SARS-CoV-2 Nucleoprotein antigen when both the control line ("C") 15 and a test line ("T") 17 appear in the result display window 19 on the test cassette. Even a faint pink link, such as indicated by the circled test line 17 in the right image of FIG. 9A, is considered a positive result.

Example negative results are shown in FIG. 9B. The test is negative when only the control line 15 appears on in the result display window 19 of the cassette 1. A negative result indicates that the SCoV-2 Ag Detect™ Rapid Test did not detect SARS-CoV-2 Nucleoprotein antigen.

The test is invalid if no control line 15 appears on the test cassette, regardless of whether a test line 17 is seen. Example invalid results are shown in FIG. 9C.

Devices and assays according to the present disclosure may be sold as a kit (e.g., InBios SCoV-2 Ag Detect™). Packaging may include recommended swab types with additional instructions provided in the package insert to make sure the end user is properly taking the sample and performing the test. Tests are often packaged in kits of 25, but bulk packaging options may also be available.

The terms "specimen" and "sample" are used interchangeably in this specification. Similarly, the terms "test" and "assay" are used interchangeably.

Elements of the different embodiments disclosed herein, including those in the Examples, may be combined with one another, Furthermore, not all aspects described in connection with a given embodiment are required for that embodiment to function and many aspects are provided merely as details to assist in implementing the disclosure.

EXAMPLES

Example 1: Comparative Assay

Figure 10:
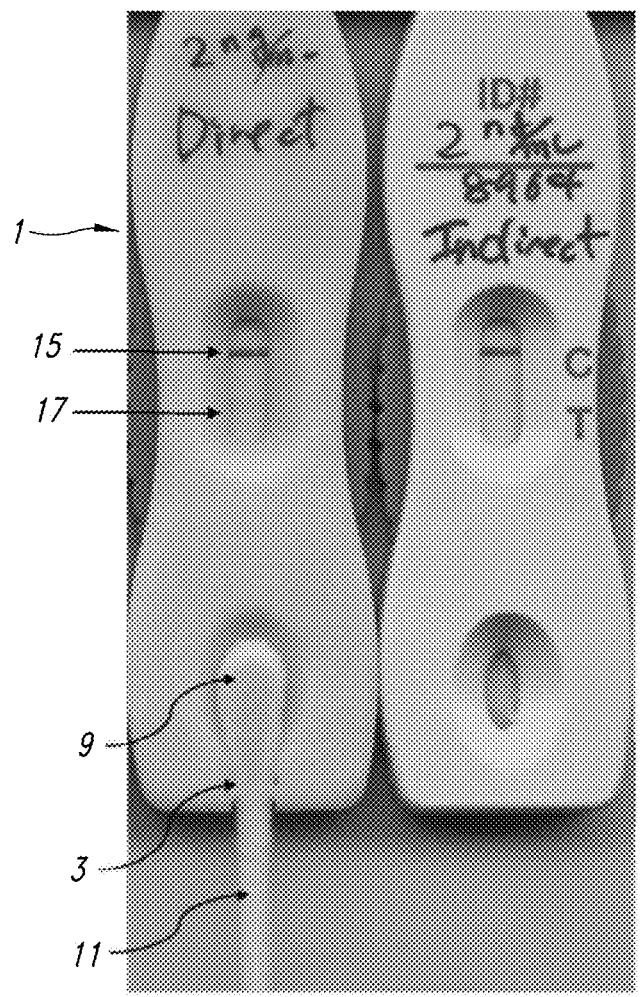
FIG. 10 is a photogram of a top view of a comparison of results obtained using an exemplary cassette 1 with a swab holder 3 (left cassette) and a standard cassette that is not according to the present invention and that uses a conventional indirect sample application method (right cassette).

FIG. 10 shows an example test using a simple antigen capture target system (anthrax lethal factor—LF). Here, 50 µL of a 2 ng/mL LF solution was loaded onto the swab head of each of two Steripack swabs. One swab was loaded directly onto the left cassette of the type shown in FIGS. 1, 3 and 4 and FIG. 2, left panel, followed by 6 drops of lysis buffer. The other swab was placed into a separate lysis buffer tube containing 350 µL with 100 µL of volume then loaded onto the sample port of a conventional cassette as shows on the right in FIG. 2 and X. In this case, the sample was at the lower edge of the limit of detection. As can be seen in FIG. 10, the conventional, indirect format (right cassette) shows a lower signal than the direct swab application using a cassette according to the present disclosure (left cassette). The weaker signal in the indirect sample application cassette may be due to the dilution of analyte by the greater volume of lysis buffer required as compared to the direct swab application process.

Example 2: SCoV-2 Ag Detect™ Rapid Test Kit Testing

The SCoV-2 Ag Detect™ Rapid Test Kit as described herein and illustrated in FIGS. 5-9 was evaluated.
Limit of Detection (LoD)—Analytical Sensitivity:

A limit of detection (LoD) study was conducted to determine the lowest concentration of inactivated SARS-CoV-2 virus in nasal swab matrix at which greater than or equal to 95% of all replicates test positive with the SCoV-2 Ag Detect™ Rapid Test.

Gamma-irradiated, SARS-Related Coronavirus 2 (SARS-CoV-2), USA-WA1/2020 isolate was obtained from ATCC via BEI (RD2660, Cat. NR-52287, Lot 70039067). SARS-CoV-2, isolate USA-WA1/2020 (NR-52287) was isolated from an oropharyngeal swab from a patient with a respiratory illness who developed clinical disease (COVID-19) in January 2020 in Washington, USA. NR-52287 was prepared from infected cultured Vero E6 epithelial cell lysate, gamma irradiated (5E+06 RADs) on dry ice, and then sonicated. NR-52287 is supplied at a concentration of 2.8E+06 $TCID_{50}$/mL Pooled nasal swab matrix consisted of nasal swabs taken from individual healthy donors (presumed SARS-CoV-2 negative), which were eluted in 0.5 mL PBS per swab and then pooled. The same negative matrix pool was used to generate all of the contrived samples in this study. Prior to pooling, the eluted nasal swabs in PBS were screened to confirm lack of background reactivity on the SCoV-2 Ag Detect™ Rapid Test. To screen each nasal swab eluted in PBS, 50 µL of each eluted sample was loaded directly onto a sterile swab compatible with the SCoV-2 Ag Detect™ Rapid Test kit so that the liquid was absorbed onto the swab. Each swab was then tested on the SCoV-2 Ag Detect™ Rapid Test following the instructions in the product insert. All testing was conducted at InBios International, Inc.

The gamma-irradiated, SARS-CoV-2 virus stock solution was diluted in negative nasal swab matrix prepared as described above to a concentration of 1E+05 $TCID_{50}$/mL. This preparation was used throughout the study to prepare serial dilutions.

To determine preliminary LoD, 2-fold serial dilutions of SARS-CoV-2 were prepared by spiking gamma-irradiated SARS-CoV-2 virus into pooled, nasal swab matrix. Each dilution was loaded directly onto a sterile swab compatible with the SCoV-2 Ag Detect™ Rapid Test by slowly pipetting 20 µL of the diluted virus stock so that the virus stock was absorbed onto the swab. Each dilution was tested by an unblinded operator in triplicate using the SCoV-2 Ag Detect™ Rapid Test following the product insert. The preliminary LoD was defined as the dilution with the lowest SARS-CoV-2 concentration for which all three replicates tested positive. The preliminary LoD was observed to be 6.3E+03 $TCID_{50}$/mL.

TABLE 1

Preliminary LoD determination

| [SARS-CoV-2] ($TCID_{50}$/mL) | Total number of replicates | Number of positive replicates | Number of negative replicates | Percent positive (%) |
|---|---|---|---|---|
| 1.0E+05 | 3 | 3 | 0 | 100 |
| 5.0E+04 | 3 | 3 | 0 | 100 |
| 2.5E+04 | 3 | 3 | 0 | 100 |
| 1.3E+04 | 3 | 3 | 0 | 100 |
| 6.3E+03 | 3 | 3 | 0 | 100 |
| 3.1E+03 | 3 | 1 | 2 | 33 |
| 0 | 3 | 0 | 3 | 0 |

To confirm LoD, 2-fold serial dilutions of SARS-CoV-2 virus around the preliminary LoD were prepared in pooled, nasal swab matrix by spiking SARS-CoV-2 at the preliminary LoD, along with two bracketing concentrations. Twenty aliquots of each dilution (0.5×, 1×, and 2× preliminary LoD) were prepared. The 60 aliquots were randomized using the 'sample' function in R (version 3.5.2) and blinded by a unblinded operator. A separate blinded operator tested the blinded samples. Following testing, the results were unblinded by two operators not involved in the testing. The final LoD is defined as the lowest concentration of SARS-CoV-2 at which ≥95% of all replicates test positive with the SCoV-2 Ag Detect™ Rapid Test.

Rapid test external controls were run by the blinded operator prior to testing any study samples following product insert. The external controls gave expected results.

The summarized results of the SCoV-2 Ag Detect™ Rapid Test LoD determination are shown in 2. ≥95% of all replicates at 6.3E+03 and 1.3E+04 $TCID_{50}$/mL tested positive with the SCoV-2 Ag Detect™ Rapid Test, highlighted in gray in the table below. Table 2 shows the line data.

TABLE 2

Final LoD determination based on blinded testing

| [SARS-CoV-2] ($TCID_{50}$/mL) | Total number of replicates | Number of positive replicates | Number of negative replicates | % positive |
|---|---|---|---|---|
| 1.3E+04 | 20 | 20 | 0 | 100 |
| 6.3E+03 | 20 | 19 | 1 | 95 |
| 3.1E+03 | 20 | 17 | 3 | 85 |

TABLE 3

Line data for LoD determination

| Sample Type | Replicate | Result |
|---|---|---|
| Above Preliminary LoD (1.3E+04 $TCID_{50}$/mL) | 1 | Positive |
| | 2 | Positive |
| | 3 | Positive |
| | 4 | Positive |
| | 5 | Positive |
| | 6 | Positive |
| | 7 | Positive |
| | 8 | Positive |
| | 9 | Positive |
| | 10 | Positive |
| | 11 | Positive |
| | 12 | Positive |
| | 13 | Positive |
| | 14 | Positive |
| | 15 | Positive |
| | 16 | Positive |
| | 17 | Positive |
| | 18 | Positive |
| | 19 | Positive |
| | 20 | Positive |
| Preliminary LoD (6.3E+03 $TCID_{50}$/mL) | 1 | Positive |
| | 2 | Positive |
| | 3 | Positive |
| | 4 | Positive |
| | 5 | Positive |
| | 6 | Positive |
| | 7 | Positive |
| | 8 | Positive |
| | 9 | Positive |
| | 10 | Positive |
| | 11 | Positive |
| | 12 | Positive |
| | 13 | Positive |
| | 14 | Positive |
| | 15 | Negative |
| | 16 | Positive |
| | 17 | Positive |
| | 18 | Positive |
| | 19 | Positive |
| | 20 | Positive |
| Below Preliminary LoD (3.1E+03 $TCID_{50}$/mL) | 1 | Positive |
| | 2 | Positive |
| | 3 | Positive |
| | 4 | Positive |
| | 5 | Positive |
| | 6 | Negative |
| | 7 | Positive |
| | 8 | Negative |
| | 9 | Positive |
| | 10 | Positive |
| | 11 | Negative |
| | 12 | Positive |
| | 13 | Positive |
| | 14 | Positive |
| | 15 | Positive |
| | 16 | Positive |
| | 17 | Positive |
| | 18 | Positive |
| | 19 | Positive |
| | 20 | Positive |

LoD was determined to be 6.3E+03 $TCID_{50}$/mL, demonstrating ≥95% detection rate.

Cross-reactivity (Analytical Specificity):

The purpose of this study was to assess whether SCoV-2 Ag Detect™ Rapid Test reacts with related pathogens, high prevalence disease agents, and normal or pathogenic microflora that may be present in clinical nasal swab specimens.

The organisms listed in Table 4 were evaluated for cross-reactivity by wet testing with the SCoV-2 Ag Detect™ Rapid Test. Organisms were obtained from BEI Resources (Manassas, Va.) and ZeptoMetrix (Buffalo, N.Y.). The potential cross-reactive organisms were spiked into pooled, negative nasal swab matrix at 1E+06 CFU/mL for bacteria/fungi and 1E+05 $TCID_{50}$/mL or $CEID_{50}$/mL for viruses. OC43 and parainfluenza virus 4a were tested at lower concentrations (8.9E+04 and 1.6E+04 $TCID_{50}$/mL, respectively) because the commercially supplied stocks were less than 1E+05 $TCID_{50}$/mL. These two organisms were tested neat.

Pooled nasal swab matrix consisted of nasal swabs taken from individual healthy donors (presumed SARS-CoV-2 negative), which were eluted in 0.5 mL PBS per swab and then pooled. The same negative matrix pool was used throughout study. Prior to pooling, the eluted nasal swabs in PBS were screened to confirm lack of background reactivity on the SCoV-2 Ag Detect™ Rapid Test. To screen each nasal swab eluted in PBS, 50 μL of each eluted sample was loaded directly onto a sterile swab compatible with the SCoV-2 Ag Detect™ Rapid Test kit so that the liquid was absorbed onto the swab. Each swab was then tested on the SCoV-2 Ag Detect™ Rapid Test following the instructions in the product insert.

Pooled human nasal wash from three unique donors was obtained from Lee Biosolutions Inc. (Maryland Heights, Mo.). The pooled human nasal wash was tested neat and represented the diverse microbial flora present in the human respiratory tract.

Human coronavirus HKU1, SARS-CoV-1, *Mycobacterium tuberculosis*, and *Pneumocystis jirovecii* (PJP) were not available for wet testing. For these pathogens, in silico analysis was performed using NCBI BLAST to determine protein homology between the pathogen and SARS-CoV-2 nucleocapsid protein (NP, the diagnostic target of SCoV-2 Ag Detect™ Rapid Test).

SCoV-2 Ag Detect™ Rapid Tests were performed as per the product insert. All testing was conducted by trained operators at InBios International, Inc. (Seattle, Wash.). Each potential cross-reactive organism was tested in triplicate. If any replicate tested positive, that organism was considered cross-reactive for SCoV-2 Ag Detect™ Rapid Test.

TABLE 4

Potential cross-reactive organisms and test concentrations

| Specimen Type | Source | Catalog # | Test Concentration |
|---|---|---|---|
| Human coronavirus, 229E | BEI | NR-52726 | $TCID_{50}$: 1E+05/mL |
| Human coronavirus, OC43 | BEI | NR-52725 | $TCID_{50}$: 8.9E+04/mL |
| Human coronavirus, NL63 | ZeptoMetrix | 0810228CF | $TCID_{50}$: 1E+05/mL |
| MERS-coronavirus | ZeptoMetrix | 0810575CFHI | $TCID_{50}$: 1E+05/mL |
| Adenovirus 21 | BEI | NR-51436 | $TCID_{50}$: 1E+05/mL |
| Human Metapneumovirus (hMPV) | BEI | NR-22227 | $TCID_{50}$: 1E+05/mL |
| Parainfluenza virus 1 | BEI | NR-48680 | $TCID_{50}$: 1E+05/mL |
| Parainfluenza virus 2 | BEI | NR-3229 | $TCID_{50}$: 1E+05/mL |
| Parainfluenza virus 3 | BEI | NR-3233 | $TCID_{50}$: 1E+05/mL |
| Parainfluenza virus 4a | BEI | NR-3237 | $TCID_{50}$: 1.6E+04/mL |
| Influenza A | BEI | NR-41800 | $TCID_{50}$: 1E+05/mL |
| Influenza B | BEI | NR-44023 | $TCID_{50}$: 1E+05/mL |
| Enterovirus D68 | BEI | NR-51998 | $TCID_{50}$: 1E+05/mL |
| Respiratory syncytial virus | BEI | NR-44231 | $TCID_{50}$: 1E+05/mL |
| Rhinovirus 40 | BEI | NR-51453 | $TCID_{50}$: 1E+05/mL |
| *Haemophilus influenzae* | ZeptoMetrix | 801679 | CFU: 1E+06/mL |
| *Streptococcus pneumoniae* | ZeptoMetrix | 801439 | CFU: 1E+06/mL |
| *Streptococcus pyogenes* | ZeptoMetrix | 801512 | CFU: 1E+06/mL |
| *Candida albicans* | ZeptoMetrix | 801504 | CFU: 1E+06/mL |
| *Bordetella pertussis* | ZeptoMetrix | 801459 | CFU: 1E+06/mL |
| *Mycoplasma pneumoniae* | ZeptoMetrix | 801579 | CFU: 1E+06/mL |
| *Chlamydia pneumoniae* | ZeptoMetrix | 804392 | CFU: 1E+06/mL |
| *Legionella pneumophila* | ZeptoMetrix | 801645 | CFU: 1E+06/mL |
| *Staphylococcus aureus* | ZeptoMetrix | 801638 | CFU: 1E+06/mL |
| *Staphylococcus epidermidis* | ZeptoMetrix | 801651 | CFU: 1E+06/mL |
| Pooled human nasal wash | Lee Biosolutions | 991-26-S | Neat |

Rapid test external controls were run by the operators prior to testing any study samples and gave expected results. The line data for testing performed with the SCoV-2 Ag Detect™ Rapid Test are shown in Table 5.

No cross-reactivity was observed with the SCoV-2 Ag Detect™ Rapid Test for samples that contained pathogens associated with high prevalence disease agents and other respiratory diseases, or with pooled human nasal wash.

TABLE 5

Line data for cross-reactivity (analytical specificity) study

| Specimen Type | Replicate #1 | Replicate #2 | Replicate #3 |
|---|---|---|---|
| Human coronavirus, 229E | Negative | Negative | Negative |
| Human coronavirus, OC43 | Negative | Negative | Negative |
| Human coronavirus, NL63 | Negative | Negative | Negative |
| MERS-coronavirus | Negative | Negative | Negative |
| Adenovirus 21 | Negative | Negative | Negative |
| Human Metapneumovirus (hMPV) | Negative | Negative | Negative |
| Parainfluenza virus 1 | Negative | Negative | Negative |
| Parainfluenza virus 2 | Negative | Negative | Negative |
| Parainfluenza virus 3 | Negative | Negative | Negative |
| Parainfluenza virus 4a | Negative | Negative | Negative |
| Influenza A | Negative | Negative | Negative |
| Influenza B | Negative | Negative | Negative |
| Enterovirus D68 | Negative | Negative | Negative |
| Respiratory syncytial virus (RSV) | Negative | Negative | Negative |
| Rhinovirus | Negative | Negative | Negative |
| *Haemophilus influenzae* | Negative | Negative | Negative |
| *Streptococcus pneumoniae* | Negative | Negative | Negative |
| *Streptococcus pyogenes* | Negative | Negative | Negative |
| *Candida albicans* | Negative | Negative | Negative |
| *Bordetella pertussis* | Negative | Negative | Negative |
| *Mycoplasma pneumoniae* | Negative | Negative | Negative |
| *Chlamydia pneumoniae* | Negative | Negative | Negative |
| *Legionella pneumophila* | Negative | Negative | Negative |
| *Staphylococcus aureus* | Negative | Negative | Negative |
| *Staphylococcus epidermidis* | Negative | Negative | Negative |
| Pooled human nasal wash | Negative | Negative | Negative |

The following pathogens were analyzed in silico for sequence homology via NCBI's BLAST, because they were not available for wet testing.

Human coronavirus HKU1
SARS-CoV-1
*Mycobacterium tuberculosis*
*Pneumocystis jirovecii* (PJP)

The nucleocapsid protein (NP) of human coronavirus HKU1 was determined to have 34% homology with SARS-CoV-2 NP, suggesting a low probability of cross-reactivity. The NP protein of SARS-CoV-1 was determined to have 91% homology with SARS-CoV-2 NP, suggesting cross-reactivity may occur. BLASTs of the *Mycobacterium tuberculosis* and *Pneumocystis jirovecii* (PJP) proteomes found no homology, indicating a low probability of cross-reactivity.

The SCoV-2 Ag Detect™ Rapid Test showed no cross-reactivity against samples spiked with other coronaviruses, other respiratory infections which may present with similar symptoms as SARS-CoV-2, or with pooled human nasal wash. SARS-CoV-1 was predicted to be cross-reactive based on protein sequence homology.

Microbial Interference Studies

The purpose of this study was to evaluate whether co-infection with human coronaviruses, high prevalence disease agents, and normal or pathogenic flora will interfere with detection of SARS-CoV-2 (i.e. result in false negatives) by the SCoV-2 Ag Detect™ Rapid Test.

The organisms listed in 4 were also evaluated for interference with detection of SARS-CoV-2 by the SCoV-2 Ag Detect™ Rapid Test. Organisms were obtained from BEI Resources (Manassas, Va.) and ZeptoMetrix (Buffalo, N.Y.). The potential interfering organisms were spiked into pooled nasal swab matrix at final concentration of 1E+06 CFU/mL for bacteria/fungi and 1E+05 $TCID_{50}$/mL or $CEID_{50}$/mL for viruses. OC43 and parainfluenza virus 4a were tested at lower concentrations (8.9E+04 and 1.6E+04 $TCID_{50}$/mL, respectively) because the commercially supplied stocks were less than 1E+05 $TCID_{50}$/mL. These two organisms were tested neat.

Pooled nasal swab matrix consisted of nasal swabs taken from individual healthy donors (presumed SARS-CoV-2 negative), which were eluted in 0.5 mL PBS per swab and then pooled. The same negative matrix pool was used throughout study. Prior to pooling, the eluted nasal swabs in PBS were screened to confirm lack of background reactivity on the SCoV-2 Ag Detect™ Rapid Test. To screen each nasal swab eluted in PBS, 50 µL of each eluted sample was loaded directly onto a sterile swab compatible with the SCoV-2 Ag Detect™ Rapid Test kit so that the liquid was absorbed onto the swab. Each swab was then tested on the SCoV-2 Ag Detect™ Rapid Test following the instructions in the product insert.

Pooled human nasal wash from three unique donors was obtained from Lee Biosolutions Inc. (Maryland Heights, Mo.). The pooled human nasal wash was tested neat and represented the diverse microbial flora present in the human respiratory tract.

Gamma-irradiated SARS-CoV-2 virus, USA-WA1/2020 isolate, was obtained from ATCC via BEI (RD2660, Cat. NR-52287, Lot 70039067). NR-52287 is a strain of SARS-CoV-2, which was prepared from infected cultured Vero E6 epithelial cell lysate, gamma irradiated (5E+06 RADs) on dry ice, and then sonicated. NR-52287 is supplied at a concentration of 2.8E+06 $TCID_{50}$/mL.

For the microbial interference study, the SARS-CoV-2 stock solution was diluted in pooled, negative nasal swab matrix to 2.06E+05 $TCID_{50}$/mL. Then SARS-CoV-2 stock solution in pooled, negative nasal matrix was mixed with each interfering microorganism at corresponding supporting dilutions or neat pooled nasal wash, then loaded onto swabs by slowly pipetting for testing, to yield a final concentration of SARS-CoV-2 of 1.88E+04 $TCID_{50}$/mL (3×LoD) and final concentration of 1E+06 CFU/mL for the bacteria/fungi and 1E+05 $TCID_{50}$/mL or $CEID_{50}$/mL for viruses. Samples were spiked at a low SARS-CoV-2 concentration and a high interferent level to represent the worst-case scenario. One operator tested each sample in triplicate.

SCoV-2 Ag Detect™ Rapid Test and kit controls were used throughout the study and were tested as per the product insert. All testing was conducted at InBios International, Inc. (Seattle, Wash.). Each potential interfering organism was tested in triplicate. If any replicate tested negative, that organism was considered interfering with detection of SARS-CoV-2 by the SCoV-2 Ag Detect™ Rapid Test.

Rapid test external controls were run by the operators prior to testing any study samples and gave expected results. The line data for testing performed with the SCoV-2 Ag Detect™ Rapid Test are shown in 6.

TABLE 6

Line data for microbial interference study

| Specimen Type | Replicate #1 | Replicate #2 | Replicate #3 |
|---|---|---|---|
| Human coronavirus, 229E | Positive | Positive | Positive |
| Human coronavirus, OC43 | Positive | Positive | Positive |
| Human coronavirus, NL63 | Positive | Positive | Positive |
| MERS-coronavirus | Positive | Positive | Positive |
| Adenovirus 21 | Positive | Positive | Positive |
| Human Metapneumovirus (hMPV) | Positive | Positive | Positive |
| Parainfluenza virus 1 | Positive | Positive | Positive |
| Parainfluenza virus 2 | Positive | Positive | Positive |
| Parainfluenza virus 3 | Positive | Positive | Positive |

TABLE 6-continued

Line data for microbial interference study

| Specimen Type | Replicate #1 | Replicate #2 | Replicate #3 |
|---|---|---|---|
| Parainfluenza virus 4a | Positive | Positive | Positive |
| Influenza A | Positive | Positive | Positive |
| Influenza B | Positive | Positive | Positive |
| Enterovirus D68 | Positive | Positive | Positive |
| Respiratory syncytial virus (RSV) | Positive | Positive | Positive |
| Rhinovirus | Positive | Positive | Positive |
| Haemophilus influenzae | Positive | Positive | Positive |
| Streptococcus pneumoniae | Positive | Positive | Positive |
| Streptococcus pyogenes | Positive | Positive | Positive |
| Candida albicans | Positive | Positive | Positive |
| Bordetella pertussis | Positive | Positive | Positive |
| Mycoplasma pneumoniae | Positive | Positive | Positive |
| Chlamydia pneumoniae | Positive | Positive | Positive |
| Legionella pneumophila | Positive | Positive | Positive |
| Staphylococcus aureus | Positive | Positive | Positive |
| Staphylococcus epidermidis | Positive | Positive | Positive |
| Pooled human nasal wash | Positive | Positive | Positive |

No interference was observed with the SCoV-2 Ag Detect™ Rapid Test for SARS-CoV-2 samples that also contained pathogens associated with high prevalence disease agents and other respiratory diseases, or with pooled human nasal wash.

The SCoV-2 Ag Detect™ Rapid Test showed no microbial interference from any of the pathogens tested.

Endogenous Interference Substances Studies:

The purpose of this study was to determine the effects of potentially interfering substances on the SCoV-2 Ag Detect™ Rapid Test.

This purpose of this study was to evaluate whether blood components and common nasal treatments have detrimental effects on the SCoV-2 Ag Detect™ Rapid Test. Potentially interfering substances tested in this study are listed in 7.

TABLE 7

Substances tested for interference study

| Substance | Active Ingredient | Tested concentration | Solvent |
|---|---|---|---|
| Whole Blood | N/A | 4% | N/A |
| Mucin | Mucin | 0.5% | 0.1N NaOH |
| Chloraseptic/Cepacol | Benzocaine | 1.5 mg/mL | Ethanol |
| NeilMed NasoGEL | Sodium Chloride, Sodium Bicarbonate | 5% v/v | N/A |
| CVS Nasal Drops | Phenylephrine | 15% v/v | N/A |
| Afrin | Oxymetazoline | 15% v/v | N/A |
| Nasal Spray | Cromolyn | 15% v/v | N/A |
| Zicam Cold Remedy | Zincum aceticum, Zincum gluconicum | 5% v/v | N/A |
| Alkalol Homeopathic | Menthol, Eucalyptol | 1:10 dilution | N/A |
| Sore Throat Phenol Spray | Phenol | 15% v/v | N/A |
| Tobramycin | Tobramycin | 4 µg/mL | N/A |
| Mupirocin | Mupirocin | 10 mg/mL | DMSO |
| Flonase Nasal Spray | Fluticasone Propionate | 5% v/v | N/A |
| Tamiflu | Oseltamivir phosphate | 5 mg/mL | Ethanol |

Gamma-irradiated SARS-CoV-2 virus isolate was obtained from ATCC via BEI (RD2660, Cat. NR-52287, Lot 70039067). For this study, the SARS-CoV-2 stock solution was diluted in negative nasal swab matrix to 2.06E+05 $TCID_{50}$/mL.

The interfering substances were mixed either with SARS-CoV-2 stock solution in pooled negative nasal matrix, to yield a final concentration of SARS-CoV-2 of 1.88E+04

TCID$_{50}$/mL (3×LoD), or with negative pooled nasal matrix. Then the interfering substances in SARS-CoV-2 positive or negative nasal matrices were loaded onto swabs by slowly pipetting for testing. One operator tested the samples in triplicate.

Pooled nasal swab matrix consisted of nasal swabs taken from individual healthy donors (presumed SARS-CoV-2 negative), which were eluted in 0.5 mL PBS per swab and then pooled. The same negative matrix pool was used throughout study. Prior to pooling, the eluted nasal swabs in PBS were screened to confirm lack of background reactivity on the SCoV-2 Ag Detect™ Rapid Test. To screen each nasal swab eluted in PBS, 50 µL of each eluted sample was loaded directly onto a sterile swab compatible with the SCoV-2 Ag Detect™ Rapid Test kit so that the liquid was absorbed onto the swab. Each swab was then tested on the SCoV-2 Ag Detect™ Rapid Test following the instructions in the product insert.

If any replicates of the positive or negative samples produced false positive or false negative results with the addition of an interfering substance, then that substance was considered interfering.

Rapid test external controls were run by the operator prior to testing any study samples and gave expected results. A summary of the results observed is shown in Table 8 below. The line data for testing performed with the SCoV-2 Ag Detect™ Rapid Test is shown in Table 9.

TABLE 8

Summary of interfering substances and solvents results

| Substance | Tested concentration | Negative nasal swab matrix | Positive SARS-CoV-2 nasal swab matrix |
|---|---|---|---|
| Whole Blood | 4% | No interference | No interference |
| Mucin | 0.5% | No interference | No interference |
| Chloraceptic/Cepacol | 1.5 mg/mL | No interference | No interference |
| NeilMed NasoGEL | 5% v/v | No interference | No interference |
| CVS Nasal Drops | 15% v/v | No interference | No interference |
| Afrin | 15% v/v | No interference | No interference |
| Nasal Spray | 15% v/v | No interference | No interference |
| Zicam Cold Remedy | 5% v/v | No interference | No interference |
| Alkalol Homeopathic | 1:10 dilution | No interference | No interference |
| Sore Throat Phenol Spray | 15% v/v | No interference | No interference |
| Tobramycin | 4 µg/mL | No interference | No interference |
| Mupirocin | 10 mg/mL | No interference | No interference |
| Flonase Nasal Spray | 5% v/v | No interference | No interference |
| Tamiflu | 5 mg/mL | No interference | No interference |
| Ethanol (solvent) | N/A | No interference | No interference |
| Isopropyl Alcohol (solvent) | N/A | No interference | No interference |
| 0.1M Sodium Hydroxide (solvent) | N/A | No interference | No interference |
| Dimethyl Sulfoxide (solvent) | N/A | No interference | No interference |

No interference was observed with the SCoV-2 Ag Detect™ Rapid Test for samples that contained blood components and common nasal treatments, or with pooled human nasal wash.

TABLE 9

Line data for interference substances study

| Substance | Matrix | Replicate 1 | Replicate 2 | Replicate 3 |
|---|---|---|---|---|
| Whole Blood | SARS-CoV-2 in Nasal Swab Matrix | Positive | Positive | Positive |
|  | Negative Nasal Swab Matrix | Negative | Negative | Negative |
| Mucin | SARS-CoV-2 in Nasal Swab Matrix | Positive | Positive | Positive |
|  | Negative Nasal Swab Matrix | Negative | Negative | Negative |
| Chloraseptic/ Cepacol (Benzocaine) | SARS-CoV-2 in Nasal Swab Matrix | Positive | Positive | Positive |
|  | Negative Nasal Swab Matrix | Negative | Negative | Negative |
| NeilMed NasoGEL | SARS-CoV-2 in Nasal Swab Matrix | Positive | Positive | Positive |
|  | Negative Nasal Swab Matrix | Negative | Negative | Negative |
| Nasal Drops (Phenylephrine) | SARS-CoV-2 in Nasal Swab Matrix | Positive | Positive | Positive |
|  | Negative Nasal Swab Matrix | Negative | Negative | Negative |
| Afrin (Oxymetazoline) | SARS-CoV-2 in Nasal Swab Matrix | Positive | Positive | Positive |
|  | Negative Nasal Swab Matrix | Negative | Negative | Negative |
| Nasal Spray (Cromolyn) | SARS-CoV-2 in Nasal Swab Matrix | Positive | Positive | Positive |
|  | Negative Nasal Swab Matrix | Negative | Negative | Negative |
| Zicam Cold Remedy (Zincum aceticum, Zincum gluconicum) | SARS-CoV-2 in Nasal Swab Matrix | Positive | Positive | Positive |
|  | Negative Nasal Swab Matrix | Negative | Negative | Negative |
| Alkalol Homeopathic | SARS-CoV-2 in Nasal Swab Matrix | Positive | Positive | Positive |
|  | Negative Nasal Swab Matrix | Negative | Negative | Negative |
| Sore Throat Phenol Spray (Phenol) | SARS-CoV-2 in Nasal Swab Matrix | Positive | Positive | Positive |
|  | Negative Nasal Swab Matrix | Negative | Negative | Negative |

TABLE 9-continued

Line data for interference substances study

| Substance | Matrix | Replicate 1 | Replicate 2 | Replicate 3 |
|---|---|---|---|---|
| Tobramycin | SARS-CoV-2 in Nasal Swab Matrix | Positive | Positive | Positive |
| | Negative Nasal Swab Matrix | Negative | Negative | Negative |
| Mupirocin | SARS-CoV-2 in Nasal Swab Matrix | Positive | Positive | Positive |
| | Negative Nasal Swab Matrix | Negative | Negative | Negative |
| Flonase nasal spray (Fluticasone Propionate) | SARS-CoV-2 in Nasal Swab Matrix | Positive | Positive | Positive |
| | Negative Nasal Swab Matrix | Negative | Negative | Negative |
| Tamiflu (Oseltamivir Phosphate) | SARS-CoV-2 in Nasal Swab Matrix | Positive | Positive | Positive |
| | Negative Nasal Swab Matrix | Negative | Negative | Negative |
| Ethanol (solvent) | SARS-CoV-2 in Nasal Swab Matrix | Positive | Positive | Positive |
| | Negative Nasal Swab Matrix | Negative | Negative | Negative |
| Isopropyl Alcohol (solvent) | SARS-CoV-2 in Nasal Swab Matrix | Positive | Positive | Positive |
| | Negative Nasal Swab Matrix | Negative | Negative | Negative |
| 0.1M Sodium Hydroxide (solvent) | SARS-CoV-2 in Nasal Swab Matrix | Positive | Positive | Positive |
| | Negative Nasal Swab Matrix | Negative | Negative | Negative |
| Dimethyl Sulfoxide (solvent) | SARS-CoV-2 in Nasal Swab Matrix | Positive | Positive | Positive |
| | Negative Nasal Swab Matrix | Negative | Negative | Negative |

No interference was observed for any of the substances or solvents tested on the SCoV-2 Ag Detect™ Rapid Test.

High-Dose Hook Effect:

The purpose of this study was to evaluate whether high concentrations of viral target can produce false negative results on the SCoV-2 Ag Detect™ Rapid Test.

Gamma-irradiated SARS-CoV-2 virus isolate was obtained from ATCC via BEI (RD2660, Cat. NR-52287, Lot 70039067), and spiked into pooled nasal swab matrix.

Pooled nasal swab matrix consisted of nasal swabs taken from individual healthy donors (presumed SARS-CoV-2 negative), which were eluted in 0.5 mL PBS per swab and then pooled. Prior to pooling, the eluted nasal swabs in PBS were screened to confirm lack of background reactivity on the SCoV-2 Ag Detect™ Rapid Test. To screen each nasal swab eluted in PBS, 50 µL of each eluted sample was loaded directly onto a sterile swab compatible with the SCoV-2 Ag Detect™ Rapid Test kit so that the liquid was absorbed onto the swab. Each swab was then tested on the SCoV-2 Ag Detect™ Rapid Test following the instructions in the product insert. All testing was conducted at InBios International, Inc. (Seattle, Wash.).

The SARS-CoV-2 stock solution was used neat (2.8E+06 $TCID_{50}$/mL), as well as diluted in negative nasal swab matrix to a concentration of 2.8E+05 and 1E+05 $TCID_{50}$/mL. Each dilution was loaded directly onto a sterile swab compatible with the SCoV-2 Ag Detect™ Rapid Test by slowly pipetting 20 µL of the diluted virus stock so that the virus stock was absorbed onto the swab. Each dilution was tested by an unblinded trained operator in triplicate with the SCoV-2 Ag Detect™ Rapid Test.

The hook effect level was defined as the concentration at which a positive sample tests negative (false negative). If no false negative results are obtained, no hook effect is observed.

Rapid test external controls were run by the operator prior to testing any study samples and gave expected results. Results for three viral concentrations alongside unspiked, negative matrix are shown in Table 10.

TABLE 10

Hook effect determination

| | Results | | |
|---|---|---|---|
| [SARS-CoV-2] ($TCID_{50}$/mL) | Replicate #1 | Replicate #2 | Replicate #3 |
| 2.8E+06 (neat) | Positive | Positive | Positive |
| 2.8E+05 | Positive | Positive | Positive |
| 1.0E+05 | Positive | Positive | Positive |
| 0 | Negative | Negative | Negative |

No false negative results were observed, even at the highest concentration of SARS-CoV-2 virus isolate tested (2.8E+06 $TCID_{50}$/mL). This concentration greatly exceeds concentrations expected in clinical samples.

No hook effect was observed, even at the highest concentration of SARS-CoV-2 virus isolate tested (2.8E+06 $TCID_{50}$/mL). This concentration greatly exceeds concentrations expected in clinical samples.

Specimen Stability:

The purpose of this study is to evaluate the effects of extended periods of room temperature and refrigerated storage on the stability of nasal swab specimens collected for testing on the SCoV-2 Ag Detect™ Rapid Test.

Gamma-irradiated, SARS-Related Coronavirus 2 (SARS-CoV-2), USA-WA1/2020 isolate was obtained from ATCC via BEI (RD2765, Cat. NR-52287, Lot 70039067). SARS-CoV-2, isolate USA-WA1/2020 (NR-52287) was isolated from an oropharyngeal swab from a patient with a respiratory illness who developed clinical disease (COVID-19) in January 2020 in Washington, USA. NR-52287 was prepared from infected cultured Vero E6 epithelial cell lysate, gamma irradiated (5E+06 RADs) on dry ice, and then sonicated. NR-52287 is supplied at a concentration of 2.8E+06 $TCID_{50}$/mL.

Individual nasal swab matrices were collected from individual healthy donors (presumed SARS-CoV-2 negative), then eluted in 0.5 mL PBS per swab. Each individual eluted nasal swab in PBS was screened to confirm lack of background reactivity on the SCoV-2 Ag Detect™ Rapid Test. To screen each nasal swab eluted in PBS, 50 µL of each eluted sample was loaded directly onto a sterile swab compatible with the SCoV-2 Ag Detect™ Rapid Test so that the liquid was absorbed onto the swab. Each swab was then tested on the SCoV-2 Ag Detect™ Rapid Test following the instructions in the product insert.

The gamma-irradiated, SARS-CoV-2 virus stock solution was diluted in negative nasal swab matrix prepared as described above to a concentration of 2.8E+05 virus/mL. This preparation was used throughout the study to prepare contrived samples. All testing was conducted by trained operators at InBios International, Inc. (Seattle, Wash.).

Positive specimens were prepared by spiking SARS-CoV-2 into individual nasal swab matrices to yield a weak positive (1.88E+04 $TCID_{50}$/mL, 3×LoD). Negative specimens consisted of un-spiked, analyte-negative nasal swab matrices from individual donors.

Positive and negative specimens were tested after various storage conditions. Room temperature specimens were maintained at 15±2° C. or 30±2° C., then tested at the following timepoints: 0 hours, 1 hour, 2 hours, 4 hours, 8 hours. Refrigerated specimens were maintained at 2-8° C., then tested at the following timepoints: 0 hours, 24 hours, 72 hours, 96 hours, 120 hours.

Specimen stability was evaluated by comparing the test results at each timepoint with the expected results. If no false positives or false negatives were observed at a given timepoint, then specimens were considered stable up to that timepoint.

Results are shown in the next several tables. All samples at all timepoints gave expected results.

TABLE 11

Specimen stability at low room temperature (15 ± 2° C.)

| | | Storage at low room temperature (hours) | | | | |
|---|---|---|---|---|---|---|
| Sample ID | Conc. | 0 | 1 | 2 | 4 | 8 |
| 1 | 3x LoD | Positive | Positive | Positive | Positive | Positive |
| 2 | 3x LoD | Positive | Positive | Positive | Positive | Positive |
| 3 | 3x LoD | Positive | Positive | Positive | Positive | Positive |
| 4 | 3x LoD | Positive | Positive | Positive | Positive | Positive |
| 5 | 3x LoD | Positive | Positive | Positive | Positive | Positive |
| 6 | 3x LoD | Positive | Positive | Positive | Positive | Positive |
| 7 | 3x LoD | Positive | Positive | Positive | Positive | Positive |
| 8 | 3x LoD | Positive | Positive | Positive | Positive | Positive |
| 9 | 3x LoD | Positive | Positive | Positive | Positive | Positive |
| 10 | 3x LoD | Positive | Positive | Positive | Positive | Positive |
| 11 | 0x LoD | Negative | Negative | Negative | Negative | Negative |
| 12 | 0x LoD | Negative | Negative | Negative | Negative | Negative |

TABLE 12

Specimen stability at high room temperature (30 ± 2° C.)

| | | Storage at high room temperature (hours) | | | | |
|---|---|---|---|---|---|---|
| Sample ID | Conc. | 0 | 1 | 2 | 4 | 8 |
| 13 | 3x LoD | Positive | Positive | Positive | Positive | Positive |
| 14 | 3x LoD | Positive | Positive | Positive | Positive | Positive |
| 15 | 3x LoD | Positive | Positive | Positive | Positive | Positive |
| 16 | 3x LoD | Positive | Positive | Positive | Positive | Positive |
| 17 | 3x LoD | Positive | Positive | Positive | Positive | Positive |
| 18 | 3x LoD | Positive | Positive | Positive | Positive | Positive |
| 19 | 3x LoD | Positive | Positive | Positive | Positive | Positive |
| 20 | 3x LoD | Positive | Positive | Positive | Positive | Positive |
| 21 | 3x LoD | Positive | Positive | Positive | Positive | Positive |
| 22 | 3x LoD | Positive | Positive | Positive | Positive | Positive |
| 23 | 0x LoD | Negative | Negative | Negative | Negative | Negative |
| 24 | 0x LoD | Negative | Negative | Negative | Negative | Negative |

TABLE 13

Refrigerated (2-8° C.) specimen stability

| | | Storage at refrigeration temperature (hours) | | | | |
|---|---|---|---|---|---|---|
| Sample ID | Conc. | 0 | 24 ± 2 | 72 ± 2 | 96 ± 2 | 120 ± 2 |
| 25 | 3x LoD | Positive | Positive | Positive | Positive | Positive |
| 26 | 3x LoD | Positive | Positive | Positive | Positive | Positive |
| 27 | 3x LoD | Positive | Positive | Positive | Positive | Positive |
| 28 | 3x LoD | Positive | Positive | Positive | Positive | Positive |

TABLE 13-continued

| | | Refrigerated (2-8° C.) specimen stability | | | | |
|---|---|---|---|---|---|---|
| | | Storage at refrigeration temperature (hours) | | | | |
| Sample ID | Conc. | 0 | 24 ± 2 | 72 ± 2 | 96 ± 2 | 120 ± 2 |
| 29 | 3x LoD | Positive | Positive | Positive | Positive | Positive |
| 30 | 3x LoD | Positive | Positive | Positive | Positive | Positive |
| 31 | 3x LoD | Positive | Positive | Positive | Positive | Positive |
| 32 | 3x LoD | Positive | Positive | Positive | Positive | Positive |
| 33 | 3x LoD | Positive | Positive | Positive | Positive | Positive |
| 34 | 3x LoD | Positive | Positive | Positive | Positive | Positive |
| 35 | 0x LoD | Negative | Negative | Negative | Negative | Negative |
| 36 | 0x LoD | Negative | Negative | Negative | Negative | Negative |

Specimen stability was demonstrated for up to 8 hours at room temperature, or up to 120 hours under refrigeration.

Clinical Evaluation:

Prospective Clinical Evaluation

The purpose of the prospective clinical evaluation was to determine the positive percent agreement (PPA) and negative percent agreement (NPA) for the SCoV-2 Ag Detect™ Rapid Test in a POC CLIA Waived setting.

The clinical performance of SCoV-2 Ag Detect™ Rapid Test was evaluated in a multi-site prospective study in the U.S. In the prospective study, patients presenting with symptoms consistent with possible COVID-19 infection within 5 days of symptom onset were sequentially enrolled. A total of three (3) investigational POC/CLIA-waived sites encompassing six (6) drive through collection sites participated in the prospective study.

Inclusion Criteria:
  Male and female subjects at least 18 years of age.
  Each subject within 5 days of enrollment will have signs or symptoms of possible SARS-CoV-2 infection including: fever, chills, cough, shortness of breath, difficulty breathing, fatigue, muscle or body aches, headache, new loss of taste or smell, sore throat, congestion or runny nose, nausea or vomiting, diarrhea.
  Subject is able to speak, read, and comprehend English.

Exclusion Criteria:
  Subject is an inmate or deprived of freedom by court order.

The sites' addresses are:
  Site #1: Seattle Children's drive through site, 5801 Sand Point Way NE, Seattle, Wash.
  Site #2a: Northwest Hospital drive through site, 1550 N 115th St, Seattle, Wash.
  Site #2b: Rainier Beach drive through site, 8702 Seward Park Ave S, Seattle, Wash.
  Site #2c: Federal Way drive through site, 650 SW Campus Dr, Federal Way, Wash. 98023
  Site #2d: Tukwila drive through site, 3455 S 148th St., Tukwila, Wash. 98168
  Site #3: COVID-19 Clinic drive through site, 5601 Grossmont Center Drive, La Mesa, Calif. 91942
  Each site was provided with the following:
  Clinical protocol that was IRB-approved
  Product instructions for use (IFU)
  Quick Reference Instructions (QRI)
  SCoV-2 Ag Detect™ Rapid Test kits with positive and negative controls At the drive through sites, two paired nasal swabs were collected from eligible patients. One nasal swab was tested on SCoV-2 Ag Detect™ Rapid Test immediately after collection (i.e. without placing in VTM). A paired nasal swab was collected in VTM or sterile phosphate-buffered saline for testing on the comparator assay, InBios' Smart Detect™ SARS-CoV-2 rRT-PCR Kit (EUA200180).

Each nasal swab was collected from both nostrils and the nasal swabs were assigned to SCoV-2 Ag Detect™ Rapid Test and comparator test randomly as follows. At sites #1 and #3, the order of the swab collection was determined by a predefined randomization protocol. Specifically, at site #1, the order of sample collection was determined by simple randomization based on randomly drawing pre-labeled swabs for RT-PCR vs. rapid test (e.g. if the red pre-labeled swab was drawn, then the first collected swab was assigned to RT-PCR and second for Ag assay; if the swab with no label was drawn, then the first collected swab was used for Ag assay and second swab was assigned to RT-PCR). 50% of pre-labeled and 50% unlabeled swabs were mixed and provided to site 1. At site #3, the order of sample collection was determined by a randomization function in the clinical trial management software. At site #2, the sample were collected by a double swab technique per the site's SOP. In the double swab technique, two swabs were unpacked simultaneously; swab #1 was used to collect sample from the right nostril and swab #2 was used to collect sample from the left nostril, then swab #1 was used to collect sample from the left nostril and swab #2 was used to collect sample from the right nostril. Because this collection technique should yield similar viral loads in both nasal swab specimens, no additional randomization was performed at site #2.

SCoV-2 Ag Detect™ Rapid Test was performed sequentially by 15 minimally trained operators who are representative of the intended users (i.e. the majority of operators involved in the study have medical training; none of the operators involved in the study has laboratory experience). Operators only used the QRI for the test without any training provided.

Paired nasal swabs in VTM or phosphate-buffered saline were stored at 2-8° C. for up to 72 hours, and then stored at −20° C. or below for up to 4 weeks before testing on InBios' Smart Detect™ SARS-CoV-2 rRT-PCR Kit at InBios.

Line data from the 53 patients enrolled at Site #1, 177 patients enrolled at Site #2 and 73 patients enrolled at Site #3 are presented starting on the next page. Of the 296 subjects with reported demographic information, 169 (57.1%) were female, 126 (42.7%) were male, and 1 (0.3%) reported non-binary sex, and patient ages ranged from 18-72 years.

TABLE 14

Prospective clinical evaluation specimen characteristics
Specimen Characteristics

| | | |
|---|---|---|
| Sex | Number of specimens with reported sex/total | 296/303 |
| | Female, n (%) | 169 (57.1%) |
| | Male, n (%) | 126 (42.6%) |
| | Non-binary, n (%) | 1 (0.3%) |
| Age (years) | Number of specimens with reported age/total | 297/303 |
| | Mean (SD) | 34.4 (11.4) |
| | Range | 18-72 |
| Days pso | Number of specimens with reported days pso/total | 303/303 |
| | Mean (SD) | 2.3 (1.3) |
| | Range | 0-5 |

One sample was invalid in the RT-PCR test (and negative on SCoV-2 Ag Detect™ Rapid Test) and was excluded from NPA analysis.

TABLE 15

Line Data for Clinical Evaluation with Prospective Samples (Site 1)

| | | | Sample collection | | InBios SCoV-2 Ag Detect™$ | | |
|---|---|---|---|---|---|---|---|
| Donor ID | Symptom Onset Date | Days PSO | Collection Date | Time | Rapid Test Date | Time | Rapid Test Result |
| SC-002 | Feb. 24, 2021 | 0 | Feb. 24, 2021 | 10:29 | Feb. 24, 2021 | 10:31 | Negative |
| SC-003 | Feb. 16, 2021 | 1 | Feb. 17, 2021 | 14:50 | Feb. 17, 2021 | 15:02 | Negative |
| SC-004 | Feb. 18, 2021 | 0 | Feb. 18, 2021 | 11:13 | Feb. 18, 2021 | 11:17 | Negative |
| SC-005 | Feb. 16, 2021 | 2 | Feb. 18, 2021 | 13:24 | Feb. 18, 2021 | 13:27 | Negative |
| SC-006 | Feb. 19, 2021 | 0 | Feb. 19, 2021 | 10:38 | Feb. 19, 2021 | 10:40 | Negative |
| SC-007 | Feb. 16, 2021 | 3 | Feb. 19, 2021 | 12:01 | Feb. 19, 2021 | 12:03 | Negative |
| SC-008 | Feb. 18, 2021 | 1 | Feb. 19, 2021 | 13:16 | Feb. 19, 2021 | 13:20 | Negative |
| SC-009 | Feb. 18, 2021 | 1 | Feb. 19, 2021 | 13:53 | Feb. 19, 2021 | 13:56 | Negative |
| SC-010 | Feb. 17, 2021 | 3 | Feb. 20, 2021 | 11:15 | Feb. 20, 2021 | 11:17 | Negative |
| SC-011 | Feb. 20, 2021 | 0 | Feb. 20, 2021 | 12:04 | Feb. 20, 2021 | 12:10 | Negative |
| SC-012 | Feb. 20, 2021 | 0 | Feb. 20, 2021 | 13:56 | Feb. 20, 2021 | 14:00 | Negative |
| SC-014 | Feb. 18, 2021 | 4 | Feb. 22, 2021 | 10:43 | Feb. 22, 2021 | 10:44 | Negative |
| SC-015 | Feb. 21, 2021 | 1 | Feb. 22, 2021 | 11:59 | Feb. 22, 2021 | 12:00 | Negative |
| SC-016 | Feb. 19, 2021 | 3 | Feb. 22, 2021 | 16:29 | Feb. 22, 2021 | 16:31 | Negative |
| SC-017 | Feb. 22, 2021 | 1 | Feb. 23, 2021 | 8:06 | Feb. 23, 2021 | 8:33 | Negative |
| SC-018 | Feb. 22, 2021 | 1 | Feb. 23, 2021 | 8:11 | Feb. 23, 2021 | 8:33 | Negative |
| SC-019 | Feb. 20, 2021 | 3 | Feb. 23, 2021 | 10:47 | Feb. 23, 2021 | 10:57 | Negative |
| SC-020 | Feb. 21, 2021 | 2 | Feb. 23, 2021 | 11:11 | Feb. 23, 2021 | 11:12 | Negative |
| SC-021 | Feb. 23, 2021 | 0 | Feb. 23, 2021 | 13:57 | Feb. 23, 2021 | 13:58 | Negative |
| SC-022 | Feb. 22, 2021 | 1 | Feb. 23, 2021 | 15:27 | Feb. 23, 2021 | 15:28 | Negative |
| SC-023 | Feb. 23, 2021 | 1 | Feb. 24, 2021 | 10:54 | Feb. 24, 2021 | 10:55 | Negative |
| SC-024 | Feb. 24, 2021 | 0 | Feb. 24, 2021 | 11:54 | Feb. 24, 2021 | 11:55 | Negative |
| SC-025 | Feb. 23, 2021 | 1 | Feb. 24, 2021 | 14:06 | Feb. 24, 2021 | 14:08 | Negative |
| SC-026 | Feb. 20, 2021 | 4 | Feb. 24, 2021 | 16:28 | Feb. 24, 2021 | 16:31 | Negative |
| SC-027 | Feb. 24, 2021 | 1 | Feb. 25, 2021 | 10:54 | Feb. 25, 2021 | 10:55 | Negative |
| SC-028 | Feb. 24, 2021 | 1 | Feb. 25, 2021 | 11:22 | Feb. 25, 2021 | 11:24 | Negative |
| SC-029 | Feb. 23, 2021 | 3 | Feb. 26, 2021 | 9:49 | Feb. 26, 2021 | 9:52 | Positive |
| SC-030 | Feb. 26, 2021 | 0 | Feb. 26, 2021 | 13:13 | Feb. 26, 2021 | 13:14 | Negative |
| SC-031 | Feb. 25, 2021 | 1 | Feb. 26, 2021 | 13:42 | Feb. 26, 2021 | 13:43 | Negative |
| SC-032 | Feb. 25, 2021 | 1 | Feb. 26, 2021 | 14:15 | Feb. 26, 2021 | 14:16 | Negative |
| SC-033 | Feb. 27, 2021 | 0 | Feb. 27, 2021 | 9:23 | Feb. 27, 2021 | 9:24 | Negative |
| SC-034 | Feb. 25, 2021 | 4 | Mar. 1, 2021 | 13:40 | Mar. 1, 2021 | 13:41 | Negative |
| SC-035 | Mar. 1, 2021 | 1 | Mar. 2, 2021 | 12:06 | Mar. 2, 2021 | 12:07 | Negative |
| SC-037 | Mar. 1, 2021 | 2 | Mar. 3, 2021 | 10:14 | Mar. 3, 2021 | 10:14 | Negative |
| SC-038 | Mar. 1, 2021 | 2 | Mar. 3, 2021 | 11:04 | Mar. 3, 2021 | 11:05 | Negative |
| SC-039 | Mar. 3, 2021 | 1 | Mar. 4, 2021 | 11:28 | Mar. 4, 2021 | 11:29 | Negative |
| SC-040 | Mar. 4, 2021 | 0 | Mar. 4, 2021 | 14:05 | Mar. 4, 2021 | 14:06 | Negative |
| SC-041 | Mar. 5, 2021 | 0 | Mar. 5, 2021 | 12:12 | Mar. 5, 2021 | 12:13 | Negative |
| SC-042 | Mar. 3, 2021 | 2 | Mar. 5, 2021 | 14:33 | Mar. 5, 2021 | 14:34 | Negative |
| SC-043 | Mar. 4, 2021 | 1 | Mar. 5, 2021 | 15:26 | Mar. 5, 2021 | 15:27 | Positive |
| SC-044 | Mar. 4, 2021 | 1 | Mar. 5, 2021 | 16:11 | Mar. 5, 2021 | 16:12 | Negative |
| SC-045 | Mar. 4, 2021 | 1 | Mar. 5, 2021 | 16:43 | Mar. 5, 2021 | 16:44 | Negative |
| SC-047 | Mar. 7, 2021 | 1 | Mar. 8, 2021 | 8:16 | Mar. 8, 2021 | 8:18 | Negative |
| SC-048 | Mar. 7, 2021 | 1 | Mar. 8, 2021 | 8:17 | Mar. 8, 2021 | 8:18 | Negative |
| SC-049 | Mar. 5, 2021 | 3 | Mar. 8, 2021 | 13:21 | Mar. 8, 2021 | 13:22 | Negative |
| SC-050 | Mar. 6, 2021 | 2 | Mar. 8, 2021 | 14:00 | Mar. 8, 2021 | 14:00 | Negative |
| SC-051 | Mar. 7, 2021 | 2 | Mar. 9, 2021 | 16:36 | 13:17 | 13:37 | Negative |
| SC-052 | Mar. 8, 2021 | 1 | Mar. 9, 2021 | 16:46 | 16:37 | 16:57 | Negative |
| SC-053 | Mar. 8, 2021 | 1 | Mar. 9, 2021 | 16:58 | 16:47 | 17:07 | Negative |
| SC-054 | Mar. 7, 2021 | 2 | Mar. 10, 2021 | 10:30 | 16:58 | 17:18 | Negative |
| SC-055 | Mar. 5, 2021 | 5 | Mar. 10, 2021 | 11:46 | 10:32 | 10:52 | Negative |
| SC-056 | Mar. 6, 2021 | 4 | Mar. 10, 2021 | 13:04 | 11:47 | 12:07 | Negative |
| SC-057 | Mar. 9, 2021 | 1 | Mar. 9, 2021 | 13:16 | 13:05 | 13:25 | Negative |

TABLE 15-continued

Line Data for Clinical Evaluation with Prospective Samples (Site 1)

InBios' Smart Detect ™ SARS-CoV-2 rRT-PCR*$

| Donor ID | rRT-PCR Testing Date | N gene | E gene | ORF1b | Rnase P | rRT-PCR Result |
|---|---|---|---|---|---|---|
| SC-002 | Feb. 25, 2021 | NaN | NaN | NaN | 33.69 | Negative |
| SC-003 | Feb. 21, 2021 | NaN | NaN | NaN | 33.03 | Negative |
| SC-004 | Feb. 21, 2021 | NaN | NaN | NaN | 36.63 | Negative |
| SC-005 | Feb. 21, 2021 | NaN | NaN | NaN | 34.16 | Negative |
| SC-006 | Feb. 22, 2021 | NaN | NaN | NaN | 33.38 | Negative |
| SC-007 | Feb. 22, 2021 | NaN | NaN | NaN | 29.38 | Negative |
| SC-008 | Feb. 22, 2021 | NaN | NaN | NaN | 37.17 | Negative |
| SC-009 | Feb. 22, 2021 | NaN | NaN | NaN | 33.64 | Negative |
| SC-010 | Feb. 22, 2021 | NaN | NaN | NaN | 34.21 | Negative |
| SC-011 | Feb. 22, 2021 | NaN | NaN | NaN | 35.51 | Negative |
| SC-012 | Feb. 22, 2021 | NaN | NaN | NaN | 31.82 | Negative |
| SC-014 | Feb. 23, 2021 | NaN | NaN | NaN | 29.62 | Negative |
| SC-015 | Feb. 23, 2021 | NaN | NaN | NaN | 32.05 | Negative |
| SC-016 | Feb. 23, 2021 | NaN | NaN | NaN | 33.43 | Negative |
| SC-017 | Feb. 25, 2021 | NaN | NaN | NaN | 34.10 | Negative |
| SC-018 | Feb. 25, 2021 | NaN | NaN | NaN | 33.59 | Negative |
| SC-019 | Feb. 25, 2021 | NaN | NaN | NaN | 36.42 | Negative |
| SC-020 | Feb. 25, 2021 | NaN | NaN | NaN | 36.59 | Negative |
| SC-021 | Feb. 25, 2021 | NaN | NaN | NaN | 36.18 | Negative |
| SC-022 | Feb. 25, 2021 | NaN | NaN | NaN | 37.97 | Negative |
| SC-023 | Feb. 25, 2021 | NaN | NaN | NaN | 37.67 | Negative |
| SC-024 | Feb. 25, 2021 | NaN | NaN | NaN | 35.52 | Negative |
| SC-025 | Feb. 25, 2021 | NaN | NaN | NaN | 34.03 | Negative |
| SC-026 | Feb. 25, 2021 | NaN | NaN | NaN | 34.66 | Negative |
| SC-027 | Mar. 1, 2021 | NaN | NaN | NaN | 34.32 | Negative |
| SC-028 | Mar. 1, 2021 | NaN | NaN | NaN | 36.40 | Negative |
| SC-029 | Mar. 1, 2021 | 18.68 | 17.27 | 22.36 | 34.16 | Positive |
| SC-030 | Mar. 1, 2021 | NaN | NaN | NaN | 35.74 | Negative |
| SC-031 | Mar. 1, 2021 | NaN | NaN | NaN | 36.19 | Negative |
| SC-032 | Mar. 1, 2021 | NaN | NaN | NaN | 31.86 | Negative |
| SC-033 | Mar. 1, 2021 | NaN | NaN | NaN | 34.13 | Negative |
| SC-034 | Mar. 4, 2021 | NaN | NaN | NaN | 31.58 | Negative |
| SC-035 | Mar. 4, 2021 | NaN | NaN | NaN | 31.94 | Negative |
| SC-037 | Mar. 4, 2021 | NaN | NaN | NaN | 36.86 | Negative |
| SC-038 | Mar. 4, 2021 | NaN | NaN | NaN | 36.40 | Negative |
| SC-039 | Mar. 8, 2021 | NaN | NaN | NaN | 32.36 | Negative |
| SC-040 | Mar. 8, 2021 | NaN | NaN | NaN | 32.36 | Negative |
| SC-041 | Mar. 8, 2021 | NaN | NaN | NaN | 33.91 | Negative |
| SC-042 | Mar. 8, 2021 | NaN | NaN | NaN | 31.62 | Negative |
| SC-043 | Mar. 8, 2021 | 22.83 | 22.16 | 25.69 | 35.80 | Positive |
| SC-044 | Mar. 8, 2021 | NaN | NaN | NaN | 32.86 | Negative |
| SC-045 | Mar. 8, 2021 | NaN | NaN | NaN | 35.35 | Negative |
| SC-047 | Mar. 10, 2021 | NaN | NaN | NaN | 37.80 | Negative |
| SC-048 | Mar. 10, 2021 | NaN | NaN | NaN | 36.93 | Negative |
| SC-049 | Mar. 10, 2021 | NaN | NaN | NaN | 35.20 | Negative |
| SC-050 | Mar. 10, 2021 | NaN | NaN | NaN | 36.96 | Negative |
| SC-051 | Mar. 15, 2021 | NaN | NaN | NaN | 36.98 | Negative |
| SC-052 | Mar. 11, 2021 | NaN | NaN | NaN | 37.14 | Negative |
| SC-053 | Mar. 11, 2021 | NaN | NaN | NaN | 34.52 | Negative |
| SC-054 | Mar. 11, 2021 | NaN | NaN | NaN | 32.70 | Negative |
| SC-055 | Mar. 11, 2021 | NaN | NaN | NaN | 35.09 | Negative |
| SC-056 | Mar. 11, 2021 | NaN | NaN | NaN | 33.04 | Negative |
| SC-057 | Mar. 11, 2021 | NaN | NaN | NaN | 35.24 | Negative |

TABLE 16

Line Data for Clinical Evaluation with Prospective Samples (Sites 2a, 2b, 2c, 2d)

| | | | Sample collection | | InBios SCoV-2 Ag Detect ™$ | | |
|---|---|---|---|---|---|---|---|
| Donor ID | Symptom Onset Date | Days PSO | Collection Date | Time | Rapid Test Date | Time | Rapid Test Result |
| 42-37-0001-6 | Feb. 13, 2021 | 4 | Feb. 17, 2021 | 11:23:00 | Feb. 17, 2021 | 11:41:00 | Negative |
| 42-37-0002-7 | Feb. 13, 2021 | 4 | Feb. 17, 2021 | 12:33:00 | Feb. 17, 2021 | 12:53:00 | Negative |
| 42-37-0003-0 | Feb. 14, 2021 | 4 | Feb. 18, 2021 | 10:19:00 | Feb. 18, 2021 | 10:30:00 | Negative |
| 42-37-0004-3 | Feb. 17, 2021 | 1 | Feb. 18, 2021 | 10:46:00 | Feb. 18, 2021 | 10:58:00 | Negative |
| 42-37-0005-5 | Feb. 13, 2021 | 5 | Feb. 18, 2021 | 11:16:00 | Feb. 18, 2021 | 11:30:00 | Negative |
| 42-37-0006-8 | Feb. 14, 2021 | 4 | Feb. 18, 2021 | 13:41:00 | Feb. 18, 2021 | 13:50:00 | Negative |
| 42-37-0007-9 | Feb. 13, 2021 | 5 | Feb. 18, 2021 | 14:15:00 | Feb. 18, 2021 | 14:24:00 | Negative |

TABLE 16-continued

Line Data for Clinical Evaluation with Prospective Samples (Sites 2a, 2b, 2c, 2d)

| | | | | | | | |
|---|---|---|---|---|---|---|---|
| 42-37-0009-2 | Feb. 16, 2021 | 3 | Feb. 19, 2021 | 11:46:00 | Feb. 19, 2021 | 11:54:00 | Negative |
| 42-37-0010-8 | Feb. 17, 2021 | 2 | Feb. 19, 2021 | 12:02:00 | Feb. 19, 2021 | 12:12:00 | Negative |
| 42-37-0011-4 | Feb. 19, 2021 | 3 | Feb. 22, 2021 | 10:36:00 | Feb. 22, 2021 | 10:45:00 | Negative |
| 42-37-0012-0 | Feb. 19, 2021 | 3 | Feb. 22, 2021 | 10:57:00 | Feb. 22, 2021 | 11:04:00 | Negative |
| 42-37-0013-7 | Feb. 20, 2021 | 2 | Feb. 22, 2021 | 11:46:00 | Feb. 22, 2021 | 11:55:00 | Negative |
| 42-37-0014-5 | Feb. 19, 2021 | 3 | Feb. 22, 2021 | 12:20:00 | Feb. 22, 2021 | 12:30:00 | Negative |
| 42-37-0015-3 | Feb. 19, 2021 | 3 | Feb. 22, 2021 | 12:57:00 | Feb. 22, 2021 | 13:04:00 | Negative |
| 42-37-0016-1 | Feb. 20, 2021 | 3 | Feb. 23, 2021 | 9:33:00 | Feb. 23, 2021 | 9:42:00 | Negative |
| 42-37-0017-2 | Feb. 22, 2021 | 1 | Feb. 23, 2021 | 10:00:00 | Feb. 23, 2021 | 10:07:00 | Negative |
| 42-37-0018-6 | Feb. 20, 2021 | 3 | Feb. 23, 2021 | 11:01:00 | Feb. 23, 2021 | 11:06:00 | Negative |
| 42-37-0019-9 | Feb. 22, 2021 | 1 | Feb. 23, 2021 | 13:20:00 | Feb. 23, 2021 | 13:26:00 | Negative |
| 43-37-0001-5 | Feb. 21, 2021 | 3 | Feb. 24, 2021 | 11:01:00 | Feb. 24, 2021 | 11:08:00 | Negative |
| 43-37-0002-6 | Feb. 20, 2021 | 4 | Feb. 24, 2021 | 12:28:00 | Feb. 24, 2021 | 12:36:00 | Negative |
| 43-37-0003-1 | Feb. 21, 2021 | 3 | Feb. 24, 2021 | 13:35:00 | Feb. 24, 2021 | 13:47:00 | Negative |
| 42-37-0021-1 | Feb. 24, 2021 | 1 | Feb. 25, 2021 | 9:43:00 | Feb. 25, 2021 | 9:54:00 | Negative |
| 42-37-0022-2 | Feb. 22, 2021 | 3 | Feb. 25, 2021 | 10:19:00 | Feb. 25, 2021 | 10:28:00 | Negative |
| 42-37-0023-5 | Feb. 22, 2021 | 3 | Feb. 25, 2021 | 10:20:00 | Feb. 25, 2021 | 10:32:00 | Negative |
| 42-37-0024-8 | Feb. 23, 2021 | 2 | Feb. 25, 2021 | 10:54:00 | Feb. 25, 2021 | 11:00:00 | Negative |
| 42-37-0025-0 | Feb. 22, 2021 | 3 | Feb. 25, 2021 | 11:18:00 | Feb. 25, 2021 | 11:26:00 | Negative |
| 42-37-0026-3 | Feb. 25, 2021 | 0 | Feb. 25, 2021 | 11:15:00 | Feb. 25, 2021 | 11:29:00 | Negative |
| 42-37-0027-4 | Feb. 24, 2021 | 1 | Feb. 25, 2021 | 12:08:00 | Feb. 25, 2021 | 12:13:00 | Positive |
| 43-37-0006-7 | Feb. 25, 2021 | 1 | Feb. 26, 2021 | 10:30:00 | Feb. 26, 2021 | 10:45:00 | Negative |
| 43-37-0005-9 | Feb. 23, 2021 | 3 | Feb. 26, 2021 | 11:00:00 | Feb. 26, 2021 | 11:08:00 | Negative |
| 43-37-0007-8 | Feb. 22, 2021 | 4 | Feb. 26, 2021 | 12:58:00 | Feb. 26, 2021 | 13:04:00 | Positive |
| 43-37-0008-0 | Feb. 25, 2021 | 4 | Mar. 1, 2021 | 10:22:00 | Mar. 1, 2021 | 10:29:00 | Negative |
| 43-37-0009-3 | Feb. 26, 2021 | 3 | Mar. 1, 2021 | 11:42:00 | Mar. 1, 2021 | 11:50:00 | Negative |
| 43-37-0010-7 | Feb. 26, 2021 | 3 | Mar. 1, 2021 | 12:26:00 | Mar. 1, 2021 | 12:32:00 | Negative |
| 43-37-0011-0 | Feb. 27, 2021 | 2 | Mar. 1, 2021 | 13:12:00 | Mar. 1, 2021 | 13:17:00 | Negative |
| 43-37-0012-1 | Feb. 27, 2021 | 2 | Mar. 1, 2021 | 13:45:00 | Mar. 1, 2021 | 13:51:00 | Negative |
| 42-37-0028-9 | Mar. 1, 2021 | 1 | Mar. 2, 2021 | 9:47:00 | Mar. 2, 2021 | 9:51:00 | Negative |
| 42-37-0029-7 | Feb. 27, 2021 | 3 | Mar. 2, 2021 | 11:55:00 | Mar. 2, 2021 | 12:02:00 | Negative |
| 42-37-0030-2 | Mar. 2, 2021 | 1 | Mar. 3, 2021 | 10:34:00 | Mar. 3, 2021 | 10:39:00 | Negative |
| 42-37-0031-5 | Mar. 2, 2021 | 1 | Mar. 3, 2021 | 11:16:00 | Mar. 3, 2021 | 11:23:00 | Negative |
| 42-37-0032-6 | Mar. 3, 2021 | 1 | Mar. 4, 2021 | 10:40:00 | Mar. 4, 2021 | 10:50:00 | Negative |
| 42-37-0033-1 | Mar. 1, 2021 | 3 | Mar. 4, 2021 | 11:32:00 | Mar. 4, 2021 | 11:43:00 | Negative |
| 42-37-0034-4 | Mar. 4, 2021 | 0 | Mar. 4, 2021 | 11:29:00 | Mar. 4, 2021 | 11:45:00 | Negative |
| 42-37-0035-9 | Mar. 1, 2021 | 3 | Mar. 4, 2021 | 12:10:00 | Mar. 4, 2021 | 12:17:00 | Negative |
| 43-37-0013-6 | Mar. 4, 2021 | 1 | Mar. 5, 2021 | 10:48:00 | Mar. 5, 2021 | 10:53:00 | Negative |
| 43-37-0014-9 | Mar. 4, 2021 | 1 | Mar. 5, 2021 | 11:24:00 | Mar. 5, 2021 | 11:26:00 | Negative |
| 43-37-0015-4 | Mar. 4, 2021 | 1 | Mar. 5, 2021 | 11:47:00 | Mar. 5, 2021 | 11:56:00 | Negative |
| 42-37-0038-0 | Mar. 6, 2021 | 2 | Mar. 8, 2021 | 10:30:00 | Mar. 8, 2021 | 10:41:00 | Negative |
| 42-37-0039-3 | Mar. 5, 2021 | 3 | Mar. 8, 2021 | 10:43:00 | Mar. 8, 2021 | 10:46:00 | Negative |
| 42-37-0040-7 | Mar. 5, 2021 | 3 | Mar. 8, 2021 | 13:10:00 | Mar. 8, 2021 | 13:14:00 | Negative |
| 44-37-0001-4 | Mar. 6, 2021 | 3 | Mar. 9, 2021 | 10:55:00 | Mar. 9, 2021 | 11:02:00 | Negative |
| 42-37-0036-7 | Mar. 7, 2021 | 1 | Mar. 8, 2021 | 10:08:00 | Mar. 8, 2021 | 10:17:00 | Negative |
| 42-37-0037-8 | Mar. 5, 2021 | 3 | Mar. 8, 2021 | 10:05:00 | Mar. 8, 2021 | 10:19:00 | Negative |
| 44-37-0003-7 | Mar. 7, 2021 | 2 | Mar. 9, 2021 | 11:30:00 | Mar. 9, 2021 | 11:35:00 | Negative |
| 44-37-0004-5 | Mar. 7, 2021 | 2 | Mar. 9, 2021 | 11:56:00 | Mar. 9, 2021 | 12:06:00 | Negative |
| 44-37-0005-3 | Mar. 7, 2021 | 2 | Mar. 9, 2021 | 12:18:00 | Mar. 9, 2021 | 12:20:00 | Negative |
| 44-37-0006-1 | Mar. 7, 2021 | 3 | Mar. 10, 2021 | 10:08:00 | Mar. 10, 2021 | 10:11:00 | Negative |
| 44-37-0007-2 | Mar. 7, 2021 | 3 | Mar. 10, 2021 | 10:12:00 | Mar. 10, 2021 | 10:19:00 | Negative |
| 44-37-0008-6 | Mar. 9, 2021 | 1 | Mar. 10, 2021 | 10:34:00 | Mar. 10, 2021 | 10:40:00 | Negative |
| 44-37-0009-9 | Mar. 9, 2021 | 1 | Mar. 10, 2021 | 10:53:00 | Mar. 10, 2021 | 10:58:00 | Positive |
| 44-37-0010-1 | Mar. 8, 2021 | 2 | Mar. 10, 2021 | 11:24:00 | Mar. 10, 2021 | 11:30:00 | Negative |
| 44-37-0011-6 | Mar. 9, 2021 | 1 | Mar. 10, 2021 | 11:55:00 | Mar. 10, 2021 | 12:02:00 | Negative |
| 44-37-0012-7 | Mar. 9, 2021 | 1 | Mar. 10, 2021 | 13:43:00 | Mar. 10, 2021 | 13:50:00 | Negative |
| 44-37-0013-0 | Mar. 9, 2021 | 1 | Mar. 10, 2021 | 13:48:00 | Mar. 10, 2021 | 13:55:00 | Negative |
| 44-37-0014-3 | Mar. 9, 2021 | 2 | Mar. 11, 2021 | 10:44:00 | Mar. 11, 2021 | 10:55:00 | Negative |
| 44-37-0015-5 | Mar. 7, 2021 | 4 | Mar. 11, 2021 | 11:10:00 | Mar. 11, 2021 | 11:16:00 | Negative |
| 44-37-0017-9 | Mar. 10, 2021 | 1 | Mar. 11, 2021 | 12:31:00 | Mar. 11, 2021 | 12:35:00 | Negative |
| 44-37-0018-4 | Mar. 9, 2021 | 2 | Mar. 11, 2021 | 13:00:00 | Mar. 11, 2021 | 13:05:00 | Negative |
| 44-37-0019-2 | Mar. 12, 2021 | 0 | Mar. 12, 2021 | 9:45:00 | Mar. 12, 2021 | 9:49:00 | Negative |
| 44-37-0020-4 | Mar. 11, 2021 | 1 | Mar. 12, 2021 | 9:50:00 | Mar. 12, 2021 | 9:58:00 | Negative |
| 44-37-0021-8 | Mar. 11, 2021 | 1 | Mar. 12, 2021 | 10:07:00 | Mar. 12, 2021 | 10:15:00 | Negative |
| 44-37-0022-9 | Mar. 10, 2021 | 2 | Mar. 12, 2021 | 10:30:00 | Mar. 12, 2021 | 10:35:00 | Negative |
| 44-37-0023-3 | Mar. 7, 2021 | 5 | Mar. 12, 2021 | 10:35:00 | Mar. 12, 2021 | 10:43:00 | Negative |
| 44-37-0024-1 | Mar. 11, 2021 | 1 | Mar. 12, 2021 | 10:41:00 | Mar. 12, 2021 | 10:46:00 | Negative |
| 44-37-0025-7 | Mar. 10, 2021 | 2 | Mar. 12, 2021 | 11:45:00 | Mar. 12, 2021 | 11:52:00 | Negative |
| 44-37-0026-5 | Mar. 11, 2021 | 1 | Mar. 12, 2021 | 13:40:00 | Mar. 12, 2021 | 13:48:00 | Negative |
| 44-37-0027-6 | Mar. 14, 2021 | 1 | Mar. 15, 2021 | 9:51:00 | Mar. 15, 2021 | 9:59:00 | Negative |
| 44-37-0028-2 | Mar. 13, 2021 | 2 | Mar. 15, 2021 | 10:06:00 | Mar. 15, 2021 | 10:10:00 | Negative |
| 44-37-0029-0 | Mar. 12, 2021 | 3 | Mar. 15, 2021 | 11:01:00 | Mar. 15, 2021 | 11:08:00 | Negative |
| 44-37-0030-9 | Mar. 14, 2021 | 1 | Mar. 15, 2021 | 11:30:00 | Mar. 15, 2021 | 11:33:00 | Negative |
| 44-37-0031-3 | Mar. 13, 2021 | 2 | Mar. 15, 2021 | 13:16:00 | Mar. 15, 2021 | 13:22:00 | Negative |
| 44-37-0032-4 | Mar. 13, 2021 | 2 | Mar. 15, 2021 | 13:37:00 | Mar. 15, 2021 | 13:43:00 | Negative |
| 44-37-0033-8 | Mar. 14, 2021 | 1 | Mar. 15, 2021 | 14:09:00 | Mar. 15, 2021 | 14:13:00 | Negative |
| 44-37-0034-6 | Mar. 11, 2021 | 4 | Mar. 15, 2021 | 14:11:00 | Mar. 15, 2021 | 14:15:00 | Negative |
| 44-37-0035-2 | Mar. 17, 2021 | 2 | Mar. 19, 2021 | 10:01:00 | Mar. 19, 2021 | 10:05:00 | Negative |

TABLE 16-continued

Line Data for Clinical Evaluation with Prospective Samples (Sites 2a, 2b, 2c, 2d)

| | | | | | | | |
|---|---|---|---|---|---|---|---|
| 44-37-0036-0 | Mar. 17, 2021 | 2 | Mar. 19, 2021 | 11:50:00 | Mar. 19, 2021 | 11:53:00 | Negative |
| 44-37-0037-1 | Mar. 19, 2021 | 0 | Mar. 19, 2021 | 13:58:00 | Mar. 19, 2021 | 14:02:00 | Negative |
| 44-37-0038-7 | Mar. 18, 2021 | 4 | Mar. 22, 2021 | 10:28:00 | Mar. 22, 2021 | 10:37:00 | Negative |
| 44-37-0040-0 | Mar. 19, 2021 | 3 | Mar. 22, 2021 | 13:12:00 | Mar. 22, 2021 | 13:17:00 | Negative |
| 44-37-0041-7 | Mar. 22, 2021 | 1 | Mar. 23, 2021 | 9:48:00 | Mar. 23, 2021 | 9:53:00 | Negative |
| 44-37-0048-3 | Mar. 27, 2021 | 2 | Mar. 29, 2021 | 9:46:00 | Mar. 29, 2021 | 9:53:00 | Positive |
| 44-37-0047-5 | Mar. 20, 2021 | 3 | Mar. 23, 2021 | 14:08:00 | Mar. 23, 2021 | 14:17:00 | Negative |
| 44-37-0049-1 | Mar. 25, 2021 | 4 | Mar. 29, 2021 | 10:05:00 | Mar. 29, 2021 | 10:10:00 | Negative |
| 44-37-0050-6 | Mar. 26, 2021 | 3 | Mar. 29, 2021 | 10:06:00 | Mar. 29, 2021 | 10:17:00 | Negative |
| 44-37-0052-2 | Mar. 28, 2021 | 1 | Mar. 29, 2021 | 11:02:00 | Mar. 29, 2021 | 11:08:00 | Negative |
| 44-37-0053-5 | Mar. 26, 2021 | 3 | Mar. 29, 2021 | 11:44:00 | Mar. 29, 2021 | 12:00:00 | Negative |
| 44-37-0055-0 | Mar. 27, 2021 | 2 | Mar. 29, 2021 | 11:43:00 | Mar. 29, 2021 | 12:00:00 | Positive |
| 44-37-0056-3 | Mar. 28, 2021 | 1 | Mar. 29, 2021 | 11:49:00 | Mar. 29, 2021 | 11:56:00 | Negative |
| 44-37-0057-4 | Mar. 29, 2021 | 0 | Mar. 29, 2021 | 14:07:00 | Mar. 29, 2021 | 14:10:00 | Negative |
| 44-37-0058-9 | Mar. 29, 2021 | 1 | Mar. 30, 2021 | 9:58:00 | Mar. 30, 2021 | 10:04:00 | Negative |
| 44-37-0059-7 | Mar. 27, 2021 | 3 | Mar. 30, 2021 | 10:07:00 | Mar. 30, 2021 | 10:15:00 | Negative |
| 44-37-0060-2 | Mar. 27, 2021 | 3 | Mar. 30, 2021 | 10:30:00 | Mar. 30, 2021 | 10:36:00 | Negative |
| 44-37-0061-5 | Mar. 27, 2021 | 3 | Mar. 30, 2021 | 10:34:00 | Mar. 30, 2021 | 10:45:00 | Negative |
| 44-37-0062-6 | Mar. 27, 2021 | 3 | Mar. 30, 2021 | 11:25:00 | Mar. 30, 2021 | 11:32:00 | Positive |
| 44-37-0063-1 | Mar. 29, 2021 | 1 | Mar. 30, 2021 | 12:54:00 | Mar. 30, 2021 | 12:59:00 | Positive |
| 44-37-0064-4 | Mar. 28, 2021 | 2 | Mar. 30, 2021 | 12:57:00 | Mar. 30, 2021 | 13:05:00 | Positive |
| 44-37-0066-7 | Mar. 31, 2021 | 2 | Apr. 2, 2021 | 9:35:00 | Apr. 2, 2021 | 9:42:00 | Negative |
| 44-37-0065-9 | Mar. 26, 2021 | 4 | Mar. 30, 2021 | 13:54:00 | Mar. 30, 2021 | 14:00:00 | Negative |
| 44-37-0067-8 | Mar. 31, 2021 | 2 | Apr. 2, 2021 | 9:38:00 | Apr. 2, 2021 | 9:44:00 | Negative |
| 44-37-0068-0 | Mar. 29, 2021 | 4 | Apr. 2, 2021 | 9:45:00 | Apr. 2, 2021 | 9:50:00 | Negative |
| 44-37-0069-3 | Apr. 1, 2021 | 1 | Apr. 2, 2021 | 10:18:00 | Apr. 2, 2021 | 10:22:00 | Negative |
| 44-37-0071-2 | Mar. 28, 2021 | 5 | Apr. 2, 2021 | 11:58:00 | Apr. 2, 2021 | 12:01:00 | Negative |
| 44-37-0070-5 | Mar. 29, 2021 | 4 | Apr. 2, 2021 | 11:06:00 | Apr. 2, 2021 | 11:10:00 | Positive |
| 44-37-0072-3 | Mar. 30, 2021 | 3 | Apr. 2, 2021 | 14:14:00 | Apr. 2, 2021 | 14:19:00 | Positive |
| 44-37-0073-9 | Apr. 3, 2021 | 2 | Apr. 5, 2021 | 9:53:00 | Apr. 5, 2021 | 10:01:00 | Negative |
| 45-37-0001-7 | Mar. 15, 2021 | 1 | Mar. 16, 2021 | 11:08:00 | Mar. 16, 2021 | 11:16:00 | Negative |
| 45-37-0002-8 | Mar. 16, 2021 | 1 | Mar. 17, 2021 | 9:42:00 | Mar. 17, 2021 | 9:46:00 | Negative |
| 45-37-0003-4 | Mar. 16, 2021 | 1 | Mar. 17, 2021 | 9:48:00 | Mar. 17, 2021 | 9:52:00 | Negative |
| 45-37-0004-2 | Mar. 14, 2021 | 3 | Mar. 17, 2021 | 10:05:00 | Mar. 17, 2021 | 10:11:00 | Positive |
| 45-37-0005-6 | Mar. 13, 2021 | 4 | Mar. 17, 2021 | 10:08:00 | Mar. 17, 2021 | 10:17:00 | Positive |
| 45-37-0006-9 | Mar. 16, 2021 | 1 | Mar. 17, 2021 | 11:51:00 | Mar. 17, 2021 | 11:56:00 | Negative |
| 45-37-0007-5 | Mar. 14, 2021 | 4 | Mar. 18, 2021 | 10:02:00 | Mar. 18, 2021 | 10:10:00 | Positive |
| 45-37-0008-3 | Mar. 15, 2021 | 3 | Mar. 18, 2021 | 10:46:00 | Mar. 18, 2021 | 10:50:00 | Negative |
| 45-37-0009-1 | Mar. 15, 2021 | 3 | Mar. 18, 2021 | 13:00:00 | Mar. 18, 2021 | 13:05:00 | Negative |
| 45-37-0010-9 | Mar. 15, 2021 | 3 | Mar. 18, 2021 | 14:16:00 | Mar. 18, 2021 | 14:23:00 | Negative |
| 44-37-0039-5 | Mar. 21, 2021 | 1 | Mar. 22, 2021 | 10:50:00 | Mar. 22, 2021 | 11:10:00 | Negative |
| 44-37-0042-8 | Mar. 22, 2021 | 1 | Mar. 23, 2021 | 11:09:00 | Mar. 23, 2021 | 11:14:00 | Negative |
| 44-37-0043-4 | Mar. 22, 2021 | 1 | Mar. 23, 2021 | 11:23:00 | Mar. 23, 2021 | 11:29:00 | Negative |
| 44-37-0044-2 | Mar. 21, 2021 | 2 | Mar. 23, 2021 | 13:10:00 | Mar. 23, 2021 | 13:14:00 | Negative |
| 44-37-0045-6 | Mar. 21, 2021 | 2 | Mar. 23, 2021 | 13:40:00 | Mar. 23, 2021 | 13:45:00 | Negative |
| 44-37-0046-9 | Mar. 20, 2021 | 3 | Mar. 23, 2021 | 13:45:00 | Mar. 23, 2021 | 13:50:00 | Negative |
| 45-37-0012-4 | Mar. 22, 2021 | 2 | Mar. 24, 2021 | 10:02:00 | Mar. 24, 2021 | 10:07:00 | Negative |
| 45-37-0013-8 | Mar. 23, 2021 | 1 | Mar. 24, 2021 | 10:10:00 | Mar. 24, 2021 | 10:16:00 | Negative |
| 45-37-0014-6 | Mar. 21, 2021 | 3 | Mar. 24, 2021 | 10:14:00 | Mar. 24, 2021 | 10:19:00 | Negative |
| 45-37-0015-2 | Mar. 22, 2021 | 2 | Mar. 24, 2021 | 10:52:00 | Mar. 24, 2021 | 10:58:00 | Negative |
| 45-37-0016-0 | Mar. 22, 2021 | 2 | Mar. 24, 2021 | 10:54:00 | Mar. 24, 2021 | 10:59:00 | Negative |
| 45-37-0017-1 | Mar. 20, 2021 | 4 | Mar. 24, 2021 | 11:16:00 | Mar. 24, 2021 | 11:21:00 | Negative |
| 45-37-0018-7 | Mar. 21, 2021 | 3 | Mar. 24, 2021 | 11:27:00 | Mar. 24, 2021 | 11:31:00 | Negative |
| 45-37-0019-5 | Mar. 23, 2021 | 1 | Mar. 24, 2021 | 11:34:00 | Mar. 24, 2021 | 11:38:00 | Negative |
| 45-37-0020-7 | Mar. 23, 2021 | 1 | Mar. 24, 2021 | 11:40:00 | Mar. 24, 2021 | 11:47:00 | Negative |
| 45-37-0021-0 | Mar. 24, 2021 | 1 | Mar. 25, 2021 | 10:00:00 | Mar. 25, 2021 | 10:05:00 | Negative |
| 45-37-0022-1 | Mar. 23, 2021 | 2 | Mar. 25, 2021 | 10:25:00 | Mar. 25, 2021 | 10:30:00 | Negative |
| 45-37-0023-6 | Mar. 24, 2021 | 1 | Mar. 25, 2021 | 10:39:00 | Mar. 25, 2021 | 10:43:00 | Negative |
| 45-37-0024-9 | Mar. 22, 2021 | 3 | Mar. 25, 2021 | 11:02:00 | Mar. 25, 2021 | 11:06:00 | Negative |
| 45-37-0025-4 | Mar. 22, 2021 | 3 | Mar. 25, 2021 | 11:56:00 | Mar. 25, 2021 | 12:00:00 | Negative |
| 45-37-0026-2 | Mar. 22, 2021 | 3 | Mar. 25, 2021 | 13:52:00 | Mar. 25, 2021 | 14:00:00 | Negative |
| 45-37-0027-3 | Mar. 24, 2021 | 1 | Mar. 25, 2021 | 14:10:00 | Mar. 25, 2021 | 14:15:00 | Negative |
| 45-37-0028-5 | Mar. 29, 2021 | 2 | Mar. 31, 2021 | 10:00:00 | Mar. 31, 2021 | 10:06:00 | Negative |
| 45-37-0029-8 | Mar. 27, 2021 | 4 | Mar. 31, 2021 | 10:06:00 | Mar. 31, 2021 | 10:11:00 | Negative |
| 45-37-0030-1 | Mar. 30, 2021 | 1 | Mar. 31, 2021 | 10:10:00 | Mar. 31, 2021 | 10:16:00 | Positive |
| 45-37-0031-6 | Mar. 28, 2021 | 3 | Mar. 31, 2021 | 11:05:00 | Mar. 31, 2021 | 11:11:00 | Positive |
| 45-37-0032-7 | Mar. 31, 2021 | 1 | Apr. 1, 2021 | 9:45:00 | Apr. 1, 2021 | 9:52:00 | Positive |
| 45-37-0033-0 | Mar. 31, 2021 | 1 | Apr. 1, 2021 | 9:55:00 | Apr. 1, 2021 | 9:59:00 | Negative |
| 45-37-0035-5 | Mar. 29, 2021 | 3 | Apr. 1, 2021 | 10:11:00 | Apr. 1, 2021 | 10:20:00 | Negative |
| 45-37-0036-8 | Mar. 28, 2021 | 4 | Apr. 1, 2021 | 10:34:00 | Apr. 1, 2021 | 10:39:00 | Positive |
| 45-37-0037-9 | Apr. 1, 2021 | 0 | Apr. 1, 2021 | 10:41:00 | Apr. 1, 2021 | 10:47:00 | Negative |
| 45-37-0038-4 | Mar. 29, 2021 | 3 | Apr. 1, 2021 | 13:30:00 | Apr. 1, 2021 | 13:37:00 | Negative |
| 45-37-0039-2 | Mar. 27, 2021 | 5 | Apr. 1, 2021 | 13:58:00 | Apr. 1, 2021 | 2:03:00 | Positive |
| 44-37-0074-7 | Apr. 3, 2021 | 2 | Apr. 5, 2021 | 10:02:00 | Apr. 5, 2021 | 10:08:00 | Positive |
| 44-37-0075-1 | Apr. 3, 2021 | 2 | Apr. 5, 2021 | 10:00:00 | Apr. 5, 2021 | 10:08:00 | Negative |
| 44-37-0076-4 | Apr. 2, 2021 | 3 | Apr. 5, 2021 | 10:36:00 | Apr. 5, 2021 | 10:40:00 | Positive |
| 44-37-0077-0 | Apr. 2, 2021 | 3 | Apr. 5, 2021 | 10:42:00 | Apr. 5, 2021 | 10:49:00 | Negative |
| 44-37-0078-8 | Apr. 4, 2021 | 1 | Apr. 5, 2021 | 11:10:00 | Apr. 5, 2021 | 11:15:00 | Negative |

TABLE 16-continued

Line Data for Clinical Evaluation with Prospective Samples (Sites 2a, 2b, 2c, 2d)

| | | | | | | | |
|---|---|---|---|---|---|---|---|
| 44-37-0079-6 | Apr. 2, 2021 | 3 | Apr. 5, 2021 | 12:37:00 | Apr. 5, 2021 | 12:44:00 | Negative |
| 44-37-0080-7 | Apr. 1, 2021 | 4 | Apr. 5, 2021 | 12:44:00 | Apr. 5, 2021 | 12:50:00 | Negative |
| 44-37-0081-0 | Apr. 3, 2021 | 2 | Apr. 5, 2021 | 14:14:00 | Apr. 5, 2021 | 14:21:00 | Negative |
| 44-37-0082-1 | Apr. 1, 2021 | 4 | Apr. 5, 2021 | 14:18:00 | Apr. 5, 2021 | 14:28:00 | Negative |
| 44-37-0083-6 | Apr. 3, 2021 | 3 | Apr. 6, 2021 | 9:47:00 | Apr. 6, 2021 | 9:55:00 | Positive |
| 44-37-0084-9 | Apr. 2, 2021 | 4 | Apr. 6, 2021 | 9:55:00 | Apr. 6, 2021 | 10:00:00 | Positive |
| 44-37-0085-4 | Apr. 3, 2021 | 3 | Apr. 6, 2021 | 9:55:00 | Apr. 6, 2021 | 10:00:00 | Negative |
| 44-37-0086-2 | Apr. 6, 2021 | 0 | Apr. 6, 2021 | 11:07:00 | Apr. 6, 2021 | 11:15:00 | Negative |
| 44-37-0087-3 | Apr. 3, 2021 | 3 | Apr. 6, 2021 | 11:13:00 | Apr. 6, 2021 | 11:20:00 | Positive |
| 44-37-0088-5 | Apr. 5, 2021 | 1 | Apr. 6, 2021 | 11:13:00 | Apr. 6, 2021 | 11:16:00 | Negative |
| 44-37-0089-8 | Apr. 3, 2021 | 3 | Apr. 6, 2021 | 13:11:00 | Apr. 6, 2021 | 13:19:00 | Negative |
| 44-37-0090-3 | Apr. 3, 2021 | 3 | Apr. 6, 2021 | 13:25:00 | Apr. 6, 2021 | 13:29:00 | Negative |
| 44-37-0091-9 | Apr. 5, 2021 | 1 | Apr. 6, 2021 | 13:47:00 | Apr. 6, 2021 | 13:53:00 | Negative |
| 44-37-0092-5 | Apr. 3, 2021 | 3 | Apr. 6, 2021 | 14:15:00 | Apr. 6, 2021 | 14:19:00 | Negative |

InBios' Smart Detect ™ SARS-CoV-2 rRT-PCR*$

| Donor ID | Rapid Test Result | rRT-PCR Testing Date | N gene | E gene | ORF1b | Rnase P | rRT-PCR Result |
|---|---|---|---|---|---|---|---|
| 42-37-0001-6 | Negative | Mar. 15, 2021 | NaN | NaN | NaN | 32.01 | Negative |
| 42-37-0002-7 | Negative | Mar. 15, 2021 | NaN | NaN | NaN | 33.14 | Negative |
| 42-37-0003-0 | Negative | Mar. 15, 2021 | NaN | NaN | NaN | 35.52 | Negative |
| 42-37-0004-3 | Negative | Mar. 15, 2021 | NaN | NaN | NaN | 34.01 | Negative |
| 42-37-0005-5 | Negative | Mar. 15, 2021 | NaN | NaN | NaN | 30.96 | Negative |
| 42-37-0006-8 | Negative | Mar. 15, 2021 | NaN | NaN | NaN | 33.42 | Negative |
| 42-37-0007-9 | Negative | Mar. 15, 2021 | NaN | NaN | NaN | 31.92 | Negative |
| 42-37-0009-2 | Negative | Mar. 15, 2021 | NaN | NaN | NaN | 33.60 | Negative |
| 42-37-0010-8 | Negative | Mar. 15, 2021 | NaN | NaN | NaN | 31.84 | Negative |
| 42-37-0011-4 | Negative | Mar. 15, 2021 | NaN | NaN | NaN | 34.22 | Negative |
| 42-37-0012-0 | Negative | Mar. 15, 2021 | NaN | NaN | NaN | 34.32 | Negative |
| 42-37-0013-7 | Negative | Mar. 15, 2021 | NaN | NaN | NaN | 32.92 | Negative |
| 42-37-0014-5 | Negative | Mar. 15, 2021 | NaN | NaN | NaN | 36.15 | Negative |
| 42-37-0015-3 | Negative | Mar. 15, 2021 | NaN | NaN | NaN | 34.46 | Negative |
| 42-37-0016-1 | Negative | Mar. 15, 2021 | NaN | NaN | NaN | 30.52 | Negative |
| 42-37-0017-2 | Negative | Mar. 15, 2021 | NaN | NaN | NaN | 33.10 | Negative |
| 42-37-0018-6 | Negative | Mar. 15, 2021 | NaN | NaN | NaN | 36.89 | Negative |
| 42-37-0019-9 | Negative | Mar. 15, 2021 | NaN | NaN | NaN | 35.18 | Negative |
| 43-37-0001-5 | Negative | Mar. 15, 2021 | NaN | NaN | NaN | 35.94 | Negative |
| 43-37-0002-6 | Negative | Mar. 15, 2021 | NaN | NaN | NaN | 34.36 | Negative |
| 43-37-0003-1 | Negative | Mar. 15, 2021 | NaN | NaN | NaN | 37.20 | Negative |
| 42-37-0021-1 | Negative | Mar. 15, 2021 | 39.94 | NaN | NaN | 32.69 | Negative |
| 42-37-0022-2 | Negative | Mar. 15, 2021 | NaN | NaN | NaN | 36.89 | Negative |
| 42-37-0023-5 | Negative | Mar. 15, 2021 | NaN | NaN | NaN | 31.69 | Negative |
| 42-37-0024-8 | Negative | Mar. 15, 2021 | NaN | NaN | NaN | 36.04 | Negative |
| 42-37-0025-0 | Negative | Mar. 15, 2021 | NaN | NaN | NaN | 35.91 | Negative |
| 42-37-0026-3 | Negative | Mar. 15, 2021 | NaN | NaN | NaN | 34.65 | Negative |
| 42-37-0027-4 | Positive | Mar. 15, 2021 | 23.33 | 21.33 | 25.86 | 37.12 | Positive |
| 43-37-0006-7 | Negative | Mar. 15, 2021 | NaN | NaN | NaN | 31.71 | Negative |
| 43-37-0005-9 | Negative | Mar. 15, 2021 | NaN | NaN | NaN | 35.98 | Negative |
| 43-37-0007-8 | Positive | Mar. 15, 2021 | 20.25 | 18.27 | 22.66 | 36.00 | Positive |
| 43-37-0008-0 | Negative | Mar. 15, 2021 | NaN | NaN | NaN | 32.36 | Negative |
| 43-37-0009-3 | Negative | Mar. 15, 2021 | NaN | NaN | NaN | 33.12 | Negative |
| 43-37-0010-7 | Negative | Mar. 15, 2021 | NaN | NaN | NaN | 34.99 | Negative |
| 43-37-0011-0 | Negative | Mar. 15, 2021 | NaN | NaN | NaN | 32.32 | Negative |
| 43-37-0012-1 | Negative | Mar. 15, 2021 | NaN | NaN | NaN | 32.12 | Negative |
| 42-37-0028-9 | Negative | Mar. 15, 2021 | NaN | NaN | NaN | 35.88 | Negative |
| 42-37-0029-7 | Negative | Mar. 15, 2021 | NaN | NaN | NaN | 34.08 | Negative |
| 42-37-0030-2 | Negative | Mar. 13, 2021 | NaN | NaN | NaN | 33.34 | Negative |
| 42-37-0031-5 | Negative | Mar. 13, 2021 | NaN | NaN | NaN | 35.44 | Negative |
| 42-37-0032-6 | Negative | Mar. 13, 2021 | NaN | NaN | NaN | 33.05 | Negative |
| 42-37-0033-1 | Negative | Mar. 13, 2021 | NaN | NaN | NaN | 33.79 | Negative |
| 42-37-0034-4 | Negative | Mar. 13, 2021 | NaN | NaN | NaN | 33.07 | Negative |
| 42-37-0035-9 | Negative | Mar. 13, 2021 | NaN | NaN | NaN | 36.16 | Negative |
| 43-37-0013-6 | Negative | Mar. 13, 2021 | NaN | NaN | NaN | 36.47 | Negative |
| 43-37-0014-9 | Negative | Mar. 13, 2021 | NaN | NaN | NaN | 35.43 | Negative |
| 43-37-0015-4 | Negative | Mar. 13, 2021 | NaN | NaN | NaN | 31.51 | Negative |
| 42-37-0038-0 | Negative | Mar. 13, 2021 | NaN | NaN | NaN | 34.05 | Negative |
| 42-37-0039-3 | Negative | Mar. 13, 2021 | NaN | NaN | NaN | 32.85 | Negative |
| 42-37-0040-7 | Negative | Mar. 13, 2021 | NaN | NaN | NaN | 32.77 | Negative |
| 44-37-0001-4 | Negative | Mar. 13, 2021 | NaN | NaN | NaN | 34.37 | Negative |
| 42-37-0036-7 | Negative | Mar. 13, 2021 | NaN | NaN | NaN | 32.73 | Negative |
| 42-37-0037-8 | Negative | Mar. 13, 2021 | NaN | NaN | NaN | 32.45 | Negative |
| 44-37-0003-7 | Negative | Mar. 13, 2021 | NaN | NaN | NaN | 33.62 | Negative |
| 44-37-0004-5 | Negative | Mar. 13, 2021 | NaN | NaN | NaN | 35.04 | Negative |
| 44-37-0005-3 | Negative | Mar. 13, 2021 | NaN | NaN | NaN | 31.84 | Negative |
| 44-37-0006-1 | Negative | Mar. 15, 2021 | NaN | NaN | NaN | 33.00 | Negative |
| 44-37-0007-2 | Negative | Mar. 15, 2021 | NaN | NaN | NaN | 33.78 | Negative |

TABLE 16-continued

Line Data for Clinical Evaluation with Prospective Samples (Sites 2a, 2b, 2c, 2d)

| | | | | | | | |
|---|---|---|---|---|---|---|---|
| 44-37-0008-6 | Negative | Mar. 15, 2021 | NaN | NaN | NaN | 33.92 | Negative |
| 44-37-0009-9 | Positive | Mar. 13, 2021 | 23.28 | 21.66 | 27.46 | 37.45 | Positive |
| 44-37-0010-1 | Negative | Mar. 13, 2021 | NaN | NaN | NaN | 30.58 | Negative |
| 44-37-0011-6 | Negative | Mar. 13, 2021 | NaN | NaN | NaN | 30.55 | Negative |
| 44-37-0012-7 | Negative | Mar. 13, 2021 | NaN | NaN | NaN | 33.57 | Negative |
| 44-37-0013-0 | Negative | Mar. 13, 2021 | NaN | NaN | NaN | 33.96 | Negative |
| 44-37-0014-3 | Negative | Mar. 23, 2021 | NaN | NaN | NaN | 34.21 | Negative |
| 44-37-0015-5 | Negative | Mar. 23, 2021 | NaN | NaN | NaN | 32.29 | Negative |
| 44-37-0017-9 | Negative | Mar. 23, 2021 | NaN | NaN | NaN | 33.11 | Negative |
| 44-37-0018-4 | Negative | Mar. 23, 2021 | NaN | NaN | NaN | 32.67 | Negative |
| 44-37-0019-2 | Negative | Mar. 23, 2021 | NaN | NaN | NaN | 34.65 | Negative |
| 44-37-0020-4 | Negative | Mar. 23, 2021 | NaN | NaN | NaN | 33.93 | Negative |
| 44-37-0021-8 | Negative | Mar. 23, 2021 | NaN | NaN | NaN | 33.17 | Negative |
| 44-37-0022-9 | Negative | Mar. 23, 2021 | NaN | NaN | NaN | 34.70 | Negative |
| 44-37-0023-3 | Negative | Mar. 23, 2021 | NaN | NaN | NaN | 34.08 | Negative |
| 44-37-0024-1 | Negative | Mar. 23, 2021 | NaN | NaN | NaN | 32.02 | Negative |
| 44-37-0025-7 | Negative | Mar. 23, 2021 | NaN | NaN | NaN | 33.56 | Negative |
| 44-37-0026-5 | Negative | Mar. 23, 2021 | NaN | NaN | NaN | 31.65 | Negative |
| 44-37-0027-6 | Negative | Mar. 23, 2021 | NaN | NaN | NaN | 33.30 | Negative |
| 44-37-0028-2 | Negative | Mar. 23, 2021 | NaN | NaN | NaN | 35.69 | Negative |
| 44-37-0029-0 | Negative | Mar. 23, 2021 | 29.30 | 27.37 | 31.08 | 33.39 | Positive |
| 44-37-0030-9 | Negative | Mar. 23, 2021 | NaN | NaN | NaN | 35.39 | Negative |
| 44-37-0031-3 | Negative | Mar. 23, 2021 | NaN | NaN | NaN | 31.85 | Negative |
| 44-37-0032-4 | Negative | Mar. 23, 2021 | NaN | NaN | NaN | 35.31 | Negative |
| 44-37-0033-8 | Negative | Mar. 23, 2021 | NaN | NaN | NaN | 33.39 | Negative |
| 44-37-0034-6 | Negative | Mar. 23, 2021 | NaN | NaN | NaN | 36.11 | Negative |
| 44-37-0035-2 | Negative | Mar. 30, 2021 | NaN | NaN | NaN | 33.09 | Negative |
| 44-37-0036-0 | Negative | Mar. 30, 2021 | NaN | NaN | NaN | 32.57 | Negative |
| 44-37-0037-1 | Negative | Mar. 30, 2021 | NaN | NaN | NaN | 31.48 | Negative |
| 44-37-0038-7 | Negative | Mar. 30, 2021 | NaN | NaN | NaN | 32.18 | Negative |
| 44-37-0040-0 | Negative | Mar. 30, 2021 | 30.08 | 30.04 | 36.96 | 31.08 | Positive |
| 44-37-0041-7 | Negative | Mar. 30, 2021 | NaN | NaN | NaN | 28.65 | Negative |
| 44-37-0048-3 | Positive | Apr. 7, 2021 | 16.53 | 12.06 | 19.34 | 32.86 | Positive |
| 44-37-0047-5 | Negative | Mar. 30, 2021 | NaN | NaN | NaN | 31.05 | Negative |
| 44-37-0049-1 | Negative | Apr. 7, 2021 | 33.60 | 33.14 | NaN | 33.78 | Positive |
| 44-37-0050-6 | Negative | Apr. 7, 2021 | NaN | NaN | NaN | 35.06 | Negative |
| 44-37-0052-2 | Negative | Apr. 7, 2021 | NaN | NaN | NaN | 32.17 | Negative |
| 44-37-0053-5 | Negative | Apr. 7, 2021 | NaN | NaN | NaN | 31.88 | Negative |
| 44-37-0055-0 | Positive | Apr. 7, 2021 | 22.30 | 21.22 | 28.14 | 32.78 | Positive |
| 44-37-0056-3 | Negative | Apr. 7, 2021 | NaN | NaN | NaN | 32.20 | Negative |
| 44-37-0057-4 | Negative | Apr. 6, 2021 | NaN | NaN | NaN | 32.03 | Negative |
| 44-37-0058-9 | Negative | Apr. 7, 2021 | NaN | NaN | NaN | 33.65 | Negative |
| 44-37-0059-7 | Negative | Apr. 7, 2021 | NaN | NaN | NaN | 36.26 | Negative |
| 44-37-0060-2 | Negative | Apr. 7, 2021 | NaN | NaN | NaN | 33.55 | Negative |
| 44-37-0061-5 | Negative | Apr. 7, 2021 | NaN | NaN | NaN | 33.17 | Negative |
| 44-37-0062-6 | Positive | Apr. 7, 2021 | 38.82 | 37.00 | NaN | 31.40 | Positive |
| 44-37-0063-1 | Positive | Apr. 7, 2021 | 18.46 | 16.70 | 22.29 | 33.56 | Positive |
| 44-37-0064-4 | Positive | Apr. 7, 2021 | 21.75 | 19.34 | 25.21 | 33.21 | Positive |
| 44-37-0066-7 | Negative | Apr. 9, 2021 | NaN | NaN | NaN | 31.35 | Negative |
| 44-37-0065-9 | Negative | Apr. 7, 2021 | NaN | NaN | NaN | 31.69 | Negative |
| 44-37-0067-8 | Negative | Apr. 9, 2021 | 31.02 | 30.36 | NaN | 30.33 | Positive |
| 44-37-0068-0 | Negative | Apr. 9, 2021 | NaN | NaN | NaN | 31.31 | Negative |
| 44-37-0069-3 | Negative | Apr. 9, 2021 | NaN | NaN | NaN | 30.79 | Negative |
| 44-37-0071-2 | Negative | Apr. 9, 2021 | NaN | NaN | NaN | 30.93 | Negative |
| 44-37-0070-5 | Positive | Apr. 9, 2021 | 21.17 | 19.45 | 24.15 | 32.42 | Positive |
| 44-37-0072-3 | Positive | Apr. 9, 2021 | 21.76 | 21.00 | 26.26 | 32.12 | Positive |
| 44-37-0073-9 | Negative | Apr. 9, 2021 | NaN | NaN | NaN | 33.42 | Negative |
| 45-37-0001-7 | Negative | Mar. 23, 2021 | NaN | NaN | NaN | 32.68 | Negative |
| 45-37-0002-8 | Negative | Mar. 30, 2021 | NaN | NaN | NaN | 32.13 | Negative |
| 45-37-0003-4 | Negative | Mar. 30, 2021 | NaN | NaN | NaN | 38.48 | Negative |
| 45-37-0004-2 | Positive | Mar. 30, 2021 | 24.42 | 25.50 | 30.07 | 36.37 | Positive |
| 45-37-0005-6 | Positive | Mar. 30, 2021 | 29.06 | 30.29 | 35.91 | 30.20 | Positive |
| 45-37-0006-9 | Negative | Mar. 30, 2021 | 19.79 | 20.01 | 23.62 | 33.78 | Positive |
| 45-37-0007-5 | Positive | Mar. 30, 2021 | 22.33 | 22.41 | 26.16 | 33.59 | Positive |
| 45-37-0008-3 | Negative | Mar. 30, 2021 | NaN | NaN | NaN | 32.18 | Negative |
| 45-37-0009-1 | Negative | Mar. 30, 2021 | NaN | NaN | NaN | 32.76 | Negative |
| 45-37-0010-9 | Negative | Mar. 30, 2021 | NaN | NaN | NaN | 30.64 | Negative |
| 44-37-0039-5 | Negative | Mar. 30, 2021 | NaN | NaN | NaN | 34.28 | Negative |
| 44-37-0042-8 | Negative | Mar. 30, 2021 | NaN | NaN | NaN | 31.59 | Negative |
| 44-37-0043-4 | Negative | Mar. 30, 2021 | NaN | NaN | NaN | 31.10 | Negative |
| 44-37-0044-2 | Negative | Mar. 30, 2021 | NaN | NaN | NaN | 31.09 | Negative |
| 44-37-0045-6 | Negative | Mar. 30, 2021 | NaN | NaN | NaN | 34.02 | Negative |
| 44-37-0046-9 | Negative | Mar. 30, 2021 | NaN | NaN | NaN | 33.17 | Negative |
| 45-37-0012-4 | Negative | Apr. 6, 2021 | NaN | NaN | NaN | 35.22 | Negative |
| 45-37-0013-8 | Negative | Apr. 6, 2021 | NaN | NaN | NaN | 32.97 | Negative |
| 45-37-0014-6 | Negative | Apr. 6, 2021 | NaN | NaN | NaN | 35.17 | Negative |
| 45-37-0015-2 | Negative | Apr. 6, 2021 | NaN | NaN | NaN | 39.42 | Negative |
| 45-37-0016-0 | Negative | Apr. 6, 2021 | NaN | NaN | NaN | 33.90 | Negative |

TABLE 16-continued

Line Data for Clinical Evaluation with Prospective Samples (Sites 2a, 2b, 2c, 2d)

| | | | | | | | |
|---|---|---|---|---|---|---|---|
| 45-37-0017-1 | Negative | Apr. 6, 2021 | NaN | NaN | NaN | 32.35 | Negative |
| 45-37-0018-7 | Negative | Apr. 6, 2021 | NaN | NaN | NaN | 33.24 | Negative |
| 45-37-0019-5 | Negative | Apr. 6, 2021 | NaN | NaN | NaN | 31.87 | Negative |
| 45-37-0020-7 | Negative | Apr. 6, 2021 | NaN | NaN | NaN | 30.72 | Negative |
| 45-37-0021-0 | Negative | Apr. 6, 2021 | NaN | NaN | NaN | 32.66 | Negative |
| 45-37-0022-1 | Negative | Apr. 6, 2021 | NaN | NaN | NaN | 32.48 | Negative |
| 45-37-0023-6 | Negative | Apr. 6, 2021 | NaN | NaN | NaN | 31.90 | Negative |
| 45-37-0024-9 | Negative | Apr. 6, 2021 | NaN | NaN | NaN | 38.55 | Negative |
| 45-37-0025-4 | Negative | Apr. 6, 2021 | NaN | NaN | NaN | 32.48 | Negative |
| 45-37-0026-2 | Negative | Apr. 6, 2021 | NaN | NaN | NaN | 32.92 | Negative |
| 45-37-0027-3 | Negative | Apr. 6, 2021 | NaN | NaN | NaN | 33.94 | Negative |
| 45-37-0028-5 | Negative | Apr. 9, 2021 | NaN | NaN | NaN | 32.09 | Negative |
| 45-37-0029-8 | Negative | Apr. 9, 2021 | NaN | NaN | NaN | 28.17 | Negative |
| 45-37-0030-1 | Positive | Apr. 9, 2021 | 22.76 | 21.86 | 27.28 | 29.54 | Positive |
| 45-37-0031-6 | Positive | Apr. 9, 2021 | 21.77 | 20.45 | 25.70 | 33.72 | Positive |
| 45-37-0032-7 | Positive | Apr. 9, 2021 | 25.09 | 23.56 | 28.68 | 30.00 | Positive |
| 45-37-0033-0 | Negative | Apr. 9, 2021 | NaN | 42.32 | NaN | 32.08 | Negative |
| 45-37-0035-5 | Negative | Apr. 9, 2021 | NaN | NaN | NaN | 34.26 | Negative |
| 45-37-0036-8 | Positive | Apr. 9, 2021 | 20.99 | 19.68 | 24.08 | 32.66 | Positive |
| 45-37-0037-9 | Negative | Apr. 9, 2021 | NaN | NaN | NaN | 31.39 | Negative |
| 45-37-0038-4 | Negative | Apr. 9, 2021 | NaN | NaN | NaN | 34.30 | Negative |
| 45-37-0039-2 | Positive | Apr. 9, 2021 | 22.62 | 21.29 | 26.10 | 33.22 | Positive |
| 44-37-0074-7 | Positive | Apr. 9, 2021 | 22.67 | 20.58 | 25.62 | 30.12 | Positive |
| 44-37-0075-1 | Negative | Apr. 9, 2021 | 42.38 | 40.24 | NaN | 31.43 | Negative |
| 44-37-0076-4 | Positive | Apr. 9, 2021 | 20.05 | 18.69 | 24.20 | 31.06 | Positive |
| 44-37-0077-0 | Negative | Apr. 9, 2021 | NaN | NaN | NaN | 29.93 | Negative |
| 44-37-0078-8 | Negative | Apr. 9, 2021 | NaN | NaN | NaN | 32.27 | Negative |
| 44-37-0079-6 | Negative | Apr. 9, 2021 | NaN | NaN | NaN | 33.96 | Negative |
| 44-37-0080-7 | Negative | Apr. 9, 2021 | NaN | NaN | NaN | 32.17 | Negative |
| 44-37-0081-0 | Negative | Apr. 9, 2021 | NaN | NaN | NaN | 32.05 | Negative |
| 44-37-0082-1 | Negative | Apr. 9, 2021 | NaN | NaN | NaN | 33.42 | Negative |
| 44-37-0083-6 | Positive | Apr. 9, 2021 | 22.11 | 20.40 | 25.64 | 38.13 | Positive |
| 44-37-0084-9 | Positive | Apr. 9, 2021 | 20.48 | 18.61 | 23.36 | 37.47 | Positive |
| 44-37-0085-4 | Negative | Apr. 9, 2021 | NaN | NaN | NaN | 30.48 | Negative |
| 44-37-0086-2 | Negative | Apr. 9, 2021 | NaN | NaN | NaN | 32.03 | Negative |
| 44-37-0087-3 | Positive | Apr. 9, 2021 | 23.91 | 21.64 | 27.51 | 32.85 | Positive |
| 44-37-0088-5 | Negative | Apr. 9, 2021 | NaN | NaN | NaN | 30.95 | Negative |
| 44-37-0089-8 | Negative | Apr. 9, 2021 | NaN | NaN | NaN | 31.52 | Negative |
| 44-37-0090-3 | Negative | Apr. 9, 2021 | NaN | NaN | NaN | 29.47 | Negative |
| 44-37-0091-9 | Negative | Apr. 9, 2021 | NaN | NaN | NaN | 31.77 | Negative |
| 44-37-0092-5 | Negative | Apr. 9, 2021 | NaN | NaN | NaN | 39.14 | Negative |

TABLE 17

Line Data for Clinical Evaluation with Prospective Samples (Site 3)

| | | | Sample | InBios SCoV-2 Ag Detect ™$ | |
|---|---|---|---|---|---|
| Donor ID | Symptom Onset Date | Days PSO | Collection Date/Time | Rapid Test Date/Time | Rapid Test Result |
| Subject-002 | Mar. 5, 2021 | 5 | 2021 Mar. 10 11:33:00 | 2021 Mar. 10 11:34:00 | Positive |
| Subject-003 | Mar. 6, 2021 | 4 | 2021 Mar. 10 13:06:00 | 2021 Mar. 10 13:08:34 | Negative |
| Subject-005 | Mar. 5, 2021 | 5 | 2021 Mar. 10 12:53:00 | 2021 Mar. 10 12:51:00 | Negative |
| Subject-006 | Mar. 5, 2021 | 5 | 2021 Mar. 10 13:26:11 | 2021 Mar. 10 13:28:38 | Negative |
| Subject-007 | Mar. 8, 2021 | 2 | 2021 Mar. 10 13:47:00 | 2021 Mar. 10 13:48:00 | Negative |
| Subject-008 | Mar. 7, 2021 | 3 | 2021 Mar. 10 12:50:00 | 2021 Mar. 10 13:37:00 | Negative |
| Subject-009 | Mar. 5, 2021 | 5 | 2021 Mar. 10 13:17:00 | 2021 Mar. 10 13:18:00 | Negative |
| Subject-010 | Mar. 6, 2021 | 4 | 2021 Mar. 10 15:34:00 | 2021 Mar. 10 15:37:00 | Negative |
| Subject-012 | Mar. 8, 2021 | 2 | 2021 Mar. 10 15:27:00 | 2021 Mar. 10 15:30:00 | Negative |
| Subject-013 | Mar. 8, 2021 | 3 | 2021 Mar. 11 09:03:16 | 2021 Mar. 11 09:05:42 | Negative |
| Subject-014 | Mar. 6, 2021 | 5 | 2021 Mar. 11 23:49:00 | 2021 Mar. 11 12:00:00 | Negative |
| Subject-016 | Mar. 8, 2021 | 3 | 2021 Mar. 11 12:48:00 | 2021 Mar. 11 12:42:00 | Negative |

TABLE 17-continued

Line Data for Clinical Evaluation with Prospective Samples (Site 3)

| | | | | | |
|---|---|---|---|---|---|
| Subject-017 | Mar. 9, 2021 | 2 | 2021 Mar. 11 12:50:06.862 | 2021 Mar. 11 12:52:00 | Negative |
| Subject-018 | Mar. 7, 2021 | 4 | 2021 Mar. 11 13:58:00 | 2021 Mar. 11 14:00:00 | Negative |
| Subject-021 | Mar. 8, 2021 | 3 | 2021 Mar. 11 14:13:00 | 2021 Mar. 11 14:15:00 | Positive |
| Subject-022^ | Mar. 6, 2021 | 5 | 2021 Mar. 11 15:15:00 | 2021 Mar. 11 15:18:00 | Negative |
| Subject-023 | Mar. 11, 2021 | 1 | 2021 Mar. 12 10:33:00 | 2021 Mar. 12 10:35:00 | Negative |
| Subject-024 | Mar. 9, 2021 | 3 | 2021 Mar. 12 14:45:00 | 2021 Mar. 12 14:45:00 | Negative |
| Subject-026 | Mar. 9, 2021 | 3 | 2021 Mar. 12 11:45:00 | 2021 Mar. 12 11:49:00 | Negative |
| Subject-027 | Mar. 10, 2021 | 2 | 2021 Mar. 12 11:43:00 | 2021 Mar. 12 11:45:00 | Negative |
| Subject-028 | Mar. 10, 2021 | 2 | 2021 Mar. 12 12:01:00 | 2021 Mar. 12 00:03:00 | Negative |
| Subject-029 | Mar. 10, 2021 | 2 | 2021 Mar. 12 12:58:00 | 2021 Mar. 12 12:59:00 | Negative |
| Subject-030 | Mar. 10, 2021 | 2 | 2021 Mar. 12 13:55:00 | 2021 Mar. 12 13:57:00 | Negative |
| Subject-031 | Mar. 11, 2021 | 1 | 2021 Mar. 12 14:09:00 | 2021 Mar. 12 14:10:00 | Negative |
| Subject-032 | Mar. 11, 2021 | 1 | 2021 Mar. 12 14:05:00 | 2021 Mar. 12 14:09:00 | Negative |
| Subject-033 | Mar. 12, 2021 | 3 | 2021 Mar. 15 09:22:00 | 2021 Mar. 15 09:23:00 | Negative |
| Subject-034 | Mar. 12, 2021 | 3 | 2021 Mar. 15 10:30:23.61 | 2021 Mar. 15 10:33:00 | Negative |
| Subject-035 | Mar. 10, 2021 | 5 | 2021 Mar. 15 13:45:00 | 2021 Mar. 15 13:46:00 | Negative |
| Subject-036 | Mar. 13, 2021 | 2 | 2021 Mar. 15 13:10:00 | 2021 Mar. 15 13:11:00 | Negative |
| Subject-038 | Mar. 13, 2021 | 2 | 2021 Mar. 15 14:24:00 | 2021 Mar. 15 14:25:00 | Negative |
| Subject-039 | Mar. 13, 2021 | 2 | 2021 Mar. 15 13:54:00 | 2021 Mar. 15 13:55:00 | Negative |
| Subject-040 | Mar. 13, 2021 | 2 | 2021 Mar. 15 15:25:00 | 2021 Mar. 15 15:26:00 | Negative |
| Subject-041 | Mar. 10, 2021 | 5 | 2021 Mar. 15 16:15:00 | 2021 Mar. 15 16:15:00 | Negative |
| Subject-042 | Mar. 12, 2021 | 3 | 2021 Mar. 15 15:38:00 | 2021 Mar. 15 15:40:00 | Negative |
| Subject-043 | Mar. 12, 2021 | 3 | 2021 Mar. 15 16:39:00 | 2021 Mar. 15 16:40:00 | Negative |
| Subject-045 | Mar. 13, 2021 | 3 | 2021 Mar. 16 09:55:00 | 2021 Mar. 16 09:57:00 | Negative |
| Subject-046 | Mar. 14, 2021 | 2 | 2021 Mar. 16 10:13:00 | 2021 Mar. 16 10:15:00 | Negative |
| Subject-047 | Mar. 13, 2021 | 3 | 2021 Mar. 16 10:52:00 | 2021 Mar. 16 10:54:00 | Positive |
| Subject-048 | Mar. 13, 2021 | 3 | 2021 Mar. 16 23:37:00 | 2021 Mar. 16 23:39:00 | Positive |
| Subject-049 | Mar. 13, 2021 | 3 | 2021 Mar. 16 14:37:00 | 2021 Mar. 16 14:38:00 | Negative |
| Subject-050 | Mar. 12, 2021 | 4 | 2021 Mar. 16 15:28:00 | 2021 Mar. 16 15:30:00 | Positive |
| Subject-051 | Mar. 13, 2021 | 3 | 2021 Mar. 16 15:45:00 | 2021 Mar. 16 15:49:00 | Positive |
| Subject-052 | Mar. 15, 2021 | 1 | 2021 Mar. 16 15:09:00 | 2021 Mar. 16 15:00:00 | Negative |
| Subject-053 | Mar. 14, 2021 | 3 | 2021 Mar. 17 10:20:00 | 2021 Mar. 17 10:22:00 | Negative |
| Subject-054 | Mar. 12, 2021 | 5 | 2021 Mar. 17 10:51:00 | 2021 Mar. 17 10:52:00 | Negative |
| Subject-055 | Mar. 12, 2021 | 5 | 2021 Mar. 17 10:47:00 | 2021 Mar. 17 10:48:00 | Negative |
| Subject-056 | Mar. 14, 2021 | 3 | 2021 Mar. 17 11:00:00 | 2021 Mar. 17 11:01:00 | Positive |
| Subject-057 | Mar. 16, 2021 | 1 | Mar. 17, 2021 11:14 | 2021 Mar. 17 11:15:00 | Negative |
| Subject-058 | Mar. 13, 2021 | 4 | 2021 Mar. 17 12:11:00 | 2021 Mar. 17 12:11:00 | Positive |
| Subject-059 | Mar. 14, 2021 | 3 | 2021 Mar. 17 15:39:00 | 2021 Mar. 17 15:40:00 | Negative |
| Subject-060 | Mar. 23, 2021 | 1 | 2021 Mar. 24 12:05:00 | 2021 Mar. 24 12:07:00 | Positive |

TABLE 17-continued

Line Data for Clinical Evaluation with Prospective Samples (Site 3)

| Subject-061 | Mar. 22, 2021 | 2 | 2021 Mar. 24 14:36:00 | 2021 Mar. 24 14:37:00 | Negative |
|---|---|---|---|---|---|
| Subject-062 | Mar. 23, 2021 | 2 | 2021 Mar. 25 12:40:00 | 2021 Mar. 25 12:41:00 | Negative |
| Subject-063 | Mar. 23, 2021 | 2 | Mar. 25, 2021 13:00 | 2021 Mar. 25 13:00:00 | Negative |
| Subject-064 | Mar. 25, 2021 | 0 | 2021 Mar. 25 12:50:00 | Mar. 25, 2021 12:53 | Negative |
| Subject-065 | Mar. 21, 2021 | 4 | 2021 Mar. 25 13:19:00 | 2021 Mar. 25 13:20:00 | Positive |
| Subject-066^ | Mar. 25, 2021 | 0 | 2021 Mar. 25 13:29:00 | 2021 Mar. 25 13:30:00 | Negative |
| Subject-067 | Mar. 20, 2021 | 5 | 2021 Mar. 25 13:45:00 | 2021 Mar. 25 13:46:00 | Positive |
| Subject-068 | Mar. 23, 2021 | 2 | 2021 Mar. 25 14:17:00 | 2021 Mar. 25 14:18:00 | Positive |
| Subject-069 | Mar. 22, 2021 | 4 | 2021 Mar. 26 23:49:00 | 2021 Mar. 26 11:50:00 | Negative |
| Subject-070 | Mar. 21, 2021 | 5 | 2021 Mar. 26 12:33:00 | 2021 Mar. 26 12:34:00 | Negative |
| Subject-071 | Mar. 24, 2021 | 2 | 2021 Mar. 26 12:35:00 | 2021 Mar. 26 12:36:00 | Negative |
| Subject-072 | Mar. 25, 2021 | 1 | 2021 Mar. 26 13:05:00 | 2021 Mar. 26 13:05:00 | Negative |
| Subject-073 | Mar. 24, 2021 | 2 | 2021 Mar. 26 13:08:00 | 2021 Mar. 26 13:09:00 | Negative |
| Subject-074 | Mar. 24, 2021 | 2 | 2021 Mar. 26 13:54:00 | 2021 Mar. 26 13:55:00 | Negative |
| Subject-075 | Mar. 23, 2021 | 3 | 2021 Mar. 26 15:48:00 | 2021 Mar. 26 15:50:00 | Positive |
| Subject-076 | Mar. 27, 2021 | 2 | 2021 Mar. 29 15:15:00 | 2021 Mar. 29 15:16:00 | Negative |
| Subject-077 | Mar. 26, 2021 | 3 | 2021 Mar. 29 15:13:00 | 2021 Mar. 29 15:15:00 | Negative |
| Subject-078 | Mar. 27, 2021 | 2 | 2021 Mar. 29 15:26:00 | 2021 Mar. 29 15:28:00 | Negative |
| Subject-083 | Mar. 27, 2021 | 3 | Mar. 30, 2021 13:46 | Mar. 30, 2021 13:47 | Negative |
| Subject-084 | Mar. 26, 2021 | 4 | 2021 Mar. 30 13:49:00 | 2021 Mar. 30 13:50:00 | Positive |
| Subject-086 | Mar. 29, 2021 | 2 | 2021 Mar. 31 13:58:00 | 2021 Mar. 31 13:59:00 | Negative |

| InBios' Smart Detect ™ SARS-CoV-2 rRT-PCR*$ | | | | | |
|---|---|---|---|---|---|
| Donor ID | rRT-PCR Testing Date | N gene | E gene | ORF1b | Rnase P | rRT-PCR Result |
| Subject-002 | Mar. 22, 2021 | 25.42 | 23.80 | 28.20 | 36.60 | Positive |
| Subject-003 | Mar. 22, 2021 | NaN | NaN | NaN | 34.36 | Negative |
| Subject-005 | Mar. 22, 2021 | NaN | NaN | NaN | 33.27 | Negative |
| Subject-006 | Mar. 22, 2021 | NaN | NaN | NaN | 34.19 | Negative |
| Subject-007 | Mar. 22, 2021 | NaN | NaN | NaN | 34.56 | Negative |
| Subject-008 | Mar. 22, 2021 | NaN | NaN | NaN | 35.55 | Negative |
| Subject-009 | Mar. 22, 2021 | 33.70 | 34.26 | NaN | 33.44 | Positive |
| Subject-010 | Mar. 22, 2021 | NaN | NaN | NaN | 35.69 | Negative |
| Subject-012 | Mar. 22, 2021 | NaN | NaN | NaN | 33.17 | Negative |
| Subject-013 | Mar. 22, 2021 | NaN | NaN | NaN | 35.26 | Negative |
| Subject-014 | Mar. 22, 2021 | NaN | NaN | NaN | 33.03 | Negative |
| Subject-016 | Mar. 22, 2021 | NaN | NaN | NaN | 34.29 | Negative |
| Subject-017 | Mar. 22, 2021 | NaN | NaN | NaN | 36.10 | Negative |
| Subject-018 | Mar. 22, 2021 | NaN | NaN | NaN | 35.76 | Negative |
| Subject-021 | Mar. 22, 2021 | 25.20 | 25.19 | 29.57 | 31.05 | Positive |
| Subject-022^ | Mar. 22, 2021 | NaN | NaN | NaN | 35.04 | Negative |
| Subject-023 | Mar. 22, 2021 | NaN | NaN | NaN | NaN | Invalid |
| Subject-024 | Mar. 22, 2021 | NaN | NaN | NaN | 31.65 | Negative |
| Subject-026 | Mar. 22, 2021 | NaN | NaN | NaN | 35.79 | Negative |
| Subject-027 | Mar. 22, 2021 | NaN | NaN | NaN | 33.08 | Negative |
| Subject-028 | Mar. 19, 2021 | NaN | NaN | NaN | 36.24 | Negative |
| Subject-029 | Mar. 19, 2021 | NaN | NaN | NaN | 34.18 | Negative |
| Subject-030 | Mar. 19, 2021 | NaN | NaN | NaN | 38.41 | Negative |
| Subject-031 | Mar. 19, 2021 | NaN | NaN | NaN | 36.54 | Negative |
| Subject-032 | Mar. 19, 2021 | NaN | NaN | NaN | 34.06 | Negative |
| Subject-033 | Mar. 19, 2021 | NaN | NaN | NaN | 36.16 | Negative |

TABLE 17-continued

Line Data for Clinical Evaluation with Prospective Samples (Site 3)

| Subject | Date | | | | | Result |
|---|---|---|---|---|---|---|
| Subject-034 | Mar. 19, 2021 | NaN | NaN | NaN | 32.39 | Negative |
| Subject-035 | Mar. 19, 2021 | NaN | NaN | NaN | 34.95 | Negative |
| Subject-036 | Mar. 19, 2021 | NaN | NaN | NaN | 34.75 | Negative |
| Subject-038 | Mar. 19, 2021 | NaN | NaN | NaN | 34.39 | Negative |
| Subject-039 | Mar. 19, 2021 | NaN | NaN | NaN | 33.82 | Negative |
| Subject-040 | Mar. 19, 2021 | NaN | NaN | NaN | 39.33 | Negative |
| Subject-041 | Mar. 19, 2021 | NaN | NaN | NaN | 31.80 | Negative |
| Subject-042 | Mar. 19, 2021 | NaN | NaN | NaN | 32.30 | Negative |
| Subject-043 | Mar. 19, 2021 | NaN | NaN | NaN | 35.31 | Negative |
| Subject-045 | Mar. 19, 2021 | NaN | NaN | NaN | 34.21 | Negative |
| Subject-046 | Mar. 19, 2021 | NaN | NaN | NaN | 36.36 | Negative |
| Subject-047 | Mar. 19, 2021 | 24.37 | 24.05 | 31.03 | 32.95 | Positive |
| Subject-048 | Mar. 19, 2021 | 22.30 | 21.46 | 27.90 | 33.88 | Positive |
| Subject-049 | Mar. 19, 2021 | NaN | NaN | NaN | 33.84 | Negative |
| Subject-050 | Mar. 19, 2021 | 20.03 | 18.95 | 25.62 | 33.39 | Positive |
| Subject-051 | Mar. 19, 2021 | 22.01 | 21.15 | 27.16 | 33.29 | Positive |
| Subject-052 | Mar. 19, 2021 | NaN | NaN | NaN | 32.94 | Negative |
| Subject-053 | Mar. 24, 2021 | NaN | NaN | NaN | 33.69 | Negative |
| Subject-054 | Mar. 24, 2021 | NaN | NaN | NaN | 33.40 | Negative |
| Subject-055 | Mar. 24, 2021 | NaN | NaN | NaN | 34.49 | Negative |
| Subject-056 | Mar. 24, 2021 | 23.02 | 21.46 | 26.10 | 33.81 | Positive |
| Subject-057 | Mar. 24, 2021 | NaN | NaN | NaN | 33.01 | Negative |
| Subject-058 | Mar. 24, 2021 | 21.27 | 19.32 | 24.73 | 34.43 | Positive |
| Subject-059 | Mar. 24, 2021 | NaN | NaN | NaN | 34.25 | Negative |
| Subject-060 | Apr. 2, 2021 | 30.28 | 29.18 | 37.49 | 32.16 | Positive |
| Subject-061 | Apr. 2, 2021 | NaN | NaN | NaN | 31.41 | Negative |
| Subject-062 | Apr. 2, 2021 | NaN | NaN | NaN | 33.27 | Negative |
| Subject-063 | Apr. 2, 2021 | NaN | NaN | NaN | 33.63 | Negative |
| Subject-064 | Apr. 2, 2021 | NaN | NaN | NaN | 35.45 | Negative |
| Subject-065 | Apr. 2, 2021 | 23.37 | 21.71 | 26.12 | 34.14 | Positive |
| Subject-066^ | Apr. 2, 2021 | NaN | NaN | NaN | 39.52 | Negative |
| Subject-067 | Apr. 2, 2021 | 24.39 | 23.66 | 29.21 | 30.26 | Positive |
| Subject-068 | Apr. 2, 2021 | 23.09 | 22.86 | 28.80 | 29.26 | Positive |
| Subject-069 | Apr. 2, 2021 | NaN | NaN | NaN | 33.13 | Negative |
| Subject-070 | Apr. 2, 2021 | NaN | NaN | NaN | 31.86 | Negative |
| Subject-071 | Apr. 2, 2021 | NaN | NaN | NaN | 31.46 | Negative |
| Subject-072 | Apr. 2, 2021 | NaN | NaN | NaN | 35.41 | Negative |
| Subject-073 | Apr. 2, 2021 | NaN | NaN | NaN | 31.52 | Negative |
| Subject-074 | Apr. 2, 2021 | NaN | NaN | NaN | 35.62 | Negative |
| Subject-075 | Apr. 2, 2021 | 21.10 | 19.23 | 23.92 | 34.56 | Positive |
| Subject-076 | Apr. 2, 2021 | NaN | NaN | NaN | 32.12 | Negative |
| Subject-077 | Apr. 2, 2021 | NaN | NaN | NaN | 32.04 | Negative |
| Subject-078 | Apr. 2, 2021 | NaN | NaN | NaN | 34.45 | Negative |
| Subject-083 | Apr. 2, 2021 | NaN | NaN | NaN | 37.10 | Negative |
| Subject-084 | Apr. 2, 2021 | 27.97 | 26.66 | 31.17 | 30.47 | Positive |
| Subject-086 | Apr. 2, 2021 | NaN | NaN | NaN | 32.22 | Negative |

*rRT-PCR results show Ct values for SARS-CoV-2 genes N, E, ORF1b as well as control gene RNase P. Ct < 40 is considered positive for a target gene/region, and PCR result is based on composite analysis of Ct values for all 4 targets per instructions for use for EUA200180. "NaN" denotes that the target was not detected.

$Paired anterior nares (nasal) swab specimens were collected for Ag Rapid Test and for rRT-PCR. Nasal swab specimens for Ag Rapid Test were collected dry. Nasal swab specimens for rRT-PCR were collected in phosphate-buffered saline at Site #1 and in CDC-recommended formulation of VTM (Innovative Research; C#IGVTM500ML) at Sites #2 and #3.

^For site #3 subject-022 and subject-066, rapid test results were read at 30 minutes instead of 20-25 minutes.

The overall PPA of SCoV-2 Ag Detect™ Rapid Test for all confirmed positive specimens collected within 5 days pso is 86.67% ($^{39}/_{45}$, 95% CI: 73.82%-93.74%). The overall NPA of SCoV-2 Ag Detect™ Rapid Test for the confirmed negative specimens collected within 5 days pso is 100.00% (257/257, 95% CI: 98.53%-100.00%). One specimen was interpreted as invalid on InBios' Smart Detect™ SARS-CoV-2 rRT-PCR Kit and thus this patient (Subject-023 from Site #3) is not included in the analysis.

TABLE 18

SCoV-2 Ag Detect ™ Rapid Test performance of anterior nares swab collected within 5 days of symptoms onset

| | | RT-PCR | | |
|---|---|---|---|---|
| | | Positive | Negative | Total |
| 2 Ag Detect ™ Rapid Test | Positive | 39 | 0 | 39 |
| | Negative | 6 | 257 | 263 |
| | Total | 45 | 257 | 302 |

67% (39/45, 95% CI: 73.82%-93.74%) NPA: 100.00% (257/257, 95% CI: 98.53%-100.00%)

PPA is further stratified by cumulative days pso, and prevalence shown by subjects' age range in the tables below.

TABLE 19

Observed PPA by cumulative days post symptoms onset (pso)

| Days PSO | Cumulative RT-PCR Confirmed Positive | Cumulative SCoV-2 Ag Detect™ Rapid Test Positive | PPA (95% Confidence interval) |
|---|---|---|---|
| 0 | 0 | 0 | NA |
| 1 | 8 | 7 | 87.50% (52.91%-97.76%) |
| 2 | 14 | 12 | 85.71% (60.06%-95.99%) |
| 3 | 30 | 26 | 86.67% (70.32%-94.69%) |
| 4 | 41 | 36 | 87.80% (74.46%-94.68%) |
| 5 | 45 | 39 | 86.67% (73.82%-93.74%) |

TABLE 20

Prevalence by subject age (age reported for 38 out of 39 positives)

| Age (years) | Total number | Number positive on SCoV-2 Ag Detect™ Rapid Test | Prevalence |
|---|---|---|---|
| 18-29 | 116 | 13 | 11.21% |
| 30-39 | 98 | 11 | 11.22% |
| 40-72 | 83 | 14 | 16.87% |

The following data is provided for informational purposes: The performance of SCoV-2 Ag Detect™ Rapid Test with positive results stratified by the comparator method cycle threshold (Ct) counts were collected and assessed to better understand the correlation of assay performance to the cycle threshold, estimating the viral titer present in the clinical sample. As presented in the table below, the positive agreement of the SCoV-2 Ag Detect™ Rapid Test is higher with samples of a lower Ct count.

TABLE 21

Observed PPA by Ct values for N gene

| Ct (N gene) | Cumulative RT-PCR Confirmed Positive | Cumulative SCoV-2 Ag Detect™ Rapid Test Positive | PPA (95% Confidence interval) |
|---|---|---|---|
| <31 | 41 | 38 | 92.68% (80.57%-97.48%) |
| <33 | 42 | 38 | 90.48% (77.93%-96.23%) |

The prospective clinical study for the SCoV-2 Ag Detect™ Rapid Test was conducted at three sites representing six POC drive through testing locations. NPA is 100.0% (95% CI: 98.53%-100.00%) and the PPA is 86.67% (95% CI: 73.82%-93.74%) for nasal swab samples collected from 302 symptomatic patients within 5 days pso.

POC Evaluation of Contrived Samples Near LoD

The purpose of POC evaluation of contrived samples was to assess performance of SCoV-2 Ag Detect™ Rapid Test on samples near limit of detection (LoD) when performed by minimally trained operators in a POC setting. Results from contrived samples supplement the testing of natural specimens described above in the prospective clinical evaluation. Contrived samples consisted of pooled nasal swab matrix, with or without addition of inactivated SARS-CoV-2 virus at concentrations ~2×LoD (i.e. ~1.3E+04 $TCID_{50}$/mL). Gamma-irradiated, SARS-Related Coronavirus 2 (SARS-CoV-2), USA-WA1/2020 isolate was obtained from Zeptometrix (RD2872, Cat. 0810587UV, Lot 325796). Prior to pooling, the nasal swab matrix specimens were screened to confirm lack of background reactivity on the SCoV-2 Ag Detect™ Rapid Test. Contrived samples were absorbed onto swabs. Samples were generated, randomized, and blinded by InBios personnel.

Testing of the randomized, blinded, contrived samples was performed at Site #3 (COVID-19 Clinic drive through site, 5601 Grossmont Center Drive, La Mesa, Calif. 91942). Five minimally trained operators tested 15 low positive and 15 negative contrived nasal swab specimens such that each operator tested 3 positive and 3 negative specimens in a blinded fashion, as part of their typical clinical workflow. The operators ran the assay in accordance with the IFU and/or QRI, and were provided no additional training.

The assay results were recorded on the study report forms and forwarded to InBios International for unblinding and analysis.

Line data are shown below. Testing of contrived low positive and negative samples by minimally trained operators at POC resulted in PPA=100% (15/15, 95% CI: 79.61%-100%) and NPA=100% (15/15, 95% CI: 79.61%-100%).

TABLE 22

Line data for POC Evaluation with Contrived Samples

| Operator | Blinded Sample ID | Contrived Sample Expected Result | InBios SCoV-2 Ag Detect™ Interpretation |
|---|---|---|---|
| A | 1001 | Positive | Positive |
| A | 1002 | Positive | Positive |
| A | 1003 | Negative | Negative |
| A | 1004 | Positive | Positive |
| A | 1005 | Negative | Negative |
| A | 1006 | Negative | Negative |
| B | 1007 | Negative | Negative |
| B | 1008 | Positive | Positive* |
| B | 1009 | Positive | Positive |
| B | 1010 | Negative | Negative |
| B | 1011 | Negative | Negative |
| B | 1012 | Positive | Positive |
| C | 1013 | Positive | Positive |
| C | 1014 | Negative | Negative |
| C | 1015 | Negative | Negative |
| C | 1016 | Negative | Negative |
| C | 1017 | Positive | Positive |
| C | 1018 | Positive | Positive |
| D | 1019 | Negative | Negative |
| D | 1020 | Negative | Negative |
| D | 1021 | Positive | Positive |
| D | 1022 | Positive | Positive |
| D | 1023 | Negative | Negative |
| D | 1024 | Positive | Positive |
| E | 1025 | Positive | Positive |
| E | 1026 | Negative | Negative |
| E | 1027 | Positive | Positive |
| E | 1028 | Positive | Positive# |
| E | 1029 | Negative | Negative |
| E | 1030 | Negative | Negative |

*Sample 1008 was interpreted as Invalid, and testing was repeated per IFU with valid result.
Sample 1028 was interpreted at 32 minutes, 7 minutes past the time range per IFU.

Testing of contrived low positive and negative samples by minimally trained operators at POC resulted in PPA=100% (15/15, 95% CI: 79.61%-100%) and NPA=100% (15/15, 95% CI: 79.61%-100%).

POC Flex Studies:

A hazard analysis was conducted in order to assess the main sources of potential errors that could occur at POC sites with the SCoV-2 Ag Detect™ Rapid Test Kit. Subsequently, Flex Studies were conducted as outlined below to evaluate the impact of errors or out-of-specifications conditions on the assay performance. The study was performed at InBios International Inc. (Seattle, Wash.) by trained operators.

Gamma-irradiated, SARS-Related Coronavirus 2 (SARS-CoV-2), USA-WA1/2020 isolate was obtained from ATCC via BEI (RD2660, RD 2765, Cat. NR-52287, Lot 70039067). SARS-CoV-2, isolate USA-WA1/2020 (NR-52287) was isolated from an oropharyngeal swab from a patient with a respiratory illness who developed clinical disease (COVID-19) in January 2020 in Washington, USA. NR-52287 was prepared from infected cultured Vero E6 epithelial cell lysate, gamma irradiated (5E+06 RADs) on dry ice, and then sonicated. NR-52287 is supplied at a concentration of 2.8E+06 $TCID_{50}$/mL.

Pooled nasal swab matrix consisted of nasal swabs taken from individual healthy donors (presumed SARS-CoV-2 negative), which were eluted in 0.5 mL PBS per swab and then pooled. The same negative matrix pool was used to generate all of the contrived samples in this study. Prior to pooling, the eluted nasal swabs in PBS were screened to confirm lack of background reactivity on the SCoV-2 Ag Detect™ Rapid Test. To screen each nasal swab eluted in PBS, 50 µL of each eluted sample was loaded directly onto a sterile swab compatible with the SCoV-2 Ag Detect™ Rapid Test so that the liquid was absorbed onto the swab. Each swab was then tested on the SCoV-2 Ag Detect™ Rapid Test following the instructions in the product insert.

The gamma-irradiated, SARS-CoV-2 virus stock solution was diluted in negative nasal swab matrix prepared as described above to a concentration of 1.3E+04 $TCID_{50}$/mL. This preparation was used throughout the study to prepare contrived samples.

The flex studies consisted of testing conditions shown below to simulate those that may be encountered or utilized by end users. Flex conditions do not strictly adhere to the instructions for use of the SCoV-2 Ag Detect™ Rapid Test, and were compared side-by-side to tests that are run as directed by the SCoV-2 Ag Detect™ Rapid Test instructions for use. Testing of different conditions was performed with a panel of 3 contrived low positive samples (targeted at twice the limit of detection) and 3 negative samples. Tests were interpreted as described in kit instructions. To be deemed passing, a flex study condition must not result in differences in sample status (i.e. no false positives or false negatives or invalid results) when compared to the same samples tested under recommended conditions and procedures.

Condition #1: Reading Time

The kit's instructions for use were followed with the exception of variations in reading times. Test results were evaluated at reading times above and below the specified reading time. The specified reading time is 20-25 minutes, and is highlighted in gray below. Passing results were obtained for reading times ranging from 5-75 minutes.

TABLE 23

| | Reading Time | | | |
|---|---|---|---|---|
| | 5 minutes | 10 minutes | 15 minutes | 20 minutes |
| Low Positive #1 | Positive | Positive | Positive | Positive |
| Low Positive #2 | Positive | Positive | Positive | Positive |
| Low Positive #3 | Positive | Positive | Positive | Positive |
| Negative sample #1 | Negative | Negative | Negative | Negative |
| Negative sample #2 | Negative | Negative | Negative | Negative |
| Negative sample #3 | Negative | Negative | Negative | Negative |
| Positive control #1 | Positive | Positive | Positive | Positive |
| Positive control #2 | Positive | Positive | Positive | Positive |
| Positive control #3 | Positive | Positive | Positive | Positive |

| | 25 minutes | 30 minutes | 45 minutes | 60 minutes | 75 minutes |
|---|---|---|---|---|---|
| Low Positive #1 | Positive | Positive | Positive | Positive | Positive |
| Low Positive #2 | Positive | Positive | Positive | Positive | Positive |
| Low Positive #3 | Positive | Positive | Positive | Positive | Positive |
| Negative sample #1 | Negative | Negative | Negative | Negative | Negative |
| Negative sample #2 | Negative | Negative | Negative | Negative | Negative |
| Negative sample #3 | Negative | Negative | Negative | Negative | Negative |
| Positive control #1 | Positive | Positive | Positive | Positive | Positive |
| Positive control #2 | Positive | Positive | Positive | Positive | Positive |
| Positive control #3 | Positive | Positive | Positive | Positive | Positive |

Condition #2: Lysis Buffer Volume

The kit's instructions for use were followed with the exception of variations in lysis buffer volume. Test results were evaluated for lysis buffer volumes above and below the specified volume. The specified lysis buffer volume is 8 drops, highlighted in gray below. Invalid tests were re-run once to determine final result. Passing results were obtained for 8-14 drops of Lysis buffer. The product insert for this assay was updated to emphasize to the end user the importance of dispensing 8 drops, and that fewer than 8 drops may cause erroneous results.

TABLE 24

| | Lysis Buffer Volume | | | | |
|---|---|---|---|---|---|
| | 4 Drops | 6 Drops | 8 Drops | 14 Drops | 16 Drops |
| Low Positive #1 | Invalid | Positive | Positive | Positive | Negative |
| Low Positive #2 | Invalid | Positive | Positive | Positive | Positive |
| Low Positive #3 | Invalid | Positive | Positive | Positive | Positive |
| Negative sample #1 | Invalid | Negative | Negative | Negative | Negative |
| Negative sample #2 | Invalid | Negative | Negative | Negative | Negative |
| Negative sample #3 | Invalid | Negative | Negative | Negative | Negative |
| Positive control #1 | Invalid | Positive | Positive | Positive | Positive |
| Positive control #2 | Invalid | Invalid | Positive | Positive | Positive |
| Positive control #3 | Invalid | Invalid | Positive | Positive | Positive |

Condition 3: Delay in Sample Testing

The kit's instructions for use were followed with the exception of delays in testing after sample preparation. Samples were prepared to be run in the specified manner, then were either stored in an empty tube or an opened paper pouch used to package the sterile swabs provided in kits for up to 90 minutes. Results are shown below, and properly conducted testing without delay is highlighted in gray. Passing results were obtained for sample testing after up to 90 minutes' storage in an empty tube or the empty paper pouch for swabs from the kit's original packaging.

TABLE 25

| | Delay in Sample Testing (Stored in Tube) | | | | |
|---|---|---|---|---|---|
| | No Delay | 15 ± 5 minutes | 30 ± 5 minutes | 60 ± 5 minutes | 90 ± 5 minutes |
| Low Positive #1 | Positive | Positive | Positive | Positive | Positive |
| Low Positive #2 | Positive | Positive | Positive | Positive | Positive |
| Low Positive #3 | Positive | Positive | Positive | Positive | Positive |
| Negative sample #1 | Negative | Negative | Negative | Negative | Negative |
| Negative sample #2 | Negative | Negative | Negative | Negative | Negative |
| Negative sample #3 | Negative | Negative | Negative | Negative | Negative |

TABLE 26

| | Delay in Sample Testing (Stored in Original Paper Wrap) | | | | |
|---|---|---|---|---|---|
| | No Delay | 15 ± 5 minutes | 30 ± 5 minutes | 60 ± 5 minutes | 90 ± 5 minutes |
| Low Positive #1 | Positive | Positive | Positive | Positive | Positive |
| Low Positive #2 | Positive | Positive | Positive | Positive | Positive |
| Low Positive #3 | Positive | Positive | Positive | Positive | Positive |
| Negative sample #1 | Negative | Negative | Negative | Negative | Negative |
| Negative sample #2 | Negative | Negative | Negative | Negative | Negative |
| Negative sample #3 | Negative | Negative | Negative | Negative | Negative |

Condition #4: Delay in Addition of Lysis Buffer

The kit's instructions for use were followed with the exception of delays in lysis buffer addition after sample insertion into cassettes. Specifically, the lysis buffer was added after the contrived swab specimens had been inserted into the cassette for approximately 1, 3, 5, and 25 minutes. Results are shown below, and properly conducted testing without delay is highlighted in gray. Passing results were obtained with lysis buffer application delayed up to 5 minutes.

TABLE 27

| | Delay in Adding Lysis Buffer | | | | |
|---|---|---|---|---|---|
| | No Delay | 1 minute | 3 minutes | 5 minutes | 25 minutes |
| Low Positive #1 | Positive | Positive | Positive | Positive | Positive |
| Low Positive #2 | Positive | Positive | Positive | Positive | Positive |

TABLE 27-continued

| | Delay in Adding Lysis Buffer | | | | |
|---|---|---|---|---|---|
| | No Delay | 1 minute | 3 minutes | 5 minutes | 25 minutes |
| Low Positive #3 | Positive | Positive | Positive | Positive | Negative |
| Negative sample #1 | Negative | Negative | Negative | Negative | Negative |
| Negative sample #2 | Negative | Negative | Negative | Negative | Negative |
| Negative sample #3 | Negative | Negative | Negative | Negative | Negative |

Condition #5: Order of Operational Steps

The kit's instructions for use were followed with the exception of the order of operational steps. Tests were performed where lysis buffer was added to the swab prior to the swab insertion, and where lysis buffer was added to the sample port prior to swab insertion. Invalid tests were rerun once to determine final result. Properly conducted testing is highlighted in gray below. False negatives were observed when operational steps were completed in an incorrect order.

TABLE 28

| | Order of Operational Steps | | |
|---|---|---|---|
| | Correct Order | Incorrect Order: Lysis Buffer (8 drops) added to swab prior to swab insertion | Incorrect Order: Lysis Buffer (8 drops) added to sample port prior to swab insertion |
| Low Positive #1 | Positive | Negative | Negative |
| Low Positive #2 | Positive | Negative | Negative |
| Low Positive #3 | Positive | Positive | Negative |
| Negative sample #1 | Negative | Negative | Negative |
| Negative sample #2 | Negative | Negative | Negative |
| Negative sample #3 | Negative | Initial test invalid, repeat test Negative | Negative |

Condition #6: Swab Insertion

The kit's instructions for use were followed with the exception of the swab being incompletely inserted into the sample port or incompletely covering the sample port. Results are shown below, and proper swab insertion is highlighted in gray. Passing results were obtained even when the swab was not fully in contact with the sample pad in the sample port, but not when the port was incompletely covered by the swab. The kit's instructions for use were edited to reflect the importance of the swab completely covering the sample pad.

TABLE 29

| | Swab Placement | | | |
|---|---|---|---|---|
| | Correct swab insertion | Incomplete swab insertion (swab not in full contact with sample port) | Incomplete coverage of sample pad by swab (−20% offset) | Incomplete coverage of sample pad by swab (+20% offset) |
| Low Positive #1 | Positive | Positive | Positive | Positive |
| Low Positive #2 | Positive | Positive | Positive | Positive |
| Low Positive #3 | Positive | Positive | Negative | Positive |
| Negative sample #1 | Negative | Negative | Negative | Negative |
| Negative sample #2 | Negative | Negative | Negative | Negative |
| Negative sample #3 | Negative | Negative | Negative | Negative |
| Positive control #1 | Positive | Positive | (not tested) | (not tested) |
| Positive control #2 | Positive | Positive | (not tested) | (not tested) |
| Positive control #3 | Positive | Positive | (not tested) | (not tested) |

Condition #7: Disturbance During Analysis

The kit's instructions for use were followed with the exception of the cassette being disturbed during analysis. During the incubation period, the test was picked up and moved to another horizontal surface at least 6 feet away, or picked up and dropped from a height of at least 3 feet and returned to initial surface. If the swab fell out of the cassette, then the swab was reinserted to the cassette. Results are shown below, with undisturbed testing highlighted in gray. Passing results were observed under all conditions where the test was picked up and moved, or picked up and dropped.

TABLE 30

| Disturbance During Analysis | | | |
|---|---|---|---|
| | Test not disturbed | Test picked up and moved | Test picked up and dropped |
| Low Positive #1 | Positive | Positive | Positive |
| Low Positive #2 | Positive | Positive | Positive |
| Low Positive #3 | Positive | Positive | Positive |
| Negative sample #1 | Negative | Negative | Negative |
| Negative sample #2 | Negative | Negative | Negative |
| Negative sample #3 | Negative | Negative | Negative |

Condition #8: Placement on Non-level Surface

The kit's instructions for use were followed with the exception of the cassettes being placed on surfaces of varying degrees of incline. Specified placement is on a flat surface, highlighted in gray. A false negative result was observed in one of three replicates when the test was run nearly upright (~90°). Passing results were observed for all other non-level conditions.

TABLE 31

| Orientation of Cassette | | | | |
|---|---|---|---|---|
| | Flat | Inclined (20°-45°) | Declined (20°-45°) | Nearly Upright (~90°) |
| Low Positive #1 | Positive | Positive | Positive | Positive |
| Low Positive #2 | Positive | Positive | Positive | Positive |
| Low Positive #3 | Positive | Positive | Positive | Negative |
| Negative sample #1 | Negative | Negative | Negative | Negative |
| Negative sample #2 | Negative | Negative | Negative | Negative |
| Negative sample #3 | Negative | Negative | Negative | Negative |

Condition #9: Temperature and Humidity

The kit's instructions for use were followed with the exception of deviations in ambient temperature and relative humidity (% RH) during the test's incubation period. Testing under ambient conditions in an environmentally-controlled lab is highlighted in gray. Passing results were obtained even when the test was run under temperature and humidity challenges.

TABLE 32

| Temperature and Humidity | | | |
|---|---|---|---|
| | Ambient lab conditions | 40 ± 2° C. and 95 ± 5% RH | 5 ± 3° C. and <15% RH |
| Low Positive #1 | Positive | Positive | Positive |
| Low Positive #2 | Positive | Positive | Positive |
| Low Positive #3 | Positive | Positive | Positive |
| Negative sample #1 | Negative | Negative | Negative |
| Negative sample #2 | Negative | Negative | Negative |
| Negative sample #3 | Negative | Negative | Negative |

Condition #10: Lighting Conditions

Impact of lighting conditions was assessed by having an inexperienced user read results in various lighting conditions. Incandescent lighting was approximated with a LED lamp on low setting. Tests read under dim lighting were read in a dark portion of laboratory, with only nearby hallway light exposure. Brighter light, such as direct sunlight, helped the inexperienced user see low intensity test lines more consistently. Results are shown below, with testing under common fluorescent lighting highlighted in gray. False negative results were observed for positive samples read under incandescent and low light conditions. Passing results were observed under all other lighting conditions. The kit's instructions for use were edited to reflect the importance of the proper lighting conditions.

TABLE 33

| Light Sources (tests read by an inexperienced user) | | | | | |
|---|---|---|---|---|---|
| | Fluorescent | Incandescent | Ambient light on overcast day | Bright sunlight* | Low light** |
| Low Positive #1 | Positive | Positive | Positive | Positive | Positive |
| Low Positive #2 | Positive | Negative | Positive | Positive | Negative |
| Low Positive #3 | Positive | Positive | Positive | Positive | Negative |
| Negative sample #1 | Negative | Negative | Negative | Negative | Negative |
| Negative sample #2 | Negative | Negative | Negative | Negative | Negative |
| Negative sample #3 | Negative | Negative | Negative | Negative | Negative |

*read near a window
**room lit only by light from an adjacent hallway/room

Condition #11: Frozen and Refrigerated Kit Storage

The kit's instructions for use were followed with the exception of the kit being frozen at −20° C. or refrigerated at 2-8° C., with or without equilibration to room temperature (RT) prior to testing. Specified conditions for kit storage are 15-30° C., highlighted in gray. Passing results were observed even after the kit was stored under freezing or refrigerated conditions up to 24 hours.

TABLE 34

Frozen and Refrigerated Storage

| | No Freezing or Refrigeration | Frozen Storage | | | |
|---|---|---|---|---|---|
| | | 8 hours (tested immediately) | 8 hours (brought to RT) | 24 hours (tested immediately) | 24 hours (brought to RT) |
| Low Positive #1 | Positive | Positive | Positive | Positive | Positive |
| Low Positive #2 | Positive | Positive | Positive | Positive | Positive |
| Low Positive #3 | Positive | Positive | Positive | Positive | Positive |
| Negative sample #1 | Negative | Negative | Negative | Negative | Negative |
| Negative sample #2 | Negative | Negative | Negative | Negative | Negative |
| Negative sample #3 | Negative | Negative | Negative | Negative | Negative |
| | Refrigerated Storage | | | | |
| | 8 hours (tested immediately) | 8 hours (brought to RT) | 24 hours (tested immediately) | 24 hours (brought to RT) | |
| Low Positive #1 | Positive | Positive | Positive | Positive | |
| Low Positive #2 | Positive | Positive | Positive | Positive | |
| Low Positive #3 | Positive | Positive | Positive | Positive | |
| Negative sample #1 | Negative | Negative | Negative | Negative | |
| Negative sample #2 | Negative | Negative | Negative | Negative | |
| Negative sample #3 | Negative | Negative | Negative | Negative | |

Condition #12: Improper Handling

The kit's instructions for use were followed with the exception of the nitrocellulose membrane or the lysis buffer bottle tip being handled improperly (e.g. touched by gloved or bare hands, or coming into contact with hand lotion or hand sanitizer). Due to safety concerns, no testing was conducted with touching the tip of the lysis buffer bottle with bare hands. Results are shown below, and properly conducted testing without touching membrane or bottle tip is highlighted in gray. Passing results were observed even when the test was handled improperly.

TABLE 35

Improper Handling

| | No touching of membrane or bottle tip | Nitrocellulose Membrane Touched | | | |
|---|---|---|---|---|---|
| | | With gloves | Without gloves | Without gloves, with hand lotion | Without gloves, with hand sanitizer |
| Low Positive #1 | Positive | Positive | Positive | Positive | Positive |
| Low Positive #2 | Positive | Positive | Positive | Positive | Positive |
| Low Positive #3 | Positive | Positive | Positive | Positive | Positive |
| Negative sample #1 | Negative | Negative | Negative | Negative | Negative |
| Negative sample #2 | Negative | Negative | Negative | Negative | Negative |
| Negative sample #3 | Negative | Negative | Negative | Negative | Negative |
| | Lysis Buffer Bottle Tip Touched | | | | |
| | With gloves | With gloves, with hand lotion | With gloves, with hand sanitizer | | |
| Low Positive #1 | Positive | Positive | Positive | | |
| Low Positive #2 | Positive | Positive | Positive | | |
| Low Positive #3 | Positive | Positive | Positive | | |
| Negative sample #1 | Negative | Negative | Negative | | |
| Negative sample #2 | Negative | Negative | Negative | | |
| Negative sample #3 | Negative | Negative | Negative | | |

Condition #13: Cassette Drop Test

The kit's instructions for use were followed with the exception of the cassette being dropped from >5 feet after unpouching but prior to testing. If a cassette broke open after being dropped, then an inexperienced user reassembled the cassette prior to testing. Cassettes that were not dropped are highlighted in gray below. Passing results were observed even for cassettes that were dropped and reclosed prior to testing.

TABLE 36

Cassette Drop Test

| | Test not dropped | Cassette dropped from >5 feet |
|---|---|---|
| Low Positive #1 | Positive | Positive |
| Low Positive #2 | Positive | Positive |
| Low Positive #3 | Positive | Positive |
| Negative sample #1 | Negative | Negative |
| Negative sample #2 | Negative | Negative |
| Negative sample #3 | Negative | Negative |

Thirteen (13) conditions were selected to evaluate the robustness of the SCoV-2 Ag Detect™ Rapid Test Kit. Seven out of the 13 conditions demonstrated robustness to conditions outside those recommended in the kit's instruction for use. Six conditions had some false negatives when handled outside of the recommended conditions. Risk analysis shows that these conditions are expected to occur rarely at a POC site. However, the product insert has been carefully written to highlight these areas of potential concerns so that the end user understands the importance of carefully following the instructions for use. Overall, the SCoV-2 Ag Detect™ Rapid Test Kit demonstrates that it is robust and will be reliable in a POC setting.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

All numerical values provided herein, with the exception of numerical values reflecting actual data, include values "about" the recited value, such as or within +/−5% of the recited value.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A lateral flow assay cassette comprising:
   a sample pad;
   a sample port that allows access to the sample pad;
   a membrane;
   an outer housing comprising a fixed external result display window that provides visibility to the membrane; and
   a swab holder that secures a swab having a stem and a head, the swab holder comprising protrusions that secure the swab stem such that the swab head is in the sample port directly above the sample pad or directly in contact with the sample pad.

2. The lateral flow assay cassette of claim 1, wherein the swab holder comprising the protrusions that secure the swab stem via friction secures the swab head directly above the sample pad, and wherein the swab does not come into direct contact with the sample pad.

3. The lateral flow assay cassette of claim 1, wherein the swab holder comprising the protrusions that secure the swab stem via friction secures the swab head directly in contact with the sample pad.

4. The lateral flow assay cassette of claim 1, wherein the protrusions are sized to secure a swab stem of a specific diameter.

5. The lateral flow assay cassette of claim 4, wherein the protrusions are in a grabber or peg configuration.

6. The lateral flow assay cassette of claim 1, wherein the protrusions are flexible and sized to secure swab stems of various diameters.

7. The lateral flow assay cassette of claim 6, wherein the protrusions are in featherboard configuration.

8. A method of detecting an analyte, the method comprising:
   a) providing a lateral flow assay cassette having a sample pad, a sample port that allows access to the sample pad, a membrane, an outer housing comprising a fixed external result display window that provides visibility to the membrane, and a swab holder that secures a swab having a stem and a head, the swab holder comprising protrusions that secure the swab stem such that the swab head is in the sample port directly above the sample pad or directly in contact with the sample pad;
   b) collecting a sample from a subject using the swab;
   c) placing the swab stem into the swab holder such that the swab head is in the sample port directly above the sample pad or directly in contact with the sample pad;
   d) adding an appropriate amount of lysis buffer directly to the swab head after step c); and
   e) eluting the sample from the swab head with the lysis buffer directly into the sample port and the sample pad, wherein said elution is accomplished by adding one or more drops from a lysis buffer dropper bottle.

9. The method of claim 8, wherein the swab holder comprising the protrusions that secure the swab stem via friction secures the swab head directly above the sample pad, and wherein the swab does not come into direct contact with the sample pad.

10. The method of claim 8, wherein the swab holder comprising the protrusions that secure the swab stem via friction secures the swab head directly in contact with the sample pad.

11. The method of claim 8, wherein the sample is from a nose, nasopharyngeal cavity, the oropharyngeal cavity, the mid-turbinate region, mouth, tongue, throat, teeth, gums, tonsils, outer ear canal, skin, wounds, lesions, urethra, vagina, cervix, anus, or rectum, or is a nasal or ear secretion, sputum, saliva, a vaginal secretion, pus, blood, urine, feces, a bronchoalveolar lavage sample, or a surgical sample.

12. The method of claim 8, wherein the detection of the analyte indicates the presence of an infectious agent in the subject.

13. The method of claim 12, wherein the infectious agent is Human coronavirus, 229E; Human coronavirus, OC43; Human coronavirus, NL63; MERS-coronavirus; SARS-CoV-2; Adenovirus 21; Human Metapneumovirus (hMPV); Parainfluenza virus 1; Parainfluenza virus 2; Parainfluenza virus 3; Parainfluenza virus 4a; Influenza A; Influenza B; Enterovirus D68; Respiratory syncytial virus; Rhinovirus 40; *Haemophilus* influenza; *Streptococcus pneumonia; Streptococcus pyogenes; Candida albicans; Bordetella pertussis; Mycoplasma* pneumonia; *Chlamydia* pneumonia; *Legionella pneumophila*; or *Staphylococcus aureus*.

14. The method of claim 8, wherein the analyte is RNA, DNA, or protein.

15. The method of claim 8, further comprising detecting the analyte within 30 minutes.

16. The method of claim 8, further comprising:
  e) processing the analyte on the swab head;
  f) introducing sample from the swab head to the sample pad;
  g) running the assay; and
  h) producing an assay result.

17. The method of claim 8, further comprising adding an appropriate amount of chase buffer to the swab head after step (d).

18. A kit comprising:
  a lateral flow assay cassette comprising:
  a sample pad;
  a sample port that allows access to the sample pad;
  a membrane:
  an outer housing comprising a fixed external result display window that provides visibility to the membrane;
  a swab holder that secures a swab having a stem and a head, the swab holder comprising protrusions that secure the swab stem such that the swab head is in the sample port directly above the sample pad or directly in contact with the sample pad;
  a swab having a stem with a diameter sized to be secured by the swab holder; and
  lysis buffer adapted for dropping a set number of drops of the lysis buffer on the swab head.

19. The kit of claim 18, wherein the kit further comprises instructions of use of the lateral flow assay cassette with a sample, wherein the sample is from a nose, nasopharyngeal cavity, the oropharyngeal cavity, the mid-turbinate region, mouth, tongue, throat, teeth, gums, tonsils, outer ear canal, skin, wounds, lesions, urethra, vagina, cervix, anus, or rectum, or is a nasal or ear secretion, sputum, saliva, a vaginal secretion, pus, blood, urine, feces, a bronchoalveolar lavage sample, or a surgical sample.

* * * * *